United States Patent
Probst et al.

(10) Patent No.: US 11,208,465 B2
(45) Date of Patent: Dec. 28, 2021

(54) DIAGNOSIS OF BLISTERING AUTOIMMUNE DISEASE

(71) Applicant: EUROIMMUN Medizinische Labordiagnostika AG, Luebeck (DE)

(72) Inventors: Christian Probst, Ratzeburg (DE); Christiane Radzimski, Reinfeld (DE); Lars Komorowski, Ratzeburg (DE); Wolfgang Schlumberger, Gross Groenau (DE); Winfried Stoecker, Gross Groenau (DE); Detlef Zillikens, Luebeck (DE); Christoph Hammers, Luebeck (DE); Enno Schmidt, Luebeck (DE); Stephanie Goletz, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 16/591,333

(22) Filed: Oct. 2, 2019

(65) Prior Publication Data

US 2020/0123230 A1 Apr. 23, 2020

(30) Foreign Application Priority Data

Oct. 22, 2018 (EP) .................... 18201752

(51) Int. Cl.
| | |
|---|---|
| *C07K 14/78* | (2006.01) |
| *C07K 16/28* | (2006.01) |
| *G01N 33/58* | (2006.01) |
| *G01N 33/53* | (2006.01) |
| *C07K 17/00* | (2006.01) |
| *A61K 38/00* | (2006.01) |

(52) U.S. Cl.
CPC .............. *C07K 14/78* (2013.01); *C07K 16/28* (2013.01); *C07K 17/00* (2013.01); *G01N 33/53* (2013.01); *G01N 33/58* (2013.01); *A61K 38/00* (2013.01)

(58) Field of Classification Search
None
See application file for complete search history.

(56) References Cited

U.S. PATENT DOCUMENTS 6,682,911 B1   1/2004  Burgeson et al.

FOREIGN PATENT DOCUMENTS

JP   2001-519180   10/2001

OTHER PUBLICATIONS

Search Report dated Jul. 31, 2019 in European Patent Application No. 18201752.5 with English translation, 18 pages.
Anonymous, PAC079Hu01 Polyclonal Antibody to Laminin Beta 4 (LAMb4) Organism Species: Homo sapiens (Human) [Product Information], 2014, pp. 1-2; Found Apr. 15, 2019: URL: http://www.cloud-clone.com/manual/Polyclonal-Antibody-to-Laminin-Beta-4--LAMb4-- PAC079Hu01.pdf.
Japanese Office Action dated Aug. 27, 2021 in Japanese Application No. 2019-190722, with English translation, 9 pages.

*Primary Examiner* — Marianne P Allen
(74) *Attorney, Agent, or Firm* — Grüneberg and Myers PLLC

(57) ABSTRACT

A polypeptide contains laminin beta-4 and a carrier contains the polypeptide. An antibody, preferably autoantibody, is against laminin beta-4. Furthermore, use of the polypeptide, carrier or autoantibody for the diagnosis of a disease, and a method with the step of detecting an autoantibody against laminin beta-4 in a sample are described.

6 Claims, 5 Drawing Sheets

Specification includes a Sequence Listing.

SEQUENCE LISTING

```
<160> NUMBER OF SEQ ID NOS: 31

<210> SEQ ID NO 1
<211> LENGTH: 45
<212> TYPE: DNA
<213> ORGANISM: Artificial Sequence
<220> FEATURE:
<223> OTHER INFORMATION: Primer sense LAMB4

<400> SEQUENCE: 1
ataggtctca catgcaattt caactgaccc ttttttttgca ccttg                45

<210> SEQ ID NO 2
<211> LENGTH: 45
<212> TYPE: DNA
<213> ORGANISM: Artificial Sequence
<220> FEATURE:
<223> OTHER INFORMATION: Primer anti-sense LAMB4

<400> SEQUENCE: 2
ataggtctcg tcgaggctat agcacctagc atattttttt tcttg                45
```

<210> SEQ ID NO 3
<211> LENGTH: 48
<212> TYPE: DNA
<213> ORGANISM: Artificial Sequence
<220> FEATURE:
<223> OTHER INFORMATION: Primer anti-sense LAMB4-Stop

<400> SEQUENCE: 3
ataggtctcc tcgagctagc tatagcacct agcatatttt ttttcttg                48

<210> SEQ ID NO 4
<211> LENGTH: 5758
<212> TYPE: DNA
<213> ORGANISM: Artificial Sequence
<220> FEATURE:
<223> OTHER INFORMATION: pTriEx-1

<400> SEQUENCE: 4
ggggaattgt gagcggataa caattccccg gagttaatcc gggacccttta attcaaccca      60 acacaatata ttatagttaa ataagaatta ttatcaaatc atttgtatat taattaaaat     120
actatactgt aaattacatt ttatttacaa tcaaaggaga tataccatgg cgatatcccg     180
ggagctcgtg gatccgaatt ctcagatctc ggcgcgcctg caggtcgacg gtaccggttc     240
gaagcttgcg gccgcacagc tgtatacacg tgcaagccag ccagaactcg ccccggaaga     300
ccccgaggat ctcgagcacc accatcacca tcaccatcac taagtgatta acctcaggtg     360
caggctgcct atcagaaggt ggtggctggt gtggccaatg ccctggctca caaataccac     420
tgagatcgat cttttttccct ctgccaaaaa ttatggggac atcatgaagc cccttgagca     480
tctgacttct ggctaataaa ggaaatttat tttcattgca atagtgtgtt ggaatttttt     540
gtgtctctca ctcggaagga catatgggag ggcaaatcat ttaaaacatc agaatgagta     600
tttggtttag agtttggcaa catatgccca tatgtaacta gcataacccc ttggggcctc     660
taaacgggtc ttgaggggtt ttttgctgaa agcatgcgga ggaaattctc cttgaagttt     720
ccctggtgtt caaagtaaag gagtttgcac cagacgcacc tctgttcact ggtccggcgt     780
attaaaacac gatacattgt tattagtaca tttattaagc gctagattct gtgcgttgtt     840
gatttacaga caattgttgt acgtatttta ataattcatt aaatttataa tctttagggt     900
ggtatgttag agcgaaaatc aaatgatttt cagcgtcttt atatctgaat ttaaatatta     960
aatcctcaat agatttgtaa aataggtttc gattagtttc aaacaagggt tgtttttccg    1020
aaccgatggc tggactatct aatggatttt cgctcaacgc cacaaaactt gccaaatctt    1080
gtagcagcaa tctagctttg tcgatattcg tttgtgtttt gttttgtaat aaaggttcga    1140
cgtcgttcaa atattatgc gcttttgtat tctttcatc actgtcgtta gtgtacaatt    1200
gactcgacgt aaacacgtta atagagcttg gacatattt aacatcgggc gtgttagctt    1260
tattaggccg attatcgtcg tcgtcccaac cctcgtcgtt agaagttgct tccgaagacg    1320
attttgccat agccacacga cgcctattaa ttgtgtcggc taacacgtcc gcgatcaaat    1380
ttgtagttga gcttttttgga attatttctg attgcgggcg ttttggcg ggtttcaatc    1440 taactgtgcc cgattttaat tcagacaaca cgttagaaag cgatggtgca ggcggtggta    1500
acatttcaga cggcaaatct actaatggcg gcggtggtgg agctgatgat aaatctacca    1560
tcggtggagg cgcaggcggg gctgcgggc gaggcggagg cggaggtggt ggcggtgatg    1620
cagacggcgg tttaggctca aatgtctctt taggcaacac agtcggcacc tcaactattg    1680
tactggtttc gggcgccgtt tttggtttga ccggtctgag acgagtgcga ttttttttcgt    1740

```
ttctaatagc ttccaacaat tgttgtctgt cgtctaaagg tgcagcgggt tgaggttccg    1800
tcggcattgg tggagcgggc ggcaattcag acatcgatgg tggtggtggt ggtggaggcg    1860
ctggaatgtt aggcacggga gaaggtggtg gcggcggtgc cgccggtata atttgttctg    1920
gtttagtttg ttcgcgcacg attgtgggca ccggcgcagg cgccgctggc tgcacaacgg    1980
aaggtcgtct gcttcgaggc agcgcttggg gtggtggcaa ttcaatatta taattggaat    2040
acaaatcgta aaaatctgct ataagcattg taatttcgct atcgtttacc gtgccgatat    2100
ttaacaaccg ctcaatgtaa gcaattgtat tgtaaagaga ttgtctcaag ctcggaacgc    2160
tgcgctcggt cgttcggctg cggcgagcgg tatcagctca ctcaaaggcg gtaatacggt    2220
tatccacaga atcaggggat aacgcaggaa agaacatgtg agcaaaaggc cagcaaaagg    2280
ccaggaaccg taaaaaggcc gcgttgctgg cgttttttcca taggctccgc cccctgacg    2340 agcatcacaa aaatcgacgc tcaagtcaga ggtggcgaaa cccgacagga ctataaagat    2400
accaggcgtt tccccctgga agctccctcg tgcgctctcc tgttccgacc ctgccgctta    2460
ccggatacct gtccgccttt ctcccttcgg gaagcgtggc gctttctcaa tgctcacgct    2520
gtaggtatct cagttcggtg taggtcgttc gctccaagct gggctgtgtg cacgaacccc    2580
ccgttcagcc cgaccgctgc gccttatccg gtaactatcg tcttgagtcc aacccggtaa    2640
gacacgactt atcgccactg gcagcagcca ctggtaacag gattagcaga gcgaggtatg    2700
taggcggtgc tacagagttc ttgaagtggt ggcctaacta cggctacact agaaggacag    2760
tatttggtat ctgcgctctg ctgaagccag ttaccttcgg aaaaagagtt ggtagctctt    2820
gatccggcaa acaaaccacc gctggtagcg gtggtttttt tgtttgcaag cagcagatta    2880
cgcgcagaaa aaaaggatct caagaagatc ctttgttacc aatgcttaat cagtgaggca    2940
cctatctcag cgatctgtct atttcgttca tccatagttg cctgactccc cgtcgtgtag    3000
ataactacga tacgggaggg cttaccatct ggccccagtg ctgcaatgat accgcgagac    3060
ccacgctcac cggctccaga tttatcagca ataaaccagc cagccggaag ggccgagcgc    3120
agaagtggtc ctgcaacttt atccgcctcc atccagtcta ttaattgttg ccgggaagct    3180
agagtaagta gttcgccagt taatagtttg cgcaacgttg ttgccattgc tacaggcatc    3240
gtggtgtcac gctcgtcgtt tggtatggct tcattcagct ccggttccca acgatcaagg    3300
cgagttacat gatcccccat gttgtgcaaa aaagcggtta gctccttcgg tcctccgatc    3360
gttgtcagaa gtaagttggc cgcagtgtta tcactcatgg ttatggcagc actgcataat    3420
tctcttactg tcatgccatc cgtaagatgc ttttctgtga ctggtgagta ctcaaccaag    3480
tcattctgag aatagtgtat gcggcgaccg agttgctctt gcccggcgtc aatacgggat    3540
aataccgcgc cacatagcag aactttaaaa gtgctcatca ttggaaaacg ttcttcgggg    3600
cgaaaactct caaggatctt accgctgttg agatccagtt cgatgtaacc cactcgtgca    3660
cccaactgat cttcagcatc ttttactttc accagcgttt ctgggtgagc aaaaacagga    3720
aggcaaaatg ccgcaaaaaa gggaataagg gcgacacgga aatgttgaat actcatactc    3780
ttcctttttc aatattattg aagcatttat cagggttatt gtctcatgtc cgcgcgtttc    3840
ctgcatcttt taatcaaatc ccaagatgtg tataaaccac caaactgcca aaaatgaaa    3900 actgtcgaca agctctgtcc gtttgctggc aactgcaagg gtctcaatcc tatttgtaat    3960
tattgaataa taaacaatt ataaatgtca aatttgtttt ttattaacga tacaaaccaa    4020
acgcaacaag aacatttgta gtattatcta taattgaaaa cgcgtagtta taatcgctga    4080
```

| | |
|---|---|
| ggtaatattt aaaatcattt tcaaatgatt cacagttaat ttgcgacaat ataattttat | 4140 |
| tttcacataa actagacgcc ttgtcgtctt cttcttcgta ttccttctct ttttcatttt | 4200 |
| tctcttcata aaaattaaca tagttattat cgtatccata tatgtatcta tcgtatagag | 4260 |
| taaattttt gttgtcataa atatatatgt cttttttaat ggggtgtata gtaccgctgc | 4320 |
| gcatagtttt tctgtaattt acaacagtgc tattttctgg tagttcttcg gagtgtgttg | 4380 |
| ctttaattat taaatttata taatcaatga atttgggatc gtcggttttg tacaatatgt | 4440 |
| tgccggcata gtacgcagct tcttctagtt caattacacc atttttagc agcaccggat | 4500 |
| taacataact ttccaaaatg ttgtacgaac cgttaaacaa aaacagttca cctccctttt | 4560 |
| ctatactatt gtctgcgagc agttgtttgt tgttaaaaat aacagccatt gtaatgagac | 4620 |
| gcacaaacta atatcacaaa ctggaaatgt ctatcaatat atagttgctc tagttattaa | 4680 |
| tagtaatcaa ttacggggtc attagttcat agcccatata tggagttccg cgttacataa | 4740 |
| cttacggtaa atggcccgcc tggctgaccg cccaacgacc cccgcccatt gacgtcaata | 4800 |
| atgacgtatg ttcccatagt aacgccaata gggactttcc attgacgtca atgggtggac | 4860 |
| tatttacggt aaactgccca cttggcagta catcaagtgt atcatatgcc aagtacgccc | 4920 |
| cctattgacg tcaatgacgg taaatggccc gcctggcatt atgcccagta catgaccta | 4980 |
| tgggactttc ctacttggca gtacatctac gtattagtca tcgctattac catgcatggt | 5040 |
| cgaggtgagc cccacgttct gcttcactct ccccatctcc cccccctccc caccccccaat | 5100 |
| tttgtattta tttattttt aattatttg tgcagcgatg ggggcggggg gggggggggg | 5160 |
| gcgcgcgcca ggcggggcgg ggcggggcga ggggcggggc ggggcgaggc ggagaggtgc | 5220 |
| ggcggcagcc aatcagagcg gcgcgctccg aaagtttcct tttatggcga ggcggcggcg | 5280 |
| gcggcggccc tataaaaagc gaagcgcgcg gcgggcggga gtcgctgcga cgctgccttc | 5340 |
| gccccgtgcc ccgctccgcc gccgcctcgc gccgcccgcc ccggctctga ctgaccgcgt | 5400 |
| tactcccaca ggtgagcggg cgggacggcc cttctccttc gggctgtaat tagcgcttgg | 5460 |
| tttaatgacg gcttgtttct tttctgtggc tgcgtgaaag ccttgagggg ctccgggagg | 5520 |
| gccctttgtg cgggggagc ggctcgggc tgtccgcggg gggacggctg ccttcggggg | 5580 |
| ggacggggca gggcggggtt cggcttctgg cgtgtgaccg gcggctctag agcctctgct | 5640 |
| aaccatgttc atgccttctt cttttccta cagctcctgg gcaacgtgct ggttattgtg | 5700 |
| ctgtctcatc attttggcaa agaattggat cggaccgaaa ttaatacgac tcactata | 5758 |

<210> SEQ ID NO 5
<211> LENGTH: 10897
<212> TYPE: DNA
<213> ORGANISM: Artificial Sequence
<220> FEATURE:
<223> OTHER INFORMATION: pTriEx-1-LAMB4(IF1)[human]

<400> SEQUENCE: 5

| | |
|---|---|
| ggagtcgctg cgacgctgcc ttcgccccgt gccccgctcc gccgccgcct cgcgccgccc | 60 |
| gccccggctc tgactgaccg cgttactccc acaggtgagc gggcgggacg gcccttctcc | 120 |
| ttcgggctgt aattagcgct tggtttaatg acgcttgtt tcttttctgt ggctgcgtga | 180 |
| aagccttgag gggctccggg agggcccttt gtgcgggggg agcggctcgg ggctgtccgc | 240 |
| gggggacgg ctgccttcgg ggggacggg gcagggcggg gttcggcttc tggcgtgtga | 300 |
| ccggcggctc tagagcctct gctaaccatg ttcatgcctt cttctttttc ctacagctcc | 360 |
| tgggcaacgt gctggttatt gtgctgtctc atcattttgg caaagaattg gatcggaccg | 420 |

```
aaattaatac gactcactat aggggaattg tgagcggata acaattcccc ggagttaatc    480
cgggaccttt aattcaaccc aacacaatat attatagtta aataagaatt attatcaaat    540
catttgtata ttaattaaaa tactatactg taaattacat tttatttaca atcaaaggag    600
atataccatg caatttcaac tgacccttt tttgcacctt gggtggctca gttactcaaa    660
agctcaagat gactgcaaca ggggtgcctg tcatcccacc actggtgatc tcctggtggg    720
caggaacacg cagcttatgg cttcttctac ctgtgggctg agcagagccc agaaatactg    780
catcctcagt tacctggagg gggaacaaaa atgcttcatc tgtgactcta gatttccata    840
tgatccgtat gaccaaccca acagccacac cattgagaat gtcattgtaa gttttgaacc    900
agacagagaa aagaaatggt ggcaatctga aaatggtctt gatcatgtca gcatcagact    960
ggacttagag gcattatttc ggttcagcca cctatcctg acctttaaga cttttcggcc   1020
tgctgcaatg ttagttgaac gttccacaga ctatggacac aactggaaag tgttcaaata   1080
ttttgcaaaa gactgtgcca cttcctttcc taacatcaca tctggccagg cccagggagt   1140
gggagacatt gtttgtgact ccaaatactc ggatattgaa ccctcaacag gtggagaggt   1200
tgttttaaaa gttttggatc ccagttttga aattgaaaac ccttatagcc cctacatcca   1260
agaccttgtg acattgacaa acctgaggat aaactttacc aagctccaca cccttgggga   1320
tgctttgctt ggaaggaggc aaaatgattc ccttgataaa tactactatg ctctgtacga   1380
gatgattgtt cggggaagct gcttttgcaa tggccatgct agcgaatgtc gccctatgca   1440
gaagatgcgg ggagatgttt tcagccctcc tggaatggtt cacggtcagt gtgtgtgtca   1500
gcacaataca gatggtccga actgtgagag atgcaaggac ttcttccagg atgctccttg   1560
gaggccagct gcagacctcc aggacaacgc ttgcagatcg tgcagctgta acagccactc   1620
cagccgctgt cactttgaca tgactacgta cctggcaagc ggtggcctca gcggggggcgt   1680 gtgtgaagac tgccagcaca cactgagggg cagcactgc gaccgctgca gacccctctt   1740
ctacagggac ccgctcaaga ccatctcaga tccctacgcg tgcattcctt gtgaatgtga   1800
ccccgatggg accatatctg gtggcatttg tgtgagccac tctgatcctg ccttagggtc   1860
tgtggctggc cagtgccttt gtaaagagaa cgtggaagga gccaaatgcg accagtgcaa   1920
acccaaccac tatggactaa gcgccaccga ccccctgggc tgccagccct gcgactgtaa   1980
ccccccttgg agtctgccat tcttgacctg tgatgtggat acaggccaat gcttgtgcct   2040
gtcatatgtc accggagcac actgcgaaga atgcactgtt ggatactggg gcctgggaaa   2100
tcatctccat gggtgttctc cctgtgactg tgatattgga ggtgcttatt ctaacgtgtg   2160
ctcacccaag aatgggcagt gtgaatgccg cccacatgtc actggccgta gctgctctga   2220 accagccct ggctacttct tgctcccttt gaatttctat ctctacgagg cagaggaagc   2280
cacaacactc caaggactgg cgcctttggg ctcggagacg tttggccaga gtcctgctgt   2340
tcacgttgtt ttaggagagc cagttcctgg gaaccctgtt acatggactg gacctggatt   2400
tgccagggtt ctccctgggg ctggcttgag atttgctgtc aacaacattc cctttcctgt   2460
ggacttcacc attgccattc actatgaaac ccagtctgca gctgactgga ctgtccagat   2520
tgtggtgaac cccctggag ggagtgagca ctgcataccc aagactctac agtcaaagcc   2580
tcagtctttt gccttaccag cggctacgag aatcatgctg cttcccacac ccatctgttt   2640
agaaccagat gtacaatatt ccatagatgt ctattttct cagcctttgc aaggagagtc   2700
ccacgctcat tcacatgtcc tggtggactc tcttggcctt attccccaaa tcaattcatt   2760
```

```
ggagaatttc tgcagcaagc aggacttaga tgagtatcag cttcacaact gtgttgaaat    2820
tgcctcagca atgggacctc aagtgctccc gggtgcctgt gaaaggctga tcatcagcat    2880
gtctgccaag ctgcatgatg gggctgtggc ctgcaagtgt caccccccagg ctcagtcgg    2940 atccagctgc agccgacttg gaggccagtg ccagtgtaaa cctcttgtgg tcgggcgctg    3000
ctgtgacagg tgctcaactg gaagctatga tttgggggcat cacggctgtc acccatgtca    3060
ctgccatcct caaggatcaa aggacactgt atgtgaccaa gtaacaggac agtgccctg    3120 ccatggagag gtgtctggcc gccgctgtga tcgctgcctg gcaggctact ttggatttcc    3180
cagctgccac ccttgccctt gtaataggtt tgctgaactt tgtgatcctg agacagggtc    3240
atgcttcaat tgtggaggct ttacaactgg cagaaactgt gaaaggtgta ttgatggtta    3300
ctatggaaat ccttcttcag gacagccctg tcgtccttgc ctgtgtccag atgatccctc    3360
aagcaatcag tattttgccc attcctgtta tcagaatctg tggagctcag atgtaatctg    3420
caattgtctt caaggttata cgggtactca gtgtggagaa tgctctactg gttttctatgg    3480 aaatccaaga atttcaggag caccttgcca accatgtgcc tgcaacaaca acatagatgt    3540
aaccgatcca gagtcctgca gccgggtaac aggggagtgc cttcgatgtt gcacaacac    3600 tcagggcgca aactgccagc tctgcaaacc aggtcactat ggatcagccc tcaatcagac    3660
ctgcagaaga tgctcctgcc atgcttccgg cgtgagtccc atggagtgtc ccctggtgg    3720 gggagcttgc ctctgtgacc ctgtcactgg tgcatgtcct tgtctgccga atgtcacagg    3780
cctggcctgt gaccgttgtg ctgatggata ctggaatctg gtccctggca gaggatgtca    3840
gtcatgtgac tgtgacccta ggacctctca aagtagccac tgtgaccagc ttacaggcca    3900
gtgtccgtgt aaattaggtt acggcgggaa acgttgcagt gagtgccagg aaaattatta    3960
tggtgatcca cctgggcgat gcattccatg tgattgtaac agggcaggta cccagaagcc    4020
catctgtgat ccagacacag gcatgtgccg ctgccgggag ggtgtcagcg ccagagatg    4080 tgatcgctgt gcccgggggac acagccagga attcccctact tgtcttcaat gtcacttgtg    4140
ctttgatcag tgggaccaca ccatttcttc cctctccaaa gcggtgcaag ggttaatgag    4200
actggctgct aacatggaag ataaaagaga ccctgcct gtctgtgagg cagacttcaa    4260
agacctcaga gggaacgtgt ctgaaataga aaggatttg aaacatcctg tttcccatc    4320 tgggaaattc ttaaaagtca aggattatca tgactctgtt agaagacaaa tcatgcagct    4380
aaatgaacaa ctgaaagcag tgtatgaatt tcaagatctg aaagatacaa tagaaagagc    4440
aaagaatgaa gcagacctct tacttgaaga ccttcaggaa gaaattgatt tgcaatccag    4500
tgtccttaat gcaagcattg cggactcctc agaaaacatc aagaaatatt atcacatatc    4560
atcatctgct gaaagaaaaa ttaatgaaac tagttccacc attaatacct ctgcaaatac    4620
aaggaatgac ttacttacca tcttagatac actaacctca aaaggaaact tgtcattgga    4680
aagattaaag cagattaaga taccagatat ccaaatattg aatgaaaagg tgtgcgagga    4740
tccaggaaat gtgccatgtg tgcccttgcc ctgtggcggt gctctctgca cgggccggaa    4800
ggggcacagg aagtgtaggg gtcccggctg tcacggctcc ctgacccctct caacgaatgc    4860 cctccaaaaa gcccaggaag caaaatccat tattcgtaat ttggacaaac aggttcgtgg    4920
gttgaaaaat cagatcgaaa gtataagtga acaggcagaa gtctccaaaa acaatgcctt    4980
acagctgagg gaaaaactgg gaaatataag aaaccaaagt gactctgaag aagaaaacat    5040
caatcttttc atcaaaaaag tgaaaaactt tttgttagag gaaaacgtgc ctccagaaga    5100
catcgagaag gttgcgaatg gtgtgcttga cattcaccta ccaattccat cccaaaatct    5160
```

```
aaccgatgaa cttgtcaaaa tacagaaaca tatgcaactc tgtgaggatt acaggacaga    5220
tgaaaacagg ttaaatgaag aagcagatgg agcccaaaag cttttggtga aggccaaagc    5280
agctgagaaa gcagcaaata ttctattaaa tcttgacaaa acattgaacc agttacaaca    5340
agctcaaatc actcaaggac gggcaaactc taccattaca cagctgactg ccaatataac    5400
aaaaataaaa aagaatgtgc tgcaggctga aaatcaaacc agggaaatga agagtgagct    5460
ggagttagca aagcagcgat cagggctgga ggatggactt tccctgctgc agaccaagtt    5520
gcaaaggcat caagaccacg ctgtcaatgc gaaagttcag gctgaatctg cccaacacca    5580
ggctgggagt cttgagaagg aatttgttga gctgaaaaaa caatatgcta ttctccaacg    5640
taagacaagc actacaggac taacaaagga gacattagga aaagttaaac agctaaaaga    5700
tgcggcagaa aaattggctg agatacaga ggccaagata agaagaataa cagatttaga    5760
aaggaaaatc caagatttga atctaagtag acaagcaaaa gctgatcaac tgagaatatt    5820
ggaagatcaa gttgttgcca ttaaaaatga aattgttgaa caagaaaaaa aatatgctag    5880
gtgctatagc ctcgagcacc accatcacca tcaccatcac taagtgatta acctcaggtg    5940
caggctgcct atcagaaggt ggtggctggt gtggccaatg ccctggctca caaataccac    6000
tgagatcgat cttttttccct ctgccaaaaa ttatggggac atcatgaagc cccttgagca    6060
tctgacttct ggctaataaa ggaaatttat tttcattgca atagtgtgtt ggaattttt    6120 gtgtctctca ctcggaagga catatgggag ggcaaatcat ttaaaacatc agaatgagta    6180
tttggtttag agtttggcaa catatgccca tatgtaacta gcataacccc ttggggcctc    6240
taaacgggtc ttgagggggtt ttttgctgaa agcatgcgga ggaaattctc cttgaagttt    6300
ccctggtgtt caaagtaaag gagtttgcac cagacgcacc tctgttcact ggtccggcgt    6360
attaaaacac gatacattgt tattagtaca tttattaagc gctagattct gtgcgttgtt    6420
gatttacaga caattgttgt acgtatttta ataattcatt aaatttataa tctttagggt    6480
ggtatgttag agcgaaaatc aaatgatttt cagcgtcttt atatctgaat ttaaatatta    6540
aatcctcaat agatttgtaa ataggtttc gattagtttc aaacaagggt tgttttttccg    6600 aaccgatggc tggactatct aatggatttt cgctcaacgc cacaaaactt gccaaatctt    6660
gtagcagcaa tctagctttg tcgatattcg tttgtgtttt gttttgtaat aaaggttcga    6720
cgtcgttcaa atatattgc gcttttgtat ttcttttcatc actgtcgtta gtgtacaatt    6780
gactcgacgt aaacacgtta aatagagctt ggacatattt aacatcgggc gtgttagctt    6840
tattaggccg attatcgtcg tcgtcccaac cctcgtcgtt agaagttgct tccgaagacg    6900
attttgccat agccacacga cgcctattaa ttgtgtcggc taacacgtcc gcgatcaaat    6960
ttgtagttga gcttttttgga attatttctg attgcgggcg ttttttgggcg ggtttcaatc    7020 taactgtgcc cgattttaat tcagacaaca cgttagaaag cgatggtgca ggcggtggta    7080
acatttcaga cggcaaatct actaatggcg gcggtggtgg agctgatgat aaatctacca    7140
tcggtggagg cgcaggcggg gctggcggcg gaggcggagg cggaggtggt ggcggtgatg    7200
cagacggcgg tttaggctca aatgtctctt taggcaacac agtcggcacc tcaactattg    7260
tactggtttc gggcgccgtt tttggttga ccggtctgag acgagtgcga ttttttttcgt    7320 ttctaatagc ttccaacaat tgttgtctgt cgtctaaagg tgcagcgggt tgaggttccg    7380
tcggcattgg tggagcgggc ggcaattcag acatcgatgg tggtggtggt ggtggaggcg    7440
ctggaatgtt aggcacggga gaaggtggtg gcggcggtgc cgccggtata atttgttctg    7500
```

-continued

```
gtttagtttg ttcgcgcacg attgtgggca ccggcgcagg cgccgctggc tgcacaacgg      7560
aaggtcgtct gcttcgaggc agcgcttggg gtggtggcaa ttcaatatta taattggaat      7620
acaaatcgta aaaatctgct ataagcattg taatttcgct atcgtttacc gtgccgatat      7680
ttaacaaccg ctcaatgtaa gcaattgtat tgtaaagaga ttgtctcaag ctcggaacgc      7740
tgcgctcggt cgttcggctg cggcgagcgg tatcagctca ctcaaaggcg gtaatacggt      7800
tatccacaga atcaggggat aacgcaggaa agaacatgtg agcaaaaggc cagcaaaagg      7860
ccaggaaccg taaaaaggcc gcgttgctgg cgttttttcca taggctccgc cccctgacg      7920 agcatcacaa aaatcgacgc tcaagtcaga ggtggcgaaa cccgacagga ctataaagat      7980
accaggcgtt tccccctgga agctccctcg tgcgctctcc tgttccgacc ctgccgctta      8040
ccggatacct gtccgccttt ctcccttcgg gaagcgtggc gctttctcaa tgctcacgct      8100
gtaggtatct cagttcggtg taggtcgttc gctccaagct gggctgtgtg cacgaacccc      8160
ccgttcagcc cgaccgctgc gccttatccg gtaactatcg tcttgagtcc aacccggtaa      8220
gacacgactt atcgccactg gcagcagcca ctggtaacag gattagcaga gcgaggtatg      8280
taggcggtgc tacagagttc ttgaagtggt ggcctaacta cggctacact agaaggacag      8340
tatttggtat ctgcgctctg ctgaagccag ttaccttcgg aaaaagagtt ggtagctctt      8400
gatccggcaa acaaaccacc gctggtagcg gtggtttttt tgtttgcaag cagcagatta      8460
cgcgcagaaa aaaaggatct caagaagatc ctttgttacc aatgcttaat cagtgaggca      8520
cctatctcag cgatctgtct atttcgttca tccatagttg cctgactccc cgtcgtgtag      8580
ataactacga tacgggaggg cttaccatct ggccccagtg ctgcaatgat accgcgagac      8640
ccacgctcac cggctccaga tttatcagca ataaaccagc cagccggaag ggccgagcgc      8700
agaagtggtc ctgcaacttt atccgcctcc atccagtcta ttaattgttg ccgggaagct      8760
agagtaagta gttcgccagt taatagtttg cgcaacgttg ttgccattgc tacaggcatc      8820
gtggtgtcac gctcgtcgtt tggtatggct tcattcagct ccggttccca acgatcaagg      8880
cgagttacat gatcccccat gttgtgcaaa aaagcggtta gctccttcgg tcctccgatc      8940
gttgtcagaa gtaagttggc cgcagtgtta tcactcatgg ttatggcagc actgcataat      9000
tctcttactg tcatgccatc cgtaagatgc ttttctgtga ctggtgagta ctcaaccaag      9060
tcattctgag aatagtgtat gcggcgaccg agttgctctt gcccggcgtc aatacgggat      9120
aataccgcgc cacatagcag aactttaaaa gtgctcatca ttggaaaacg ttcttcgggg      9180
cgaaaactct caaggatctt accgctgttg agatccagtt cgatgtaacc cactcgtgca      9240
cccaactgat cttcagcatc ttttactttc accagcgttt ctgggtgagc aaaaacagga      9300
aggcaaaatg ccgcaaaaaa gggaataagg gcgacacgga aatgttgaat actcatactc      9360
ttcctttttc aatattattg aagcatttat cagggttatt gtctcatgtc cgcgcgtttc      9420
ctgcatcttt taatcaaatc ccaagatgtg tataaaccac caaactgcca aaaatgaaaa      9480
actgtcgaca agctctgtcc gtttgctggc aactgcaagg gtctcaatcc tatttgtaat      9540
tattgaataa taaaacaatt ataaatgtca aatttgtttt ttattaacga tacaaaccaa      9600
acgcaacaag aacatttgta gtattatcta taattgaaaa cgcgtagtta taatcgctga      9660
ggtaatattt aaaatcattt tcaaatgatt cacagttaat ttgcgacaat ataatttat      9720 tttcacataa actagacgcc ttgtcgtctt cttcttcgta ttccttctct ttttcatttt      9780
tctcttcata aaaattaaca tagttattat cgtatccata tatgtatcta tcgtatagag      9840 taaattttt gttgtcataa atatatatgt ctttttttaat gggggtgtata gtaccgctgc      9900
```

```
gcatagttttt tctgtaattt acaacagtgc tattttctgg tagttcttcg gagtgtgttg    9960
ctttaattat taaatttata taatcaatga atttgggatc gtcggttttg tacaatatgt   10020
tgccggcata gtacgcagct tcttctagtt caattacacc attttttagc agcaccggat   10080
taacataact ttccaaaatg ttgtacgaac cgttaaacaa aaacagttca cctcccttt    10140 ctatactatt gtctgcgagc agttgtttgt tgttaaaaat aacagccatt gtaatgagac   10200
gcacaaacta atatcacaaa ctggaaatgt ctatcaatat atagttgctc tagttattaa   10260
tagtaatcaa ttacggggtc attagttcat agcccatata tggagttccg cgttacataa   10320
cttacggtaa atggcccgcc tggctgaccg cccaacgacc cccgcccatt gacgtcaata   10380
atgacgtatg ttcccatagt aacgccaata gggactttcc attgacgtca atgggtggac   10440
tatttacggt aaactgccca cttggcagta catcaagtgt atcatatgcc aagtacgccc   10500
cctattgacg tcaatgacgg taaatggccc gcctggcatt atgcccagta catgacctta   10560
tgggactttc ctacttggca gtacatctac gtattagtca tcgctattac catgcatggt   10620
cgaggtgagc cccacgttct gcttcactct ccccatctcc cccccctccc cacccccaat   10680
tttgtattta tttattttt  aattattttg tgcagcgatg ggggcggggg gggggggggg   10740
gcgcgcgcca ggcggggcgg ggcggggcga ggggcggggc ggggcgaggc ggagaggtgc   10800
ggcggcagcc aatcagagcg gcgcgctccg aaagtttcct tttatggcga ggcggcggcg   10860
gcggcggccc tataaaaagc gaagcgcgcg gcgggcg                            10897
```

<210> SEQ ID NO 6  
<211> LENGTH: 10900  
<212> TYPE: DNA  
<213> ORGANISM: Artificial Sequence  
<220> FEATURE:  
<223> OTHER INFORMATION: pTriEx-1-LAMB4(IF1)[human](dHis)

<400> SEQUENCE: 6

```
ggagtcgctg cgacgctgcc ttcgccccgt gccccgctcc gccgccgcct cgcgccgccc     60
gccccggctc tgactgaccg cgttactccc acaggtgagc gggcgggacg gcccttctcc    120
ttcgggctgt aattagcgct tggtttaatg acggcttgtt tcttttctgt ggctgcgtga    180
aagccttgag gggctccggg agggcccttt gtgcgggggg agcggctcgg ggctgtccgc    240 gggggacgg ctgccttcgg ggggacggg gcagggcggg gttcggcttc tggcgtgtga    300
ccggcggctc tagagcctct gctaaccatg ttcatgcctt cttcttttc ctacagctcc    360 tgggcaacgt gctggttatt gtgctgtctc atcattttgg caaagaattg gatcggaccg    420
aaattaatac gactcactat aggggaattg tgagcggata caattcccc ggagttaatc    480 cgggaccttt aattcaaccc aacacaatat attatagtta ataagaatt attatcaaat    540 catttgtata ttaattaaaa tactatactg taaattacat tttatttaca atcaaaggag    600
atataccatg caatttcaac tgacccttt tttgcacctt gggtggctca gttactcaaa    660
agctcaagat gactgcaaca ggggtgcctg tcatcccacc actggtgatc tcctggtggg    720
caggaacacg cagcttatgg cttcttctac ctgtgggctg agcagagccc agaaatactg    780
catcctcagt tacctggagg gggaacaaaa atgcttcatc tgtgactcta gatttccata    840
tgatccgtat gaccaaccca acagccacac cattgagaat gtcattgtaa gttttgaacc    900
agacagagaa aagaaatggt ggcaatctga aaatggtctt gatcatgtca gcatcagact    960
ggacttagag gcattatttc ggttcagcca ccttatcctg acctttaaga cttttcggcc   1020
```

```
tgctgcaatg ttagttgaac gttccacaga ctatggacac aactggaaag tgttcaaata    1080
ttttgcaaaa gactgtgcca cttcctttcc taacatcaca tctggccagg cccagggagt    1140
gggagacatt gtttgtgact ccaaatactc ggatattgaa ccctcaacag gtggagaggt    1200
tgttttaaaa gttttggatc ccagttttga aattgaaaac ccttatagcc cctacatcca    1260
agaccttgtg acattgacaa acctgaggat aaactttacc aagctccaca cccttgggga    1320
tgctttgctt ggaaggaggc aaaatgattc ccttgataaa tactactatg ctctgtacga    1380
gatgattgtt cggggaagct gcttttgcaa tggccatgct agcgaatgtc gccctatgca    1440
gaagatgcgg ggagatgttt tcagccctcc tggaatggtt cacggtcagt gtgtgtgtca    1500
gcacaataca gatggtccga actgtgagag atgcaaggac ttcttccagg atgctccttg    1560
gaggccagct gcagacctcc aggacaacgc ttgcagatcg tgcagctgta acagccactc    1620
cagccgctgt cactttgaca tgactacgta cctggcaagc ggtggcctca gcggggggcgt    1680 gtgtgaagac tgccagcaca acactgaggg gcagcactgc gaccgctgca gaccctctt    1740 ctacagggac ccgctcaaga ccatctcaga tccctacgcg tgcattcctt gtgaatgtga    1800
ccccgatggg accatatctg gtggcatttg tgtgagccac tctgatcctg ccttagggtc    1860
tgtggctggc cagtgccttt gtaaagaaa cgtgaagga gccaaatgcg accagtgcaa    1920
acccaaccac tatggactaa gcgccaccga ccccctgggc tgccagccct gcgactgtaa    1980 ccccccttggg agtctgccat tcttgacctg tgatgtggat acaggccaat gcttgtgcct    2040
gtcatatgtc accggagcac actgcgaaga atgcactgtt ggatactggg gcctgggaaa    2100
tcatctccat gggtgttctc cctgtgactg tgatattgga ggtgcttatt ctaacgtgtg    2160
ctcacccaag aatgggcagt gtgaatgccg cccacatgtc actggccgta gctgctctga    2220 accagccct ggctacttct ttgctccttt gaatttctat ctctacgagg cagaggaagc    2280
cacaacactc caaggactgg cgcctttggg ctcggagacg tttggccaga gtcctgctgt    2340
tcacgttgtt ttaggagagc cagttcctgg gaaccctgtt acatggactg gacctggatt    2400
tgccagggtt ctccctgggg ctggcttgag atttgctgtc aacaacattc cctttcctgt    2460
ggacttcacc attgccattc actatgaaac ccagtctgca gctgactgga ctgtccagat    2520
tgtggtgaac ccccctggag ggagtgagca ctgcataccc aagactctac agtcaaagcc    2580
tcagtctttt gccttaccag cggctacgag aatcatgctg cttcccacac ccatctgttt    2640
agaaccagat gtacaatatt ccatagatgt ctattttct cagcctttgc aaggagagtc    2700
ccacgctcat tcacatgtcc tggtggactc tcttggcctt attccccaaa tcaattcatt    2760
ggagaatttc tgcagcaagc aggacttaga tgagtatcag cttcacaact gtgttgaaat    2820
tgcctcagca atgggacctc aagtgctccc gggtgcctgt gaaaggctga tcatcagcat    2880
gtctgccaag ctgcatgatg gggctgtggc ctgcaagtgt caccccagg gctcagtcgg    2940 atccagctgc agccgacttg gaggccagtc ccagtgtaaa cctcttgtgg tcgggcgctg    3000
ctgtgacagg tgctcaactg gaagctatga tttggggcat cacggctgtc acccatgtca    3060
ctgccatcct caaggatcaa aggacactgt atgtgaccaa gtaacaggac agtgcccctg    3120
ccatggagag gtgtctggcc gccgctgtga tcgctgcctg caggctact ttggatttcc    3180 cagctgccac ccttgccctt gtaataggtt tgctgaactt tgtgatcctg agacagggtc    3240
atgcttcaat gtggaggct ttacaactgg cagaaactgt gaaaggtgta ttgatggtta    3300
ctatggaaat ccttcttcag gacagccctg tcgtccttgc ctgtgtccag atgatccctc    3360
aagcaatcag tattttgccc attcctgtta tcagaatctg tggagctcag atgtaatctg    3420
```

```
caattgtctt caaggttata cgggtactca gtgtggagaa tgctctactg gtttctatgg   3480
aaatccaaga atttcaggag caccttgcca accatgtgcc tgcaacaaca acatagatgt   3540
aaccgatcca gagtcctgca gccgggtaac aggggagtgc cttcgatgtt tgcacaacac   3600
tcagggcgca aactgccagc tctgcaaacc aggtcactat ggatcagccc tcaatcagac   3660
ctgcagaaga tgctcctgcc atgcttccgg cgtgagtccc atggagtgtc ccctggtgg   3720 gggagcttgc ctctgtgacc ctgtcactgg tgcatgtcct tgtctgccga atgtcacagg   3780
cctggcctgt gaccgttgtg ctgatggata ctggaatctg gtccctggca gaggatgtca   3840
gtcatgtgac tgtgacccta ggacctctca agtagccac tgtgaccagc ttacaggcca   3900
gtgtccgtgt aaattaggtt acggcgggaa acgttgcagt gagtgccagg aaaattatta   3960
tggtgatcca cctgggcgat gcattccatg tgattgtaac agggcaggta cccagaagcc   4020
catctgtgat ccagacacag gcatgtgccg ctgccgggag ggtgtcagcg ccagagatg   4080 tgatcgctgt gcccggggac acagccagga attccctact tgtcttcaat gtcacttgtg   4140
ctttgatcag tgggaccaca ccatttcttc cctctccaaa gcggtgcaag ggttaatgag   4200
actggctgct aacatggaag ataaaagaga ccctgcct gtctgtgagg cagacttcaa   4260
agacctcaga gggaacgtgt ctgaaataga aaggattttg aaacatcctg ttttcccatc   4320
tgggaaattc ttaaaagtca aggattatca tgactctgtt agaagacaaa tcatgcagct   4380
aaatgaacaa ctgaaagcag tgtatgaatt tcaagatctg aaagatacaa tagaaagagc   4440
aaagaatgaa gcagacctct tacttgaaga ccttcaggaa gaaattgatt tgcaatccag   4500
tgtccttaat gcaagcattg cggactcctc agaaaacatc aagaaatatt atcacatatc   4560
atcatctgct gaaaagaaaa ttaatgaaac tagttccacc attaatacct ctgcaaatac   4620
aaggaatgac ttacttacca tcttagatac actaacctca aaaggaaact tgtcattgga   4680
aagattaaag cagattaaga taccagatat ccaaatattg aatgaaaagg tgtgcggaga   4740
tccaggaaat gtgccatgtg tgcccttgcc ctgtggcggt gctctctgca cgggccggaa   4800
ggggcacagg aagtgtaggg gtcccggctg tcacggctcc ctgaccctct caacgaatgc   4860
cctccaaaaa gcccaggaag caaaatccat tattcgtaat ttggacaaac aggttcgtgg   4920
gttgaaaaat cagatcgaaa gtataagtga acaggcagaa gtctccaaaa acaatgcctt   4980
acagctgagg gaaaaactgg gaaatataag aaaccaaagt gactctgaag aagaaaacat   5040
caatcttttc atcaaaaaag tgaaaaactt tttgttagag gaaaacgtgc ctccagaaga   5100
catcgagaag gttgcgaatg gtgtgcttga cattcaccta ccaattccat cccaaaatct   5160
aaccgatgaa cttgtcaaaa tacagaaaca tatgcaactc tgtgaggatt acaggacaga   5220
tgaaaacagg ttaaatgaag aagcagatgg agcccaaaag cttttggtga aggccaaagc   5280
agctgagaaa gcagcaaata ttctattaaa tcttgacaaa acattgaacc agttacaaca   5340
agctcaaatc actcaaggac gggcaaactc taccattaca cagctgactg ccaatataac   5400
aaaaataaaa aagaatgtgc tgcaggctga aaatcaaacc agggaaatga agagtgagct   5460
ggagttagca aagcagcgat cagggctgga ggatggactt tccctgctgc agaccaagtt   5520
gcaaaggcat caagaccacg ctgtcaatgc gaaagttcag gctgaatctg cccaacacca   5580
ggctgggagt cttgagaagg aatttgttga gctgaaaaaa caatatgcta ttctccaacg   5640
taagacaagc actacaggac taacaaagga gacattagga aaagttaaac agctaaaaga   5700
tgcggcagaa aaattggctg gagatacaga ggccaagata agaagaataa cagatttaga   5760
```

```
aaggaaaatc caagatttga atctaagtag acaagcaaaa gctgatcaac tgagaatatt   5820
ggaagatcaa gttgttgcca ttaaaaatga aattgttgaa caagaaaaaa atatgctag    5880
gtgctatagc tagctcgagc accaccatca ccatcaccat cactaagtga ttaacctcag   5940
gtgcaggctg cctatcagaa ggtggtggct ggtgtggcca atgccctggc tcacaaatac   6000
cactgagatc gatcttttc cctctgccaa aaattatggg gacatcatga agccccttga    6060
gcatctgact tctggctaat aaaggaaatt tattttcatt gcaatagtgt gttggaattt   6120
tttgtgtctc tcactcggaa ggacatatgg gagggcaaat catttaaaac atcagaatga   6180
gtatttggtt tagagtttgg caacatatgc ccatatgtaa ctagcataac cccttggggc   6240
ctctaaacgg gtcttgaggg gttttttgct gaaagcatgc ggaggaaatt ctccttgaag   6300
tttccctggt gttcaaagta aaggagtttg caccagacgc acctctgttc actggtccgg   6360
cgtattaaaa cacgatacat tgttattagt acatttatta agcgctagat tctgtgcgtt   6420
gttgatttac agacaattgt tgtacgtatt ttaataattc attaaattta taatctttag   6480
ggtggtatgt tagagcgaaa atcaaatgat tttcagcgtc tttatatctg aatttaaata   6540
ttaaatcctc aatagatttg taaaataggt ttcgattagt ttcaaacaag gttgttttt    6600
ccgaaccgat ggctggacta tctaatggat tttcgctcaa cgccacaaaa cttgccaaat   6660
cttgtagcag caatctagct ttgtcgatat tcgtttgtgt tttgttttgt aataaaggtt   6720
cgacgtcgtt caaaatatta tgcgcttttg tatttctttc atcactgtcg ttagtgtaca   6780
attgactcga cgtaaacacg ttaaatagag cttggacata tttaacatcg ggcgtgttag   6840
ctttattagg ccgattatcg tcgtcgtccc aaccctcgtc gttagaagtt gcttccgaag   6900
acgattttgc catagccaca cgacgcctat taattgtgtc ggctaacacg tccgcgatca   6960
aatttgtagt tgagcttttt ggaattattt ctgattgcgg gcgttttttgg gcgggtttca   7020
atctaactgt gcccgatttt aattcagaca acacgttaga aagcgatggt gcaggcggtg   7080
gtaacatttc agacggcaaa tctactaatg gcggcggtgg tggagctgat gataaatcta   7140
ccatcggtgg aggcgcaggc ggggctggcg gcggaggcgg aggcggaggt ggtggcggtg   7200
atgcagacgg cggtttaggc tcaaatgtct ctttaggcaa cacagtcggc acctcaacta   7260
ttgtactggt ttcgggcgcc gtttttggtt tgaccggtct gagacgagtg cgattttttt   7320
cgtttctaat agcttccaac aattgttgtc tgtcgtctaa aggtgcagcg ggttgaggtt   7380
ccgtcggcat tggtggagcg ggcggcaatt cagacatcga tggtggtggt ggtggtggag   7440
gcgctggaat gttaggcacg ggagaaggtg gtggcggcgg tgccgccggt ataatttgtt   7500
ctggtttagt ttgttcgcgc acgattgtgg gcaccggcgc aggcgccgct ggctgcacaa   7560
cggaaggtcg tctgcttcga ggcagcgctt ggggtggtgg caattcaata ttataattgg   7620
aatacaaatc gtaaaaatct gctataagca ttgtaatttc gctatcgttt accgtgccga   7680
tatttaacaa ccgctcaatg taagcaattg tattgtaaag agattgtctc aagctcggaa   7740
cgctgcgctc ggtcgttcgg ctgcggcgag cggtatcagc tcactcaaag gcggtaatac   7800
ggttatccac agaatcaggg gataacgcag gaaagaacat gtgagcaaaa ggccagcaaa   7860
aggccaggaa ccgtaaaaag gccgcgttgc tggcgttttt ccataggctc cgccccctg    7920
acgagcatca caaaaatcga cgctcaagtc agaggtggcg aaacccgaca ggactataaa   7980
gataccaggc gtttccccct ggaagctccc tcgtgcgctc tcctgttccg accctgccgc   8040
ttaccggata cctgtccgcc tttctccctt cgggaagcgt ggcgctttct caatgctcac   8100
gctgtaggta tctcagttcg gtgtaggtcg ttcgctccaa gctgggctgt gtgcacgaac   8160
```

```
cccccgttca gcccgaccgc tgcgccttat ccggtaacta tcgtcttgag tccaacccgg   8220
taagacacga cttatcgcca ctggcagcag ccactggtaa caggattagc agagcgaggt   8280
atgtaggcgg tgctacagag ttcttgaagt ggtggcctaa ctacggctac actagaagga   8340
cagtatttgg tatctgcgct ctgctgaagc cagttacctt cggaaaaaga gttggtagct   8400
cttgatccgg caaacaaacc accgctggta gcggtggttt ttttgtttgc aagcagcaga   8460
ttacgcgcag aaaaaaagga tctcaagaag atcctttgtt accaatgctt aatcagtgag   8520
gcacctatct cagcgatctg tctatttcgt tcatccatag ttgcctgact ccccgtcgtg   8580
tagataacta cgatacggga gggcttacca tctggcccca gtgctgcaat gataccgcga   8640
gacccacgct caccggctcc agatttatca gcaataaacc agccagccgg aagggccgag   8700
cgcagaagtg gtcctgcaac tttatccgcc tccatccagt ctattaattg ttgccgggaa   8760
gctagagtaa gtagttcgcc agttaatagt ttgcgcaacg ttgttgccat tgctacaggc   8820
atcgtggtgt cacgctcgtc gtttggtatg gcttcattca gctccggttc caacgatca   8880 aggcgagtta catgatcccc catgttgtgc aaaaaagcgg ttagctcctt cggtcctccg   8940
atcgttgtca gaagtaagtt ggccgcagtg ttatcactca tggttatggc agcactgcat   9000
aattctctta ctgtcatgcc atccgtaaga tgcttttctg tgactggtga gtactcaacc   9060
aagtcattct gagaatagtg tatgcggcga ccgagttgct cttgcccggc gtcaatacgg   9120
gataataccg cgccacatag cagaacttta aaagtgctca tcattggaaa acgttcttcg   9180
gggcgaaaac tctcaaggat cttaccgctg ttgagatcca gttcgatgta acccactcgt   9240
gcacccaact gatcttcagc atcttttact ttcaccagcg tttctgggtg agcaaaaaca   9300
ggaaggcaaa atgccgcaaa aaagggaata agggcgacac ggaaatgttg aatactcata   9360
ctcttccttt ttcaatatta ttgaagcatt tatcagggtt attgtctcat gtccgcgcgt   9420
ttcctgcatc ttttaatcaa atcccaagat gtgtataaac caccaaactg ccaaaaaatg   9480
aaaactgtcg acaagctctg tccgtttgct ggcaactgca agggtctcaa tcctatttgt   9540
aattattgaa taataaaaca attataaatg tcaaatttgt tttttattaa cgatacaaac   9600
caaacgcaac aagaacattt gtagtattat ctataattga aaacgcgtag ttataatcgc   9660
tgaggtaata tttaaaatca ttttcaaatg attcacagtt aatttgcgac aatataattt   9720
tattttcaca taaactagac gccttgtcgt cttcttcttc gtattccttc tcttttttcat   9780 ttttctcttc ataaaaatta acatagttat tatcgtatcc atatatgtat ctatcgtata   9840
gagtaaattt tttgttgtca taaatatata tgtcttttt aatggggtgt atagtaccgc   9900
tgcgcatagt ttttctgtaa tttacaacag tgctattttc tggtagttct tcggagtgtg   9960
ttgctttaat tattaaattt atataatcaa tgaatttggg atcgtcggtt ttgtacaata  10020
tgttgccggc atagtacgca gcttcttcta gttcaattac accattttt agcagcaccg  10080 gattaacata actttccaaa atgttgtacg aaccgttaaa caaaaacagt tcacctccct  10140
tttctatact attgtctgcg agcagttgtt tgttgttaaa ataacagcc attgtaatga  10200 gacgcacaaa ctaatatcac aaactggaaa tgtctatcaa tatatagttg ctctagttat  10260
taatagtaat caattacggg gtcattagtt catagcccat atatggagtt ccgcgttaca  10320
taacttacgg taaatggccc gcctggctga ccgcccaacg acccccgccc attgacgtca  10380
ataatgacgt atgttcccat agtaacgcca tagggactt ccattgacg tcaatgggtg  10440 gactatttac ggtaaactgc ccacttggca gtacatcaag tgtatcatat gccaagtacg  10500
```

-continued

```
cccctattg acgtcaatga cggtaaatgg cccgcctggc attatgccca gtacatgacc    10560
ttatgggact ttcctacttg gcagtacatc tacgtattag tcatcgctat taccatgcat    10620
ggtcgaggtg agccccacgt tctgcttcac tctccccatc tccccccct ccccacccc      10680 aattttgtat ttatttattt tttaattatt ttgtgcagcg atggggcgg gggggggg        10740 gggcgcgcg ccaggcgggg cggggcgggg cgagggcgg ggcggggcga ggcggagagg      10800
tgcggcggca gccaatcaga gcggcgcgct ccgaaagttt ccttttatgg cgaggcggcg    10860
gcggcggcgg ccctataaaa agcgaagcgc gcggcgggcg                           10900
```

<210> SEQ ID NO 7
<211> LENGTH: 1771
<212> TYPE: PRT
<213> ORGANISM: Artificial Sequence
<220> FEATURE:
<223> OTHER INFORMATION: LAMB4-His

<400> SEQUENCE: 7

```
Met Gln Phe Gln Leu Thr Leu Phe Leu His Leu Gly Trp Leu Ser Tyr
 1               5                  10                  15

Ser Lys Ala Gln Asp Asp Cys Asn Arg Gly Ala Cys His Pro Thr Thr
            20                  25                  30

Gly Asp Leu Leu Val Gly Arg Asn Thr Gln Leu Met Ala Ser Ser Thr
        35                  40                  45

Cys Gly Leu Ser Arg Ala Gln Lys Tyr Cys Ile Leu Ser Tyr Leu Glu
    50                  55                  60

Gly Glu Gln Lys Cys Phe Ile Cys Asp Ser Arg Phe Pro Tyr Asp Pro
65                  70                  75                  80

Tyr Asp Gln Pro Asn Ser His Thr Ile Glu Asn Val Ile Val Ser Phe
                85                  90                  95

Glu Pro Asp Arg Glu Lys Lys Trp Trp Gln Ser Glu Asn Gly Leu Asp
           100                 105                 110

His Val Ser Ile Arg Leu Asp Leu Glu Ala Leu Phe Arg Phe Ser His
       115                 120                 125

Leu Ile Leu Thr Phe Lys Thr Phe Arg Pro Ala Ala Met Leu Val Glu
   130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
        195                 200                 205

Ile Glu Asn Pro Tyr Ser Pro Tyr Ile Gln Asp Leu Val Thr Leu Thr
    210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Ala Leu
                245                 250                 255

Tyr Glu Met Ile Val Arg Gly Ser Cys Phe Cys Asn His Ala Ser
            260                 265                 270

Glu Cys Arg Pro Met Gln Lys Met Arg Gly Asp Val Phe Ser Pro Pro
        275                 280                 285

Gly Met Val His Gly Gln Cys Val Cys Gln His Asn Thr Asp Gly Pro
```

```
                290                 295                 300
Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
                325                 330                 335

His Ser Ser Arg Cys His Phe Asp Met Thr Thr Tyr Leu Ala Ser Gly
                340                 345                 350

Gly Leu Ser Gly Gly Val Cys Glu Asp Cys Gln His Asn Thr Glu Gly
                355                 360                 365

Gln His Cys Asp Arg Cys Arg Pro Leu Phe Tyr Arg Asp Pro Leu Lys
                370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
                405                 410                 415

Gly Ser Val Ala Gly Gln Cys Leu Cys Lys Glu Asn Val Glu Gly Ala
                420                 425                 430

Lys Cys Asp Gln Cys Lys Pro Asn His Tyr Gly Leu Ser Ala Thr Asp
                435                 440                 445

Pro Leu Gly Cys Gln Pro Cys Asp Cys Asn Pro Leu Gly Ser Leu Pro
                450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
                485                 490                 495

Gly Asn His Leu His Gly Cys Ser Pro Cys Asp Cys Asp Ile Gly Gly
                500                 505                 510

Ala Tyr Ser Asn Val Cys Ser Pro Lys Asn Gly Gln Cys Glu Cys Arg
                515                 520                 525

Pro His Val Thr Gly Arg Ser Cys Ser Glu Pro Ala Pro Gly Tyr Phe
                530                 535                 540

Phe Ala Pro Leu Asn Phe Tyr Leu Tyr Glu Ala Glu Glu Ala Thr Thr
545                 550                 555                 560

Leu Gln Gly Leu Ala Pro Leu Gly Ser Glu Thr Phe Gly Gln Ser Pro
                565                 570                 575

Ala Val His Val Val Leu Gly Glu Pro Val Pro Gly Asn Pro Val Thr
                580                 585                 590

Trp Thr Gly Pro Gly Phe Ala Arg Val Leu Pro Gly Ala Gly Leu Arg
                595                 600                 605

Phe Ala Val Asn Asn Ile Pro Phe Pro Val Asp Phe Thr Ile Ala Ile
                610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
                645                 650                 655

Lys Pro Gln Ser Phe Ala Leu Pro Ala Ala Thr Arg Ile Met Leu Leu
                660                 665                 670

Pro Thr Pro Ile Cys Leu Glu Pro Asp Val Gln Tyr Ser Ile Asp Val
                675                 680                 685

Tyr Phe Ser Gln Pro Leu Gln Gly Glu Ser His Ala His Ser His Val
                690                 695                 700

Leu Val Asp Ser Leu Gly Leu Ile Pro Gln Ile Asn Ser Leu Glu Asn
705                 710                 715                 720
```

-continued

Phe Cys Ser Lys Gln Asp Leu Asp Glu Tyr Gln Leu His Asn Cys Val
            725                 730                 735

Glu Ile Ala Ser Ala Met Gly Pro Gln Val Leu Pro Gly Ala Cys Glu
            740                 745                 750

Arg Leu Ile Ile Ser Met Ser Ala Lys Leu His Asp Gly Ala Val Ala
            755                 760                 765

Cys Lys Cys His Pro Gln Gly Ser Val Gly Ser Ser Cys Ser Arg Leu
            770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
            805                 810                 815

Cys His Cys His Pro Gln Gly Ser Lys Asp Thr Val Cys Asp Gln Val
            820                 825                 830

Thr Gly Gln Cys Pro Cys His Gly Glu Val Ser Gly Arg Arg Cys Asp
            835                 840                 845

Arg Cys Leu Ala Gly Tyr Phe Gly Phe Pro Ser Cys His Pro Cys Pro
            850                 855                 860

Cys Asn Arg Phe Ala Glu Leu Cys Asp Pro Glu Thr Gly Ser Cys Phe
865                 870                 875                 880

Asn Cys Gly Gly Phe Thr Thr Gly Arg Asn Cys Glu Arg Cys Ile Asp
            885                 890                 895

Gly Tyr Tyr Gly Asn Pro Ser Ser Gly Gln Pro Cys Arg Pro Cys Leu
            900                 905                 910

Cys Pro Asp Asp Pro Ser Ser Asn Gln Tyr Phe Ala His Ser Cys Tyr
            915                 920                 925

Gln Asn Leu Trp Ser Ser Asp Val Ile Cys Asn Cys Leu Gln Gly Tyr
            930                 935                 940

Thr Gly Thr Gln Cys Gly Glu Cys Ser Thr Gly Phe Tyr Gly Asn Pro
945                 950                 955                 960

Arg Ile Ser Gly Ala Pro Cys Gln Pro Cys Ala Cys Asn Asn Asn Ile
            965                 970                 975

Asp Val Thr Asp Pro Glu Ser Cys Ser Arg Val Thr Gly Glu Cys Leu
            980                 985                 990

Arg Cys Leu His Asn Thr Gln Gly Ala Asn Cys Gln Leu Cys Lys Pro
            995                 1000                1005

Gly His Tyr Gly Ser Ala Leu Asn Gln Thr Cys Arg Arg Cys Ser
            1010                1015                1020

Cys His Ala Ser Gly Val Ser Pro Met Glu Cys Pro Pro Gly Gly
            1025                1030                1035

Gly Ala Cys Leu Cys Asp Pro Val Thr Gly Ala Cys Pro Cys Leu
            1040                1045                1050

Pro Asn Val Thr Gly Leu Ala Cys Asp Arg Cys Ala Asp Gly Tyr
            1055                1060                1065

Trp Asn Leu Val Pro Gly Arg Gly Cys Gln Ser Cys Asp Cys Asp
            1070                1075                1080

Pro Arg Thr Ser Gln Ser Ser His Cys Asp Gln Leu Thr Gly Gln
            1085                1090                1095

Cys Pro Cys Lys Leu Gly Tyr Gly Gly Lys Arg Cys Ser Glu Cys
            1100                1105                1110

Gln Glu Asn Tyr Tyr Gly Asp Pro Pro Gly Arg Cys Ile Pro Cys
            1115                1120                1125

```
Asp Cys Asn Arg Ala Gly Thr Gln Lys Pro Ile Cys Asp Pro Asp
1130                    1135                1140

Thr Gly Met Cys Arg Cys Arg Glu Gly Val Ser Gly Gln Arg Cys
1145                    1150                1155

Asp Arg Cys Ala Arg Gly His Ser Gln Glu Phe Pro Thr Cys Leu
1160                    1165                1170

Gln Cys His Leu Cys Phe Asp Gln Trp Asp His Thr Ile Ser Ser
1175                    1180                1185

Leu Ser Lys Ala Val Gln Gly Leu Met Arg Leu Ala Ala Asn Met
1190                    1195                1200

Glu Asp Lys Arg Glu Thr Leu Pro Val Cys Glu Ala Asp Phe Lys
1205                    1210                1215

Asp Leu Arg Gly Asn Val Ser Glu Ile Glu Arg Ile Leu Lys His
1220                    1225                1230

Pro Val Phe Pro Ser Gly Lys Phe Leu Lys Val Lys Asp Tyr His
1235                    1240                1245

Asp Ser Val Arg Arg Gln Ile Met Gln Leu Asn Glu Gln Leu Lys
1250                    1255                1260

Ala Val Tyr Glu Phe Gln Asp Leu Lys Asp Thr Ile Glu Arg Ala
1265                    1270                1275

Lys Asn Glu Ala Asp Leu Leu Leu Glu Asp Leu Gln Glu Glu Ile
1280                    1285                1290

Asp Leu Gln Ser Ser Val Leu Asn Ala Ser Ile Ala Asp Ser Ser
1295                    1300                1305

Glu Asn Ile Lys Lys Tyr Tyr His Ile Ser Ser Ser Ala Glu Lys
1310                    1315                1320

Lys Ile Asn Glu Thr Ser Ser Thr Ile Asn Thr Ser Ala Asn Thr
1325                    1330                1335

Arg Asn Asp Leu Leu Thr Ile Leu Asp Thr Leu Thr Ser Lys Gly
1340                    1345                1350

Asn Leu Ser Leu Glu Arg Leu Lys Gln Ile Lys Ile Pro Asp Ile
1355                    1360                1365

Gln Ile Leu Asn Glu Lys Val Cys Gly Asp Pro Gly Asn Val Pro
1370                    1375                1380

Cys Val Pro Leu Pro Cys Gly Gly Ala Leu Cys Thr Gly Arg Lys
1385                    1390                1395

Gly His Arg Lys Cys Arg Gly Pro Gly Cys His Gly Ser Leu Thr
1400                    1405                1410

Leu Ser Thr Asn Ala Leu Gln Lys Ala Gln Glu Ala Lys Ser Ile
1415                    1420                1425

Ile Arg Asn Leu Asp Lys Val Arg Gly Leu Lys Asn Gln Ile
1430                    1435                1440

Glu Ser Ile Ser Glu Gln Ala Glu Val Ser Lys Asn Asn Ala Leu
1445                    1450                1455

Gln Leu Arg Glu Lys Leu Gly Asn Ile Arg Asn Gln Ser Asp Ser
1460                    1465                1470

Glu Glu Glu Asn Ile Asn Leu Phe Ile Lys Lys Val Lys Asn Phe
1475                    1480                1485

Leu Leu Glu Glu Asn Val Pro Pro Glu Asp Ile Glu Lys Val Ala
1490                    1495                1500

Asn Gly Val Leu Asp Ile His Leu Pro Ile Pro Ser Gln Asn Leu
1505                    1510                1515

Thr Asp Glu Leu Val Lys Ile Gln Lys His Met Gln Leu Cys Glu
```

```
        1520                1525                1530

Asp Tyr Arg Thr Asp Glu Asn Arg Leu Asn Glu Ala Asp Gly
        1535                1540                1545

Ala Gln Lys Leu Leu Val Lys Ala Lys Ala Ala Glu Lys Ala Ala
        1550                1555                1560

Asn Ile Leu Leu Asn Leu Asp Lys Thr Leu Asn Gln Leu Gln Gln
        1565                1570                1575

Ala Gln Ile Thr Gln Gly Arg Ala Asn Ser Thr Ile Thr Gln Leu
        1580                1585                1590

Thr Ala Asn Ile Thr Lys Ile Lys Lys Asn Val Leu Gln Ala Glu
        1595                1600                1605

Asn Gln Thr Arg Glu Met Lys Ser Glu Leu Glu Leu Ala Lys Gln
        1610                1615                1620

Arg Ser Gly Leu Glu Asp Gly Leu Ser Leu Leu Gln Thr Lys Leu
        1625                1630                1635

Gln Arg His Gln Asp His Ala Val Asn Ala Lys Val Gln Ala Glu
        1640                1645                1650

Ser Ala Gln His Gln Ala Gly Ser Leu Glu Lys Glu Phe Val Glu
        1655                1660                1665

Leu Lys Lys Gln Tyr Ala Ile Leu Gln Arg Lys Thr Ser Thr Thr
        1670                1675                1680

Gly Leu Thr Lys Glu Thr Leu Gly Lys Val Lys Gln Leu Lys Asp
        1685                1690                1695

Ala Ala Glu Lys Leu Ala Gly Asp Thr Glu Ala Lys Ile Arg Arg
        1700                1705                1710

Ile Thr Asp Leu Glu Arg Lys Ile Gln Asp Leu Asn Leu Ser Arg
        1715                1720                1725

Gln Ala Lys Ala Asp Gln Leu Arg Ile Leu Glu Asp Gln Val Val
        1730                1735                1740

Ala Ile Lys Asn Glu Ile Val Glu Gln Glu Lys Lys Tyr Ala Arg
        1745                1750                1755

Cys Tyr Ser Leu Glu His His His His His His His
        1760                1765                1770

<210> SEQ ID NO 8
<211> LENGTH: 5
<212> TYPE: PRT
<213> ORGANISM: Artificial Sequence
<220> FEATURE:
<223> OTHER INFORMATION: Autoantibody epitope 1

<400> SEQUENCE: 8

Glu Phe Gln Asp Leu
1               5

<210> SEQ ID NO 9
<211> LENGTH: 10
<212> TYPE: PRT
<213> ORGANISM: Artificial Sequence
<220> FEATURE:
<223> OTHER INFORMATION: Autoantibody epitope 2

<400> SEQUENCE: 9

Ala Asp Leu Leu Leu Glu Asp Leu Gln Glu
1               5                   10

<210> SEQ ID NO 10
<211> LENGTH: 16
```

```
<212> TYPE: PRT
<213> ORGANISM: Artificial Sequence
<220> FEATURE:
<223> OTHER INFORMATION: Autoantibody epitope 3

<400> SEQUENCE: 10

Ala Asp Leu Leu Leu Glu Asp Leu Gln Glu Glu Ile Asp Leu Gln Ser
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Autoantibody epitope 4

<400> SEQUENCE: 11

Asp Leu Leu Thr Ile Leu Asp Thr Leu Thr Ser Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Autoantibody epitope 5

<400> SEQUENCE: 12

Gln Ile Lys Ile Pro Asp Ile Gln Ile Leu Asn Glu Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Autoantibody epitope 6

<400> SEQUENCE: 13

Val Arg Gly Leu Lys Asn Gln Ile Glu Ser Ile Ser Glu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Autoantibody epitope 7

<400> SEQUENCE: 14

Leu Leu Glu Glu Asn Val Pro Pro Glu Asp Ile
1               5                   10

<210> SEQ ID NO 15
<211> LENGTH: 300
<212> TYPE: PRT
<213> ORGANISM: Artificial Sequence
<220> FEATURE:
<223> OTHER INFORMATION: Subfragment 1

<400> SEQUENCE: 15

Met Gln Asp Asp Cys Asn Arg Gly Ala Cys His Pro Thr Thr Gly Asp
1               5                   10                  15

Leu Leu Val Gly Arg Asn Thr Gln Leu Met Ala Ser Ser Thr Cys Gly
                20                  25                  30

Leu Ser Arg Ala Gln Lys Tyr Cys Ile Leu Ser Tyr Leu Glu Gly Glu
```

```
                35                  40                  45
Gln Lys Cys Phe Ile Cys Asp Ser Arg Phe Pro Tyr Asp Pro Tyr Asp
 50                  55                  60

Gln Pro Asn Ser His Thr Ile Glu Asn Val Ile Val Ser Phe Glu Pro
65                  70                  75                  80

Asp Arg Glu Lys Lys Trp Trp Gln Ser Glu Asn Gly Leu Asp His Val
                85                  90                  95

Ser Ile Arg Leu Asp Leu Glu Ala Leu Phe Arg Phe Ser His Leu Ile
            100                 105                 110

Leu Thr Phe Lys Thr Phe Arg Pro Ala Ala Met Leu Val Glu Arg Ser
        115                 120                 125

Thr Asp Tyr Gly His Asn Trp Lys Val Phe Lys Tyr Phe Ala Lys Asp
130                 135                 140

Cys Ala Thr Ser Phe Pro Asn Ile Thr Ser Gly Gln Ala Gln Gly Val
145                 150                 155                 160

Gly Asp Ile Val Cys Asp Ser Lys Tyr Ser Asp Ile Glu Pro Ser Thr
                165                 170                 175

Gly Gly Glu Val Val Leu Lys Val Leu Asp Pro Ser Phe Glu Ile Glu
            180                 185                 190

Asn Pro Tyr Ser Pro Tyr Ile Gln Asp Leu Val Thr Leu Thr Asn Leu
        195                 200                 205

Arg Ile Asn Phe Thr Lys Leu His Thr Leu Gly Asp Ala Leu Leu Gly
210                 215                 220

Arg Arg Gln Asn Asp Ser Leu Asp Lys Tyr Tyr Tyr Ala Leu Tyr Glu
225                 230                 235                 240

Met Ile Val Arg Gly Ser Cys Phe Cys Asn Gly His Ala Ser Glu Cys
                245                 250                 255

Arg Pro Met Gln Lys Met Arg Gly Asp Val Phe Ser Pro Pro Gly Met
            260                 265                 270

Val His Gly Gln Cys Val Cys Gln His Asn Thr Asp Gly Pro Asn Cys
        275                 280                 285

Glu Arg Cys Lys Asp Phe Phe Gln Asp Ala Pro Trp
    290                 295                 300

<210> SEQ ID NO 16
<211> LENGTH: 301
<212> TYPE: PRT
<213> ORGANISM: Artificial Sequence
<220> FEATURE:
<223> OTHER INFORMATION: Subfragment 2

<400> SEQUENCE: 16

Met Pro Asn Cys Glu Arg Cys Lys Asp Phe Phe Gln Asp Ala Pro Trp
1               5                   10                  15

Arg Pro Ala Ala Asp Leu Gln Asp Asn Ala Cys Arg Ser Cys Ser Cys
            20                  25                  30

Asn Ser His Ser Ser Arg Cys His Phe Asp Met Thr Thr Tyr Leu Ala
        35                  40                  45

Ser Gly Gly Leu Ser Gly Gly Val Cys Glu Asp Cys Gln His Asn Thr
    50                  55                  60

Glu Gly Gln His Cys Asp Arg Cys Arg Pro Leu Phe Tyr Arg Asp Pro
65                  70                  75                  80

Leu Lys Thr Ile Ser Asp Pro Tyr Ala Cys Ile Pro Cys Glu Cys Asp
                85                  90                  95

Pro Asp Gly Thr Ile Ser Gly Gly Ile Cys Val Ser His Ser Asp Pro
```

```
            100                 105                 110
Ala Leu Gly Ser Val Ala Gly Gln Cys Leu Cys Lys Glu Asn Val Glu
            115                 120                 125

Gly Ala Lys Cys Asp Gln Cys Lys Pro Asn His Tyr Gly Leu Ser Ala
        130                 135                 140

Thr Asp Pro Leu Gly Cys Gln Pro Cys Asp Cys Asn Pro Leu Gly Ser
145                 150                 155                 160

Leu Pro Phe Leu Thr Cys Asp Val Asp Thr Gly Gln Cys Leu Cys Leu
                    165                 170                 175

Ser Tyr Val Thr Gly Ala His Cys Glu Glu Cys Thr Val Gly Tyr Trp
            180                 185                 190

Gly Leu Gly Asn His Leu His Gly Cys Ser Pro Cys Asp Cys Asp Ile
        195                 200                 205

Gly Gly Ala Tyr Ser Asn Val Cys Ser Pro Lys Asn Gly Gln Cys Glu
        210                 215                 220

Cys Arg Pro His Val Thr Gly Arg Ser Cys Ser Glu Pro Ala Pro Gly
225                 230                 235                 240

Tyr Phe Phe Ala Pro Leu Asn Phe Tyr Leu Tyr Glu Ala Glu Glu Ala
                    245                 250                 255

Thr Thr Leu Gln Gly Leu Ala Pro Leu Gly Ser Glu Thr Phe Gly Gln
            260                 265                 270

Ser Pro Ala Val His Val Leu Gly Glu Pro Val Pro Gly Asn Pro
        275                 280                 285

Val Thr Trp Thr Gly Pro Gly Phe Ala Arg Val Leu Trp
290                 295                 300

<210> SEQ ID NO 17
<211> LENGTH: 318
<212> TYPE: PRT
<213> ORGANISM: Artificial Sequence
<220> FEATURE:
<223> OTHER INFORMATION: Subfragment 3

<400> SEQUENCE: 17

Met Gly Asn Pro Val Thr Trp Thr Gly Pro Gly Phe Ala Arg Val Leu
1               5                   10                  15

Pro Gly Ala Gly Leu Arg Phe Ala Val Asn Asn Ile Pro Phe Pro Val
            20                  25                  30

Asp Phe Thr Ile Ala Ile His Tyr Glu Thr Gln Ser Ala Ala Asp Trp
        35                  40                  45

Thr Val Gln Ile Val Val Asn Pro Pro Gly Gly Ser Glu His Cys Ile
    50                  55                  60

Pro Lys Thr Leu Gln Ser Lys Pro Gln Ser Phe Ala Leu Pro Ala Ala
65                  70                  75                  80

Thr Arg Ile Met Leu Leu Pro Thr Pro Ile Cys Leu Glu Pro Asp Val
                    85                  90                  95

Gln Tyr Ser Ile Asp Val Tyr Phe Ser Gln Pro Leu Gln Gly Glu Ser
            100                 105                 110

His Ala His Ser His Val Leu Val Asp Ser Leu Gly Leu Ile Pro Gln
            115                 120                 125

Ile Asn Ser Leu Glu Asn Phe Cys Ser Lys Gln Asp Leu Asp Glu Tyr
        130                 135                 140

Gln Leu His Asn Cys Val Glu Ile Ala Ser Ala Met Gly Pro Gln Val
145                 150                 155                 160

Leu Pro Gly Ala Cys Glu Arg Leu Ile Ile Ser Met Ser Ala Lys Leu
```

```
                 165                 170                 175
His Asp Gly Ala Val Ala Cys Lys Cys His Pro Gln Gly Ser Val Gly
            180                 185                 190

Ser Ser Cys Ser Arg Leu Gly Gly Gln Cys Gln Cys Lys Pro Leu Val
            195                 200                 205

Val Gly Arg Cys Cys Asp Arg Cys Ser Thr Gly Ser Tyr Asp Leu Gly
            210                 215                 220

His His Gly Cys His Pro Cys His Cys His Pro Gln Gly Ser Lys Asp
225                 230                 235                 240

Thr Val Cys Asp Gln Val Thr Gly Gln Cys Pro Cys His Gly Glu Val
            245                 250                 255

Ser Gly Arg Arg Cys Asp Arg Cys Leu Ala Gly Tyr Phe Gly Phe Pro
            260                 265                 270

Ser Cys His Pro Cys Pro Cys Asn Arg Phe Ala Glu Leu Cys Asp Pro
            275                 280                 285

Glu Thr Gly Ser Cys Phe Asn Cys Gly Phe Thr Thr Gly Arg Asn
            290                 295                 300

Cys Glu Arg Cys Ile Asp Gly Tyr Tyr Gly Asn Trp Gly Trp
305                 310                 315

<210> SEQ ID NO 18
<211> LENGTH: 286
<212> TYPE: PRT
<213> ORGANISM: Artificial Sequence
<220> FEATURE:
<223> OTHER INFORMATION: Subfragment 4

<400> SEQUENCE: 18

Met Thr Gly Arg Asn Cys Glu Arg Cys Ile Asp Gly Tyr Tyr Gly Asn
1               5                   10                  15

Pro Ser Ser Gly Gln Pro Cys Arg Pro Cys Leu Cys Pro Asp Asp Pro
            20                  25                  30

Ser Ser Asn Gln Tyr Phe Ala His Ser Cys Tyr Gln Asn Leu Trp Ser
            35                  40                  45

Ser Asp Val Ile Cys Asn Cys Leu Gln Gly Tyr Thr Gly Thr Gln Cys
        50                  55                  60

Gly Glu Cys Ser Thr Gly Phe Tyr Gly Asn Pro Arg Ile Ser Gly Ala
65              70                  75                  80

Pro Cys Gln Pro Cys Ala Cys Asn Asn Asn Ile Asp Val Thr Asp Pro
            85                  90                  95

Glu Ser Cys Ser Arg Val Thr Gly Glu Cys Leu Arg Cys Leu His Asn
            100                 105                 110

Thr Gln Gly Ala Asn Cys Gln Leu Cys Lys Pro Gly His Tyr Gly Ser
            115                 120                 125

Ala Leu Asn Gln Thr Cys Arg Arg Cys Ser Cys His Ala Ser Gly Val
        130                 135                 140

Ser Pro Met Glu Cys Pro Pro Gly Gly Gly Ala Cys Leu Cys Asp Pro
145                 150                 155                 160

Val Thr Gly Ala Cys Pro Cys Leu Pro Asn Val Thr Gly Leu Ala Cys
            165                 170                 175

Asp Arg Cys Ala Asp Gly Tyr Trp Asn Leu Val Pro Gly Arg Gly Cys
            180                 185                 190

Gln Ser Cys Asp Cys Asp Pro Arg Thr Ser Gln Ser Ser His Cys Asp
            195                 200                 205

Gln Leu Thr Gly Gln Cys Pro Cys Lys Leu Gly Tyr Gly Gly Lys Arg
```

```
               210                 215                 220
Cys Ser Glu Cys Gln Glu Asn Tyr Tyr Gly Asp Pro Pro Gly Arg Cys
225                 230                 235                 240

Ile Pro Cys Asp Cys Asn Arg Ala Gly Thr Gln Lys Pro Ile Cys Asp
                245                 250                 255

Pro Asp Thr Gly Met Cys Arg Cys Arg Glu Gly Val Ser Gly Gln Arg
                260                 265                 270

Cys Asp Arg Cys Ala Arg Gly His Ser Gln Glu Trp Gly Trp
275                 280                 285

<210> SEQ ID NO 19
<211> LENGTH: 320
<212> TYPE: PRT
<213> ORGANISM: Artificial Sequence
<220> FEATURE:
<223> OTHER INFORMATION: Subfragment 5

<400> SEQUENCE: 19

Met Ser Gly Gln Arg Cys Asp Arg Cys Ala Arg Gly His Ser Gln Glu
1               5                   10                  15

Phe Pro Thr Cys Leu Gln Cys His Leu Cys Phe Asp Gln Trp Asp His
                20                  25                  30

Thr Ile Ser Ser Leu Ser Lys Ala Val Gln Gly Leu Met Arg Leu Ala
                35                  40                  45

Ala Asn Met Glu Asp Lys Arg Glu Thr Leu Pro Val Cys Glu Ala Asp
                50                  55                  60

Phe Lys Asp Leu Arg Gly Asn Val Ser Glu Ile Glu Arg Ile Leu Lys
65                  70                  75                  80

His Pro Val Phe Pro Ser Gly Lys Phe Leu Lys Val Lys Asp Tyr His
                85                  90                  95

Asp Ser Val Arg Arg Gln Ile Met Gln Leu Asn Glu Gln Leu Lys Ala
                100                 105                 110

Val Tyr Glu Phe Gln Asp Leu Lys Asp Thr Ile Glu Arg Ala Lys Asn
                115                 120                 125

Glu Ala Asp Leu Leu Leu Glu Asp Leu Gln Glu Glu Ile Asp Leu Gln
130                 135                 140

Ser Ser Val Leu Asn Ala Ser Ile Ala Asp Ser Ser Glu Asn Ile Lys
145                 150                 155                 160

Lys Tyr Tyr His Ile Ser Ser Ser Ala Glu Lys Lys Ile Asn Glu Thr
                165                 170                 175

Ser Ser Thr Ile Asn Thr Ser Ala Asn Thr Arg Asn Asp Leu Leu Thr
                180                 185                 190

Ile Leu Asp Thr Leu Thr Ser Lys Gly Asn Leu Ser Leu Glu Arg Leu
                195                 200                 205

Lys Gln Ile Lys Ile Pro Asp Ile Gln Ile Leu Asn Glu Lys Val Cys
210                 215                 220

Gly Asp Pro Gly Asn Val Pro Cys Val Pro Leu Pro Cys Gly Gly Ala
225                 230                 235                 240

Leu Cys Thr Gly Arg Lys Gly His Arg Lys Cys Arg Gly Pro Gly Cys
                245                 250                 255

His Gly Ser Leu Thr Leu Ser Thr Asn Ala Leu Gln Lys Ala Gln Glu
                260                 265                 270

Ala Lys Ser Ile Ile Arg Asn Leu Asp Lys Gln Val Arg Gly Leu Lys
                275                 280                 285

Asn Gln Ile Glu Ser Ile Ser Glu Gln Ala Glu Val Ser Lys Asn Asn
```

```
                290                 295                 300
Ala Leu Gln Leu Arg Glu Lys Leu Gly Asn Ile Trp Gly Trp Gly Trp
305                 310                 315                 320

<210> SEQ ID NO 20
<211> LENGTH: 317
<212> TYPE: PRT
<213> ORGANISM: Artificial Sequence
<220> FEATURE:
<223> OTHER INFORMATION: Subfragment 6

<400> SEQUENCE: 20

Met Ser Lys Asn Asn Ala Leu Gln Leu Arg Glu Lys Leu Gly Asn Ile
1               5                   10                  15

Arg Asn Gln Ser Asp Ser Glu Glu Asn Ile Asn Leu Phe Ile Lys
                20                  25                  30

Lys Val Lys Asn Phe Leu Leu Glu Glu Asn Val Pro Pro Glu Asp Ile
            35                  40                  45

Glu Lys Val Ala Asn Gly Val Leu Asp Ile His Leu Pro Ile Pro Ser
    50                  55                  60

Gln Asn Leu Thr Asp Glu Leu Val Lys Ile Gln Lys His Met Gln Leu
65                  70                  75                  80

Cys Glu Asp Tyr Arg Thr Asp Glu Asn Arg Leu Asn Glu Glu Ala Asp
                85                  90                  95

Gly Ala Gln Lys Leu Leu Val Lys Ala Lys Ala Glu Lys Ala Ala
            100                 105                 110

Asn Ile Leu Leu Asn Leu Asp Lys Thr Leu Asn Gln Leu Gln Gln Ala
    115                 120                 125

Gln Ile Thr Gln Gly Arg Ala Asn Ser Thr Ile Thr Gln Leu Thr Ala
130                 135                 140

Asn Ile Thr Lys Ile Lys Lys Asn Val Leu Gln Ala Glu Asn Gln Thr
145                 150                 155                 160

Arg Glu Met Lys Ser Glu Leu Glu Leu Ala Lys Gln Arg Ser Gly Leu
                165                 170                 175

Glu Asp Gly Leu Ser Leu Leu Gln Thr Lys Leu Gln Arg His Gln Asp
            180                 185                 190

His Ala Val Asn Ala Lys Val Gln Ala Glu Ser Ala Gln His Gln Ala
    195                 200                 205

Gly Ser Leu Glu Lys Glu Phe Val Glu Leu Lys Lys Gln Tyr Ala Ile
210                 215                 220

Leu Gln Arg Lys Thr Ser Thr Thr Gly Leu Thr Lys Glu Thr Leu Gly
225                 230                 235                 240

Lys Val Lys Gln Leu Lys Asp Ala Ala Glu Lys Leu Ala Gly Asp Thr
                245                 250                 255

Glu Ala Lys Ile Arg Arg Ile Thr Asp Leu Glu Arg Lys Ile Gln Asp
            260                 265                 270

Leu Asn Leu Ser Arg Gln Ala Lys Ala Asp Gln Leu Arg Ile Leu Glu
    275                 280                 285

Asp Gln Val Val Ala Ile Lys Asn Glu Ile Val Glu Gln Glu Lys Lys
290                 295                 300

Tyr Ala Arg Cys Tyr Ser Trp Gly Trp Gly Trp Gly Trp
305                 310                 315

<210> SEQ ID NO 21
<211> LENGTH: 308
<212> TYPE: PRT
```

<213> ORGANISM: Artificial Sequence
<220> FEATURE:
<223> OTHER INFORMATION: Subfragment 1, with four tryptophans and
      C-terminal His-tag (AMB4-TF1-4W-His)

<400> SEQUENCE: 21

```
Met Gln Asp Asp Cys Asn Arg Gly Ala Cys His Pro Thr Thr Gly Asp
1               5                   10                  15

Leu Leu Val Gly Arg Asn Thr Gln Leu Met Ala Ser Ser Thr Cys Gly
            20                  25                  30

Leu Ser Arg Ala Gln Lys Tyr Cys Ile Leu Ser Tyr Leu Glu Gly Glu
        35                  40                  45

Gln Lys Cys Phe Ile Cys Asp Ser Arg Phe Pro Tyr Asp Pro Tyr Asp
    50                  55                  60

Gln Pro Asn Ser His Thr Ile Glu Asn Val Ile Val Ser Phe Glu Pro
65                  70                  75                  80

Asp Arg Glu Lys Lys Trp Trp Gln Ser Glu Asn Gly Leu Asp His Val
                85                  90                  95

Ser Ile Arg Leu Asp Leu Glu Ala Leu Phe Arg Phe Ser His Leu Ile
            100                 105                 110

Leu Thr Phe Lys Thr Phe Arg Pro Ala Ala Met Leu Val Glu Arg Ser
        115                 120                 125

Thr Asp Tyr Gly His Asn Trp Lys Val Phe Lys Tyr Phe Ala Lys Asp
130                 135                 140

Cys Ala Thr Ser Phe Pro Asn Ile Thr Ser Gly Gln Ala Gln Gly Val
145                 150                 155                 160

Gly Asp Ile Val Cys Asp Ser Lys Tyr Ser Asp Ile Glu Pro Ser Thr
                165                 170                 175

Gly Gly Glu Val Val Leu Lys Val Leu Asp Pro Ser Phe Glu Ile Glu
            180                 185                 190

Asn Pro Tyr Ser Pro Tyr Ile Gln Asp Leu Val Thr Leu Thr Asn Leu
        195                 200                 205

Arg Ile Asn Phe Thr Lys Leu His Thr Leu Gly Asp Ala Leu Leu Gly
    210                 215                 220

Arg Arg Gln Asn Asp Ser Leu Asp Lys Tyr Tyr Tyr Ala Leu Tyr Glu
225                 230                 235                 240

Met Ile Val Arg Gly Ser Cys Phe Cys Asn Gly His Ala Ser Glu Cys
                245                 250                 255

Arg Pro Met Gln Lys Met Arg Gly Asp Val Phe Ser Pro Pro Gly Met
            260                 265                 270

Val His Gly Gln Cys Val Cys Gln His Asn Thr Asp Gly Pro Asn Cys
        275                 280                 285

Glu Arg Cys Lys Asp Phe Phe Gln Asp Ala Pro Trp Leu Glu His His
    290                 295                 300

His His His His
305
```

<210> SEQ ID NO 22
<211> LENGTH: 309
<212> TYPE: PRT
<213> ORGANISM: Artificial Sequence
<220> FEATURE:
<223> OTHER INFORMATION: Subfragment 2, with four tryptophans and
      C-terminal His-tag (LAMB4-TF2-4W-His)

<400> SEQUENCE: 22

Met Pro Asn Cys Glu Arg Cys Lys Asp Phe Phe Gln Asp Ala Pro Trp

```
            1               5                  10                 15
          Arg Pro Ala Ala Asp Leu Gln Asp Asn Ala Cys Arg Ser Cys Ser Cys
                          20                 25                 30

Asn Ser His Ser Ser Arg Cys His Phe Asp Met Thr Thr Tyr Leu Ala
                          35                 40                 45

Ser Gly Gly Leu Ser Gly Val Cys Glu Asp Cys Gln His Asn Thr
                          50                 55                 60

Glu Gly Gln His Cys Asp Arg Cys Arg Pro Leu Phe Tyr Arg Asp Pro
           65                 70                 75                 80

Leu Lys Thr Ile Ser Asp Pro Tyr Ala Cys Ile Pro Cys Glu Cys Asp
                          85                 90                 95

Pro Asp Gly Thr Ile Ser Gly Ile Cys Val Ser His Ser Asp Pro
                          100                105                110

Ala Leu Gly Ser Val Ala Gly Gln Cys Leu Cys Lys Glu Asn Val Glu
                          115                120                125

Gly Ala Lys Cys Asp Gln Cys Lys Pro Asn His Tyr Gly Leu Ser Ala
                          130                135                140

Thr Asp Pro Leu Gly Cys Gln Pro Cys Asp Cys Asn Pro Leu Gly Ser
          145                150                155                160

Leu Pro Phe Leu Thr Cys Asp Val Asp Thr Gly Gln Cys Leu Cys Leu
                          165                170                175

Ser Tyr Val Thr Gly Ala His Cys Glu Glu Cys Thr Val Gly Tyr Trp
                          180                185                190

Gly Leu Gly Asn His Leu His Gly Cys Ser Pro Cys Asp Cys Asp Ile
                          195                200                205

Gly Gly Ala Tyr Ser Asn Val Cys Ser Pro Lys Asn Gly Gln Cys Glu
                          210                215                220

Cys Arg Pro His Val Thr Gly Arg Ser Cys Ser Glu Pro Ala Pro Gly
          225                230                235                240

Tyr Phe Phe Ala Pro Leu Asn Phe Tyr Leu Tyr Glu Ala Glu Ala
                          245                250                255

Thr Thr Leu Gln Gly Leu Ala Pro Leu Gly Ser Glu Thr Phe Gly Gln
                          260                265                270

Ser Pro Ala Val His Val Val Leu Gly Glu Pro Val Pro Gly Asn Pro
                          275                280                285

Val Thr Trp Thr Gly Pro Gly Phe Ala Arg Val Leu Trp Leu Glu His
                          290                295                300

His His His His His
          305

<210> SEQ ID NO 23
<211> LENGTH: 326
<212> TYPE: PRT
<213> ORGANISM: Artificial Sequence
<220> FEATURE:
<223> OTHER INFORMATION: Subfragment 3, with four tryptophans and
      C-terminal His-tag (LAMB4-TF3-4W-His)

<400> SEQUENCE: 23

Met Gly Asn Pro Val Thr Trp Thr Gly Pro Gly Phe Ala Arg Val Leu
 1               5                  10                  15

Pro Gly Ala Gly Leu Arg Phe Ala Val Asn Asn Ile Pro Phe Pro Val
                20                  25                  30

Asp Phe Thr Ile Ala Ile His Tyr Glu Thr Gln Ser Ala Ala Asp Trp
                35                  40                  45
```

```
Thr Val Gln Ile Val Asn Pro Gly Gly Ser Glu His Cys Ile
 50                  55                  60

Pro Lys Thr Leu Gln Ser Lys Pro Gln Ser Phe Ala Leu Pro Ala Ala
 65                  70                  75                  80

Thr Arg Ile Met Leu Leu Pro Thr Pro Ile Cys Leu Glu Pro Asp Val
                 85                  90                  95

Gln Tyr Ser Ile Asp Val Tyr Phe Ser Gln Pro Leu Gln Gly Glu Ser
                100                 105                 110

His Ala His Ser His Val Leu Val Asp Ser Leu Gly Leu Ile Pro Gln
                115                 120                 125

Ile Asn Ser Leu Glu Asn Phe Cys Ser Lys Gln Asp Leu Asp Glu Tyr
130                 135                 140

Gln Leu His Asn Cys Val Glu Ile Ala Ser Ala Met Gly Pro Gln Val
145                 150                 155                 160

Leu Pro Gly Ala Cys Glu Arg Leu Ile Ile Ser Met Ser Ala Lys Leu
                165                 170                 175

His Asp Gly Ala Val Ala Cys Lys Cys His Pro Gln Gly Ser Val Gly
                180                 185                 190

Ser Ser Cys Ser Arg Leu Gly Gly Gln Cys Gln Cys Lys Pro Leu Val
                195                 200                 205

Val Gly Arg Cys Cys Asp Arg Cys Ser Thr Gly Ser Tyr Asp Leu Gly
210                 215                 220

His His Gly Cys His Pro Cys His Pro Gln Gly Ser Lys Asp
225                 230                 235                 240

Thr Val Cys Asp Gln Val Thr Gly Gln Cys Pro Cys His Gly Glu Val
                245                 250                 255

Ser Gly Arg Arg Cys Asp Arg Cys Leu Ala Gly Tyr Phe Gly Phe Pro
                260                 265                 270

Ser Cys His Pro Cys Pro Cys Asn Arg Phe Ala Glu Leu Cys Asp Pro
                275                 280                 285

Glu Thr Gly Ser Cys Phe Asn Cys Gly Gly Phe Thr Thr Gly Arg Asn
                290                 295                 300

Cys Glu Arg Cys Ile Asp Gly Tyr Tyr Gly Asn Trp Gly Trp Leu Glu
305                 310                 315                 320

His His His His His His
                325

<210> SEQ ID NO 24
<211> LENGTH: 294
<212> TYPE: PRT
<213> ORGANISM: Artificial Sequence
<220> FEATURE:
<223> OTHER INFORMATION: Subfragment 4, with four tryptophans and
      C-terminal His-tag (LAMB4-TF4-4W-His)

<400> SEQUENCE: 24

Met Thr Gly Arg Asn Cys Glu Arg Cys Ile Asp Gly Tyr Tyr Gly Asn
 1               5                  10                  15

Pro Ser Ser Gly Gln Pro Cys Arg Pro Cys Leu Cys Pro Asp Asp Pro
                20                  25                  30

Ser Ser Asn Gln Tyr Phe Ala His Ser Cys Tyr Gln Asn Leu Trp Ser
                35                  40                  45

Ser Asp Val Ile Cys Asn Cys Leu Gln Gly Tyr Thr Gly Thr Gln Cys
 50                  55                  60

Gly Glu Cys Ser Thr Gly Phe Tyr Gly Asn Pro Arg Ile Ser Gly Ala
 65                  70                  75                  80
```

Pro Cys Gln Pro Cys Ala Cys Asn Asn Asn Ile Asp Val Thr Asp Pro
            85                  90                  95

Glu Ser Cys Ser Arg Val Thr Gly Glu Cys Leu Arg Cys Leu His Asn
            100                 105                 110

Thr Gln Gly Ala Asn Cys Gln Leu Cys Lys Pro Gly His Tyr Gly Ser
            115                 120                 125

Ala Leu Asn Gln Thr Cys Arg Arg Cys Ser Cys His Ala Ser Gly Val
        130                 135                 140

Ser Pro Met Glu Cys Pro Gly Gly Ala Cys Leu Cys Asp Pro
145                 150                 155                 160

Val Thr Gly Ala Cys Pro Cys Leu Pro Asn Val Thr Gly Leu Ala Cys
                165                 170                 175

Asp Arg Cys Ala Asp Gly Tyr Trp Asn Leu Val Pro Gly Arg Gly Cys
            180                 185                 190

Gln Ser Cys Asp Cys Asp Pro Arg Thr Ser Gln Ser Ser His Cys Asp
        195                 200                 205

Gln Leu Thr Gly Gln Cys Pro Cys Lys Leu Gly Tyr Gly Gly Lys Arg
    210                 215                 220

Cys Ser Glu Cys Gln Glu Asn Tyr Tyr Gly Asp Pro Pro Gly Arg Cys
225                 230                 235                 240

Ile Pro Cys Asp Cys Asn Arg Ala Gly Thr Gln Lys Pro Ile Cys Asp
                245                 250                 255

Pro Asp Thr Gly Met Cys Arg Cys Arg Glu Gly Val Ser Gly Gln Arg
            260                 265                 270

Cys Asp Arg Cys Ala Arg Gly His Ser Gln Glu Trp Gly Trp Leu Glu
        275                 280                 285

His His His His His His
    290

<210> SEQ ID NO 25
<211> LENGTH: 328
<212> TYPE: PRT
<213> ORGANISM: Artificial Sequence
<220> FEATURE:
<223> OTHER INFORMATION: Subfragment 5, with four tryptophans and
      C-terminal His-tag (LAMB4-TF5-4W-His)

<400> SEQUENCE: 25

Met Ser Gly Gln Arg Cys Asp Arg Cys Ala Arg Gly His Ser Gln Glu
1               5                   10                  15

Phe Pro Thr Cys Leu Gln Cys His Leu Cys Phe Asp Gln Trp Asp His
            20                  25                  30

Thr Ile Ser Ser Leu Ser Lys Ala Val Gln Gly Leu Met Arg Leu Ala
            35                  40                  45

Ala Asn Met Glu Asp Lys Arg Glu Thr Leu Pro Val Cys Glu Ala Asp
        50                  55                  60

Phe Lys Asp Leu Arg Gly Asn Val Ser Glu Ile Glu Arg Ile Leu Lys
65                  70                  75                  80

His Pro Val Phe Pro Ser Gly Lys Phe Leu Lys Val Lys Asp Tyr His
                85                  90                  95

Asp Ser Val Arg Arg Gln Ile Met Gln Leu Asn Glu Gly Leu Lys Ala
            100                 105                 110

Val Tyr Glu Phe Gln Asp Leu Lys Asp Thr Ile Glu Arg Ala Lys Asn
        115                 120                 125

Glu Ala Asp Leu Leu Leu Glu Asp Leu Gln Glu Glu Ile Asp Leu Gln

```
            130                 135                 140
Ser Ser Val Leu Asn Ala Ser Ile Ala Asp Ser Ser Glu Asn Ile Lys
145                 150                 155                 160

Lys Tyr Tyr His Ile Ser Ser Ala Glu Lys Lys Ile Asn Glu Thr
                165                 170                 175

Ser Ser Thr Ile Asn Thr Ser Ala Asn Thr Arg Asn Asp Leu Leu Thr
                180                 185                 190

Ile Leu Asp Thr Leu Thr Ser Lys Gly Asn Leu Ser Leu Glu Arg Leu
                195                 200                 205

Lys Gln Ile Lys Ile Pro Asp Ile Gln Ile Leu Asn Glu Lys Val Cys
                210                 215                 220

Gly Asp Pro Gly Asn Val Pro Cys Val Pro Leu Pro Cys Gly Gly Ala
225                 230                 235                 240

Leu Cys Thr Gly Arg Lys Gly His Arg Lys Cys Arg Gly Pro Gly Cys
                245                 250                 255

His Gly Ser Leu Thr Leu Ser Thr Asn Ala Leu Gln Lys Ala Gln Glu
                260                 265                 270

Ala Lys Ser Ile Ile Arg Asn Leu Asp Lys Gln Val Arg Gly Leu Lys
                275                 280                 285

Asn Gln Ile Glu Ser Ile Ser Glu Gln Ala Glu Val Ser Lys Asn Asn
                290                 295                 300

Ala Leu Gln Leu Arg Glu Lys Leu Gly Asn Ile Trp Gly Trp Gly Trp
305                 310                 315                 320

Leu Glu His His His His His His
                325

<210> SEQ ID NO 26
<211> LENGTH: 325
<212> TYPE: PRT
<213> ORGANISM: Artificial Sequence
<220> FEATURE:
<223> OTHER INFORMATION: Subfragment 6, with four tryptophans and
      C-terminal His-tag (LAMB4-TF6-4W-His)

<400> SEQUENCE: 26

Met Ser Lys Asn Asn Ala Leu Gln Leu Arg Glu Lys Leu Gly Asn Ile
1               5                   10                  15

Arg Asn Gln Ser Asp Ser Glu Glu Asn Ile Asn Leu Phe Ile Lys
                20                  25                  30

Lys Val Lys Asn Phe Leu Leu Glu Glu Asn Val Pro Pro Glu Asp Ile
                35                  40                  45

Glu Lys Val Ala Asn Gly Val Leu Asp Ile His Leu Pro Ile Pro Ser
            50                  55                  60

Gln Asn Leu Thr Asp Glu Leu Val Lys Ile Gln Lys His Met Gln Leu
65                  70                  75                  80

Cys Glu Asp Tyr Arg Thr Asp Glu Asn Arg Leu Asn Glu Glu Ala Asp
                85                  90                  95

Gly Ala Gln Lys Leu Leu Val Lys Ala Lys Ala Glu Lys Ala Ala
                100                 105                 110

Asn Ile Leu Leu Asn Leu Asp Lys Thr Leu Asn Gln Leu Gln Ala
                115                 120                 125

Gln Ile Thr Gln Gly Arg Ala Asn Ser Thr Ile Thr Gln Leu Thr Ala
                130                 135                 140

Asn Ile Thr Lys Ile Lys Lys Asn Val Leu Gln Ala Glu Asn Gln Thr
145                 150                 155                 160
```

```
Arg Glu Met Lys Ser Glu Leu Glu Leu Ala Lys Gln Arg Ser Gly Leu
                165                 170                 175

Glu Asp Gly Leu Ser Leu Leu Gln Thr Lys Leu Gln Arg His Gln Asp
            180                 185                 190

His Ala Val Asn Ala Lys Val Gln Ala Glu Ser Ala Gln His Gln Ala
        195                 200                 205

Gly Ser Leu Glu Lys Glu Phe Val Glu Leu Lys Lys Gln Tyr Ala Ile
    210                 215                 220

Leu Gln Arg Lys Thr Ser Thr Thr Gly Leu Thr Lys Glu Thr Leu Gly
225                 230                 235                 240

Lys Val Lys Gln Leu Lys Asp Ala Ala Glu Lys Leu Ala Gly Asp Thr
                245                 250                 255

Glu Ala Lys Ile Arg Arg Ile Thr Asp Leu Glu Arg Lys Ile Gln Asp
            260                 265                 270

Leu Asn Leu Ser Arg Gln Ala Lys Ala Asp Gln Leu Arg Ile Leu Glu
        275                 280                 285

Asp Gln Val Val Ala Ile Lys Asn Glu Ile Val Glu Gln Glu Lys Lys
    290                 295                 300

Tyr Ala Arg Cys Tyr Ser Trp Gly Trp Gly Trp Gly Trp Leu Glu His
305                 310                 315                 320

His His His His His
                325

<210> SEQ ID NO 27
<211> LENGTH: 1761
<212> TYPE: PRT
<213> ORGANISM: Homo sapiens

<400> SEQUENCE: 27

Met Gln Phe Gln Leu Thr Leu Phe Leu His Leu Gly Trp Leu Ser Tyr
1               5                   10                  15

Ser Lys Ala Gln Asp Asp Cys Asn Arg Gly Ala Cys His Pro Thr Thr
                20                  25                  30

Gly Asp Leu Leu Val Gly Arg Asn Thr Gln Leu Met Ala Ser Ser Thr
            35                  40                  45

Cys Gly Leu Ser Arg Ala Gln Lys Tyr Cys Ile Leu Ser Tyr Leu Glu
        50                  55                  60

Gly Glu Gln Lys Cys Phe Ile Cys Asp Ser Arg Phe Pro Tyr Asp Pro
65                  70                  75                  80

Tyr Asp Gln Pro Asn Ser His Thr Ile Glu Asn Val Ile Val Ser Phe
                85                  90                  95

Glu Pro Asp Arg Glu Lys Lys Trp Trp Gln Ser Glu Asn Gly Leu Asp
            100                 105                 110

His Val Ser Ile Arg Leu Asp Leu Glu Ala Leu Phe Arg Phe Ser His
        115                 120                 125

Leu Ile Leu Thr Phe Lys Thr Phe Arg Pro Ala Ala Met Leu Val Glu
130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
        195                 200                 205
```

```
Ile Glu Asn Pro Tyr Ser Pro Tyr Ile Gln Asp Leu Val Thr Leu Thr
    210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Ala Leu
            245                 250                 255

Tyr Glu Met Ile Val Arg Gly Ser Cys Phe Cys Asn Gly His Ala Ser
            260                 265                 270

Glu Cys Arg Pro Met Gln Lys Met Arg Gly Asp Val Phe Ser Pro Pro
        275                 280                 285

Gly Met Val His Gly Gln Cys Val Cys Gln His Asn Thr Asp Gly Pro
    290                 295                 300

Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
                325                 330                 335

His Ser Ser Arg Cys His Phe Asp Met Thr Thr Tyr Leu Ala Ser Gly
            340                 345                 350

Gly Leu Ser Gly Gly Val Cys Glu Asp Cys Gln His Asn Thr Glu Gly
        355                 360                 365

Gln His Cys Asp Arg Cys Arg Pro Leu Phe Tyr Arg Asp Pro Leu Lys
    370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Pro Ala Leu
                405                 410                 415

Gly Ser Val Ala Gly Gln Cys Leu Cys Lys Glu Asn Val Glu Gly Ala
            420                 425                 430

Lys Cys Asp Gln Cys Lys Pro Asn His Tyr Gly Leu Ser Ala Thr Asp
        435                 440                 445

Pro Leu Gly Cys Gln Pro Cys Asp Cys Asn Pro Leu Gly Ser Leu Pro
    450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
                485                 490                 495

Gly Asn His Leu His Gly Cys Ser Pro Cys Asp Cys Asp Ile Gly Gly
            500                 505                 510

Ala Tyr Ser Asn Val Cys Ser Pro Lys Asn Gly Gln Cys Glu Cys Arg
        515                 520                 525

Pro His Val Thr Gly Arg Ser Cys Ser Glu Pro Ala Pro Gly Tyr Phe
    530                 535                 540

Phe Ala Pro Leu Asn Phe Tyr Leu Tyr Glu Ala Glu Ala Thr Thr
545                 550                 555                 560

Leu Gln Gly Leu Ala Pro Leu Gly Ser Glu Thr Phe Gly Gln Ser Pro
                565                 570                 575

Ala Val His Val Val Leu Gly Glu Pro Val Pro Gly Asn Pro Val Thr
            580                 585                 590

Trp Thr Gly Pro Gly Phe Ala Arg Val Leu Pro Gly Ala Gly Leu Arg
        595                 600                 605

Phe Ala Val Asn Asn Ile Pro Phe Pro Val Asp Phe Thr Ile Ala Ile
    610                 615                 620
```

-continued

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
            645                 650                 655

Lys Pro Gln Ser Phe Ala Leu Pro Ala Ala Thr Arg Ile Met Leu Leu
        660                 665                 670

Pro Thr Pro Ile Cys Leu Glu Pro Asp Val Gln Tyr Ser Ile Asp Val
    675                 680                 685

Tyr Phe Ser Gln Pro Leu Gln Gly Glu Ser His Ala His Ser His Val
690                 695                 700

Leu Val Asp Ser Leu Gly Leu Ile Pro Gln Ile Asn Ser Leu Glu Asn
705                 710                 715                 720

Phe Cys Ser Lys Gln Asp Leu Asp Glu Tyr Gln Leu His Asn Cys Val
            725                 730                 735

Glu Ile Ala Ser Ala Met Gly Pro Gln Val Leu Pro Gly Ala Cys Glu
            740                 745                 750

Arg Leu Ile Ile Ser Met Ser Ala Lys Leu His Asp Gly Ala Val Ala
            755                 760                 765

Cys Lys Cys His Pro Gln Gly Ser Val Gly Ser Ser Cys Ser Arg Leu
770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
            805                 810                 815

Cys His Cys His Pro Gln Gly Ser Lys Asp Thr Val Cys Asp Gln Val
            820                 825                 830

Thr Gly Gln Cys Pro Cys His Gly Glu Val Ser Gly Arg Arg Cys Asp
            835                 840                 845

Arg Cys Leu Ala Gly Tyr Phe Gly Phe Pro Ser Cys His Pro Cys Pro
            850                 855                 860

Cys Asn Arg Phe Ala Glu Leu Cys Asp Pro Thr Gly Ser Cys Phe
865                 870                 875                 880

Asn Cys Gly Gly Phe Thr Thr Gly Arg Asn Cys Glu Arg Cys Ile Asp
            885                 890                 895

Gly Tyr Tyr Gly Asn Pro Ser Ser Gly Gln Pro Cys Arg Pro Cys Leu
            900                 905                 910

Cys Pro Asp Asp Pro Ser Ser Asn Gln Tyr Phe Ala His Ser Cys Tyr
            915                 920                 925

Gln Asn Leu Trp Ser Ser Asp Val Ile Cys Asn Cys Leu Gln Gly Tyr
930                 935                 940

Thr Gly Thr Gln Cys Gly Glu Cys Ser Thr Gly Phe Tyr Gly Asn Pro
945                 950                 955                 960

Arg Ile Ser Gly Ala Pro Cys Gln Pro Cys Ala Cys Asn Asn Asn Ile
            965                 970                 975

Asp Val Thr Asp Pro Glu Ser Cys Ser Arg Val Thr Gly Glu Cys Leu
            980                 985                 990

Arg Cys Leu His Asn Thr Gln Gly Ala Asn Cys Gln Leu Cys Lys Pro
            995                 1000                1005

Gly His Tyr Gly Ser Ala Leu Asn Gln Thr Cys Arg Arg Cys Ser
    1010                1015                1020

Cys His Ala Ser Gly Val Ser Pro Met Glu Cys Pro Pro Gly Gly
    1025                1030                1035

Gly Ala Cys Leu Cys Asp Pro Val Thr Gly Ala Cys Pro Cys Leu

```
            1040                1045                1050

Pro Asn Val Thr Gly Leu Ala Cys Asp Arg Cys Ala Asp Gly Tyr
    1055                1060                1065

Trp Asn Leu Val Pro Gly Arg Gly Cys Gln Ser Cys Asp Cys Asp
    1070                1075                1080

Pro Arg Thr Ser Gln Ser Ser His Cys Asp Gln Leu Thr Gly Gln
    1085                1090                1095

Cys Pro Cys Lys Leu Gly Tyr Gly Gly Lys Arg Cys Ser Glu Cys
    1100                1105                1110

Gln Glu Asn Tyr Tyr Gly Asp Pro Pro Gly Arg Cys Ile Pro Cys
    1115                1120                1125

Asp Cys Asn Arg Ala Gly Thr Gln Lys Pro Ile Cys Asp Pro Asp
    1130                1135                1140

Thr Gly Met Cys Arg Cys Arg Glu Gly Val Ser Gly Gln Arg Cys
    1145                1150                1155

Asp Arg Cys Ala Arg Gly His Ser Gln Glu Phe Pro Thr Cys Leu
    1160                1165                1170

Gln Cys His Leu Cys Phe Asp Gln Trp Asp His Thr Ile Ser Ser
    1175                1180                1185

Leu Ser Lys Ala Val Gln Gly Leu Met Arg Leu Ala Ala Asn Met
    1190                1195                1200

Glu Asp Lys Arg Glu Thr Leu Pro Val Cys Glu Ala Asp Phe Lys
    1205                1210                1215

Asp Leu Arg Gly Asn Val Ser Glu Ile Glu Arg Ile Leu Lys His
    1220                1225                1230

Pro Val Phe Pro Ser Gly Lys Phe Leu Lys Val Lys Asp Tyr His
    1235                1240                1245

Asp Ser Val Arg Arg Gln Ile Met Gln Leu Asn Glu Gln Leu Lys
    1250                1255                1260

Ala Val Tyr Glu Phe Gln Asp Leu Lys Asp Thr Ile Glu Arg Ala
    1265                1270                1275

Lys Asn Glu Ala Asp Leu Leu Leu Glu Asp Leu Gln Glu Glu Ile
    1280                1285                1290

Asp Leu Gln Ser Ser Val Leu Asn Ala Ser Ile Ala Asp Ser Ser
    1295                1300                1305

Glu Asn Ile Lys Lys Tyr Tyr His Ile Ser Ser Ser Ala Glu Lys
    1310                1315                1320

Lys Ile Asn Glu Thr Ser Ser Thr Ile Asn Thr Ser Ala Asn Thr
    1325                1330                1335

Arg Asn Asp Leu Leu Thr Ile Leu Asp Thr Leu Thr Ser Lys Gly
    1340                1345                1350

Asn Leu Ser Leu Glu Arg Leu Lys Gln Ile Lys Ile Pro Asp Ile
    1355                1360                1365

Gln Ile Leu Asn Glu Lys Val Cys Gly Asp Pro Gly Asn Val Pro
    1370                1375                1380

Cys Val Pro Leu Pro Cys Gly Gly Ala Leu Cys Thr Gly Arg Lys
    1385                1390                1395

Gly His Arg Lys Cys Arg Gly Pro Gly Cys His Gly Ser Leu Thr
    1400                1405                1410

Leu Ser Thr Asn Ala Leu Gln Lys Ala Gln Glu Ala Lys Ser Ile
    1415                1420                1425

Ile Arg Asn Leu Asp Lys Gln Val Arg Gly Leu Lys Asn Gln Ile
    1430                1435                1440
```

Glu Ser Ile Ser Glu Gln Ala Glu Val Ser Lys Asn Asn Ala Leu
1445                1450                1455

Gln Leu Arg Glu Lys Leu Gly Asn Ile Arg Asn Gln Ser Asp Ser
    1460                1465                1470

Glu Glu Glu Asn Ile Asn Leu Phe Ile Lys Lys Val Lys Asn Phe
1475                1480                1485

Leu Leu Glu Glu Asn Val Pro Pro Glu Asp Ile Glu Lys Val Ala
    1490                1495                1500

Asn Gly Val Leu Asp Ile His Leu Pro Ile Pro Ser Gln Asn Leu
1505                1510                1515

Thr Asp Glu Leu Val Lys Ile Gln Lys His Met Gln Leu Cys Glu
    1520                1525                1530

Asp Tyr Arg Thr Asp Glu Asn Arg Leu Asn Glu Glu Ala Asp Gly
1535                1540                1545

Ala Gln Lys Leu Leu Val Lys Ala Lys Ala Ala Glu Lys Ala Ala
    1550                1555                1560

Asn Ile Leu Leu Asn Leu Asp Lys Thr Leu Asn Gln Leu Gln Gln
1565                1570                1575

Ala Gln Ile Thr Gln Gly Arg Ala Asn Ser Thr Ile Thr Gln Leu
    1580                1585                1590

Thr Ala Asn Ile Thr Lys Ile Lys Lys Asn Val Leu Gln Ala Glu
1595                1600                1605

Asn Gln Thr Arg Glu Met Lys Ser Glu Leu Glu Leu Ala Lys Gln
    1610                1615                1620

Arg Ser Gly Leu Glu Asp Gly Leu Ser Leu Leu Gln Thr Lys Leu
1625                1630                1635

Gln Arg His Gln Asp His Ala Val Asn Ala Lys Val Gln Ala Glu
    1640                1645                1650

Ser Ala Gln His Gln Ala Gly Ser Leu Glu Lys Glu Phe Val Glu
1655                1660                1665

Leu Lys Lys Gln Tyr Ala Ile Leu Gln Arg Lys Thr Ser Thr Thr
    1670                1675                1680

Gly Leu Thr Lys Glu Thr Leu Gly Lys Val Lys Gln Leu Lys Asp
1685                1690                1695

Ala Ala Glu Lys Leu Ala Gly Asp Thr Glu Ala Lys Ile Arg Arg
    1700                1705                1710

Ile Thr Asp Leu Glu Arg Lys Ile Gln Asp Leu Asn Leu Ser Arg
1715                1720                1725

Gln Ala Lys Ala Asp Gln Leu Arg Ile Leu Glu Asp Gln Val Val
    1730                1735                1740

Ala Ile Lys Asn Glu Ile Val Glu Gln Glu Lys Lys Tyr Ala Arg
1745                1750                1755

Cys Tyr Ser
1760

<210> SEQ ID NO 28
<211> LENGTH: 779
<212> TYPE: PRT
<213> ORGANISM: Artificial Sequence
<220> FEATURE:
<223> OTHER INFORMATION: SEQ ID NO 8 from EP3260864

<400> SEQUENCE: 28

Met Asp Cys Thr Phe Lys Pro Asp Phe Glu Met Thr Val Lys Glu Cys
1               5                   10                  15

```
Gln His Ser Gly Glu Leu Ser Ser Arg Asn Thr Gly His Leu His Pro
             20                  25                  30

Thr Pro Arg Ser Pro Leu Leu Arg Trp Thr Gln Glu Pro Gln Pro Leu
         35                  40                  45

Glu Glu Lys Trp Gln His Arg Val Val Glu Gln Ile Pro Lys Glu Val
 50                  55                  60

Gln Phe Gln Pro Pro Gly Ala Pro Leu Glu Lys Glu Lys Ser Gln Gln
 65                  70                  75                  80

Cys Tyr Ser Glu Tyr Phe Ser Gln Thr Ser Thr Glu Leu Gln Ile Thr
                 85                  90                  95

Phe Asp Glu Thr Asn Pro Ile Thr Arg Leu Ser Glu Ile Glu Lys Ile
             100                 105                 110

Arg Asp Gln Ala Leu Asn Asn Ser Arg Pro Pro Val Arg Tyr Gln Asp
         115                 120                 125

Asn Ala Cys Glu Met Glu Leu Val Lys Val Leu Thr Pro Leu Glu Ile
130                 135                 140

Ala Lys Asn Lys Gln Tyr Asp Met His Thr Glu Val Thr Thr Leu Lys
145                 150                 155                 160

Gln Glu Lys Asn Pro Val Pro Ser Ala Glu Glu Trp Met Leu Glu Gly
                 165                 170                 175

Cys Arg Ala Ser Gly Gly Leu Lys Lys Gly Asp Phe Leu Lys Lys Gly
             180                 185                 190

Leu Glu Pro Glu Thr Phe Gln Asn Phe Asp Gly Asp His Ala Cys Ser
         195                 200                 205

Val Arg Asp Asp Glu Phe Lys Phe Gln Gly Leu Arg His Thr Val Thr
210                 215                 220

Ala Arg Gln Leu Val Glu Ala Lys Leu Leu Asp Met Arg Thr Ile Glu
225                 230                 235                 240

Gln Leu Arg Leu Gly Leu Lys Thr Val Glu Glu Val Gln Lys Thr Leu
                 245                 250                 255

Asn Lys Phe Leu Thr Lys Ala Thr Ser Ile Ala Gly Leu Tyr Leu Glu
             260                 265                 270

Ser Thr Lys Glu Lys Ile Ser Phe Ala Ser Ala Ala Glu Arg Ile Ile
         275                 280                 285

Ile Asp Lys Met Val Ala Leu Ala Phe Leu Glu Ala Gln Ala Ala Thr
290                 295                 300

Gly Phe Ile Ile Asp Pro Ile Ser Gly Gln Thr Tyr Ser Val Glu Asp
305                 310                 315                 320

Ala Val Leu Lys Gly Val Val Asp Pro Glu Phe Arg Ile Arg Leu Leu
                 325                 330                 335

Glu Ala Glu Lys Ala Val Gly Tyr Ser Tyr Ser Lys Thr Leu
             340                 345                 350

Ser Val Phe Gln Ala Met Glu Asn Arg Met Leu Asp Arg Gln Lys Gly
         355                 360                 365

Lys His Ile Leu Glu Ala Gln Ile Ala Ser Gly Gly Val Ile Asp Pro
370                 375                 380

Val Arg Gly Ile Arg Val Pro Pro Glu Ile Ala Leu Gln Gln Gly Leu
385                 390                 395                 400

Leu Asn Asn Ala Ile Leu Gln Phe Leu His Glu Pro Ser Ser Asn Thr
                 405                 410                 415

Arg Val Phe Pro Asn Pro Asn Asn Lys Gln Ala Leu Tyr Tyr Ser Glu
             420                 425                 430
```

```
Leu Leu Arg Met Cys Val Phe Asp Val Glu Ser Gln Cys Phe Leu Phe
            435                 440                 445

Pro Phe Gly Glu Arg Asn Ile Ser Asn Leu Asn Val Lys Lys Thr His
450                 455                 460

Arg Ile Ser Val Val Asp Thr Lys Thr Gly Ser Glu Leu Thr Val Tyr
465                 470                 475                 480

Glu Ala Phe Gln Arg Asn Leu Ile Glu Lys Ser Ile Tyr Leu Glu Leu
                485                 490                 495

Ser Gly Gln Gln Tyr Gln Trp Lys Glu Ala Met Phe Phe Glu Ser Tyr
                500                 505                 510

Gly His Ser Ser His Met Leu Thr Asp Thr Lys Thr Gly Leu His Phe
            515                 520                 525

Asn Ile Asn Glu Ala Ile Glu Gln Gly Thr Ile Asp Lys Ala Leu Val
            530                 535                 540

Lys Lys Tyr Gln Glu Gly Leu Ile Thr Leu Thr Glu Leu Ala Asp Ser
545                 550                 555                 560

Leu Leu Ser Arg Leu Val Pro Lys Lys Asp Leu His Ser Pro Val Ala
                565                 570                 575

Gly Tyr Trp Leu Thr Ala Ser Gly Glu Arg Ile Ser Val Leu Lys Ala
            580                 585                 590

Ser Arg Arg Asn Leu Val Asp Arg Ile Thr Ala Leu Arg Cys Leu Glu
            595                 600                 605

Ala Gln Val Ser Thr Gly Gly Ile Ile Asp Pro Leu Thr Gly Lys Lys
            610                 615                 620

Tyr Arg Val Ala Glu Ala Leu His Arg Gly Leu Val Asp Glu Gly Phe
625                 630                 635                 640

Ala Gln Gln Leu Arg Gln Cys Glu Leu Val Ile Thr Gly Ile Gly His
                645                 650                 655

Pro Ile Thr Asn Lys Met Met Ser Val Val Glu Ala Val Asn Ala Asn
            660                 665                 670

Ile Ile Asn Lys Glu Met Gly Ile Arg Cys Leu Glu Phe Gln Tyr Leu
            675                 680                 685

Thr Gly Gly Leu Ile Glu Pro Gln Val His Ser Arg Leu Ser Ile Glu
            690                 695                 700

Glu Ala Leu Gln Val Gly Ile Ile Asp Val Leu Ile Ala Thr Lys Leu
705                 710                 715                 720

Lys Asp Gln Lys Ser Tyr Val Arg Asn Ile Ile Cys Pro Gln Thr Lys
                725                 730                 735

Arg Lys Leu Thr Tyr Lys Glu Ala Leu Glu Lys Ala Asp Phe Asp Phe
            740                 745                 750

His Thr Gly Leu Lys Leu Leu Glu Val Ser Glu Pro Leu Met Thr Gly
            755                 760                 765

Ile Ser Ser Leu Tyr Tyr Ser Ser Leu Leu Glu
            770                 775

<210> SEQ ID NO 29
<211> LENGTH: 25
<212> TYPE: PRT
<213> ORGANISM: Artificial Sequence
<220> FEATURE:
<223> OTHER INFORMATION: Gliadin Peptide

<400> SEQUENCE: 29

Leu Gly Gln Gln Gln Pro Phe Pro Pro Gln Gln Pro Tyr Pro Gln Pro
1               5                   10                  15
```

```
Gln Pro Phe Pro Ser Gln Gln Pro Tyr
            20              25

<210> SEQ ID NO 30
<211> LENGTH: 17
<212> TYPE: PRT
<213> ORGANISM: Artificial Sequence
<220> FEATURE:
<223> OTHER INFORMATION: Gliadin Peptide

<400> SEQUENCE: 30

Gln Leu Gln Pro Phe Pro Gln Pro Glu Leu Pro Tyr Pro Gln Pro Gln
1               5                   10                  15

Ser

<210> SEQ ID NO 31
<211> LENGTH: 20
<212> TYPE: PRT
<213> ORGANISM: Artificial Sequence
<220> FEATURE:
<223> OTHER INFORMATION: Gliadin Peptide

<400> SEQUENCE: 31

Gln Gln Leu Pro Gln Pro Glu Gln Pro Gln Gln Ser Phe Pro Glu Gln
1               5                   10                  15

Glu Arg Pro Phe
            20
```

DIAGNOSIS OF BLISTERING AUTOIMMUNE DISEASE

CROSS-REFERENCE TO RELATED APPLICATIONS

The present application claims the benefit of the European Application EP18201752.5, filed on Oct. 22, 2018, which is incorporated by reference in its entirety.

REFERENCE TO A SEQUENCE LISTING

The present application is accompanied by an ASCII text file as a computer readable form containing the sequence listing, titled "2019-10-11-seq-list-as-filed", created on Oct. 11, 2019, with the file size of 110,547 bytes, which is incorporated by reference in its entirety. Applicants hereby state that the information recorded in computer readable form is identical to the written (on paper or compact disc) sequence listing.

BACKGROUND OF THE INVENTION

Field of the Invention

The present invention relates to a polypeptide comprising laminin beta-4, to a carrier comprising the polypeptide, to an antibody, preferably autoantibody, against laminin beta-4, to use of the polypeptide, carrier or autoantibody for the diagnosis of a disease and to a method comprising the step of detecting an autoantibody against laminin beta-4 in a sample.

Discussion of the Background

Autoimmune diseases are understood to mean diseases in which the immune system is directed against intact structures endogenous to the body. In many autoimmune diseases, the body produces detectable autoantibodies which can bind against proteins endogenous to the body and thus cause disorders. In other cases, the presence of autoantibodies does not appear to be causally responsible for the outbreak of disease.

Blistering autoimmune diseases are distinguished by autoantibodies attacking target structures in the skin. Immune mechanisms bring about the detachment of the upper parts of the skin, and this leads to the formation of blisters.

On the basis of the target antigens and of the localization of split formation, a distinction is made between 4 main groups: pemphigus and pemphigoid diseases, epidermolysis bullosa acquisita (EBA) and dermatitis herpetiformis. Blistering is intraepithelial in the case of pemphigus diseases and subepithelial in the case of the other bullous autoimmune dermatoses.

Pemphigus vulgaris (PV) is the most common pemphigus disease, followed by pemphigus foliaceus, whereas other forms of pemphigus diseases such as paraneoplastic pemphigus occur very rarely. Pemphigus vulgaris (PV) is distinguished by blisters which burst relatively rapidly and which leave behind redness, erosions and crusts on the skin, due to dissolution of associated cells in the epidermis. Infections commonly occur at the affected sites. In many cases and at the start of the disease, the oral mucous membranes or the genital mucous membranes are affected by the blisters with severe soreness. If the disease is not identified and therapied in time, severe and, in some cases, fatal courses of the disease can be expected. PV occurs rarely with about 1 to 2 new cases per one million people.

In the case of the autoimmune diseases which form blisters subepidermally, the autoantibodies are directed against structural proteins in the region of the dermal-epidermal junction zone (DEJ). Said proteins are of great importance for the adhesion of the basal keratinocytes on the underlying dermis. In the case of this group of diseases, a distinction is made between bullous pemphigoid, anti-p200 pemphigoid, pemphigoid gestationis, mucous membrane pemphigoid, linear IgA dermatosis, lichen ruber pemphigoides, epidermolysis bullosa acquisita (EBA) and dermatitis herpetiformis.

Bullous pemphigoid (BP) is the most common subepidermally blistering autoimmune disease. It is characterized by bulging blisters on healthy or reddened skin that are formed because of detachment of the epidermis and that may be accompanied by severe itching as a preliminary sign. The blisters commonly occur on the trunk and on the thighs and arms. In 20 percent of patients, the mucous membranes also become involved. If the blisters burst, the wounds usually heal without scarring. BP is a relatively common autoimmune disease, with about 15 to 20 new cases per one million people.

After bullous pemphigoid, mucous membrane pemphigoid (MMP, a variant thereof is anti-laminin 332 MMP) is the second most common bullous autoimmune dermatosis. Clinically, MMP is a heterogeneous syndrome in which, as per the definition, the mucous membranes are predominantly affected. The oral and ocular mucous membranes are most commonly affected. Blistering lesions sometimes heal with scarring. If the conjunctivas are affected, this may lead to blindness.

The clinical picture of anti-p200 pemphigoid is variable, with the BP-similar type occurring most commonly. This disease is rarer than BP, and this may also be due to the fact that many of these patients are misdiagnosed as EBA or anti-laminin 332 mucous membrane pemphigoid because of their similar immunofluorescence pattern.

Epidermolysis bullosa acquisita (EBA) is a very rare subepidermal bullous autoimmune disease which is characterized by autoantibodies against type VII collagen. Clinically, a distinction can be made between the mechanobullous form and inflammatory variants (similar to BP or to mucous membrane pemphigoid).

It is difficult to distinguish between the diseases clinically or histologically. However, in the related art, a range of serological assays which allow a diagnosis in many cases have been described. In the case of PV, autoantibodies against the proteins desmoglein 1 and/or 3 occur. In the case of BP, it is possible to detect autoantibodies against the proteins BP180 and/or BP230 in almost all cases and even against laminin 332 in some cases.

Anti-p200 pemphigoid is characterized by autoantibodies against a protein of the dermal-epidermal junction zone that has an apparent molecular mass of about 200 kDa. Said protein was described in 2009 (Dainichi, T., Kurono, S., Ohyama, B., Ishii, N., Sanzen, N., Hayashi, M., Shimono, C., Taniguchi, Y., Koga, H., Karashima, T., Yasumoto, S., Zillikens, D., Sekiguchi, K., Hashimoto, T. (2009). Anti-laminin gamma-1 pemphigoid. 106(8): 2800-5) as laminin gamma-1. In addition, as part of epitope spreading, it is also possible to find antibodies against type VII collagen, BP180 or else against laminin 332.

What are used in this connection are especially ELISA and indirect immunofluorescence, but other immunobiochemical methods are also usable in principle. For example, the dermatology profile of EUROIMMUN Medizinische Labordiagnostika AG (EA 1490-1208-1 G), which encompasses BP180, NC16A-4X, BP230-CF, desmoglein 1, desmoglein 3, envoplakin and collagen type VII, is suitable.

The related art discloses diagnostic procedures, in particular indirect immunofluorescence with esophagus tissue sections from primates or ELISA with the recombinant autoantigens as substrate (cf. van Beek, N., Zilikens, D., and Schmidt, E. (2018): Diagnosis of autoimmune bullous diseases. *J. Dtsch. Dermatol. Ges.* 16(9), pages 1077-1091). A particularly reliable assay, in terms of diagnostics, for the detection of anti-laminin 332 mucous membrane pemphigoid can be carried out using immunofluorescence and recombinant laminin 332 (Goletz, S., Probst, C., Komorowski, L., Schlumberger, W., Fechner, K., van Beek, N., Holtsche, M. M., Recke, A., Yancey, K. B., Hashimoto, T., Antonicelli, F., Di Zenzo, G., Zillikens, D., Stöcker W., and Schmidt, E. (2018): Sensitive and specific assay for the serological diagnosis of anti-laminin 332 mucous membrane pemphigoid, *Br. J. Dermatol.*, DOI 10-1111/bjd.17202). The related art does not describe autoantibodies against laminin beta-4.

However, what becomes apparent is that the detection via laminin gamma-1 is not positive in all patients. In a western blot with recombinant forms of laminin gamma-1 and in an ELISA with the C-terminal domain of laminin gamma-1, it was possible to detect, respectively, 90% and 69% of the tested anti-p200 pemphigoid patients (Dainichi et al., 2009: Groth, S., Recke, A., Vafia. K., Ludwig, R. J., Hashimoto. T., Zillikens. D., Schmidt, E. (2011). Development of a simple enzyme-linked immunosorbent assay for the detection of autoantibodies in anti-p200 pemphigoid. Br J Dermatol. 164(1): 76-82).

The clinical course of anti-p200 pemphigoid is variable. In contrast to epidermolysis bullosa acquisita and bullous pemphigoid, what is concerned here is a relatively benign disease with a good therapeutic response. Therefore, it is of great clinical importance to differentiate between these diseases.

U.S. Pat. No. 6,682,911 discloses laminin 12 and preparations of isolated laminin 12 and of subunits thereof.

SUMMARY OF THE INVENTION

Against this background, there is a need for a detection procedure for anti-p200 pemphigoid that has higher diagnostic reliability, especially sensitivity. At the same time, there is the additional aim of improving the differentiability between the various blistering autoimmune diseases of the skin.

The present invention includes the following embodiments:

1. A polypeptide comprising laminin beta-4 or a variant thereof, preferably in recombinant and/or isolated form.

2. The polypeptide as described in embodiment 1, wherein the polypeptide is immobilized.

3. The carrier as described in embodiment 2, further comprising at least one antigen, preferably all the antigens, from the group comprising laminin gamma-1, laminin 332. BP180, BP230, desmoglein 1, desmoglein 3, envoplakin, gliadin and collagen type VII or variants thereof and split skin.

4. The carrier as described in embodiment 3, wherein the carrier is selected from the group comprising a glass slide, preferably slide for microscopy, even more preferably with a eukaryotic cell overexpressing laminin beta-4 or a variant thereof, a biochip, a microtiter plate, a lateral flow device, a test strip, a membrane, preferably a blot, more preferably a line blot, a chromatography column material and a bead, preferably a magnetic or fluorescent bead.

5. A therapeutically useful carrier comprising the polypeptide as described in either of embodiment 1 and 2, wherein the carrier allows the contacting of human blood with the polypeptide followed by the recirculation of the blood into the body of a patient, the carrier preferably being an apheresis apparatus.

6. An antibody, preferably autoantibody, against laminin beta-4, preferably in isolated form.

7. The use of the polypeptide, carrier or autoantibody as described in any of embodiments 1 to 6 for the diagnosis of a disease.

8. A method for producing a diagnostically or therapeutically useful carrier, comprising the step of coating the carrier with the polypeptide as described in embodiment 1.

9. A method for purifying an autoantibody, comprising the steps of
   a) contacting a liquid comprising the autoantibody with the polypeptide as described in embodiment 1 under conditions which allow the formation of a complex comprising the autoantibody and the polypeptide,
   b) isolating the complex from step a), and
   c) optionally detecting the complex from step a) or dissociating the complex isolated in step b) followed by removal of the autoantibody from the polypeptide.

10. A method comprising the step of detecting an autoantibody against laminin beta-4 in a sample.

11. A pharmaceutical composition comprising the polypeptide as described in embodiment 1 or a variant thereof, preferably together with a pharmaceutically acceptable carrier.

12. A kit comprising the polypeptide as described in either of embodiments 1 and 2 or the carrier as described in either of embodiments 3 and 4, wherein the kit contains one reagent or more than one reagent from the group comprising a wash solution, a calibrator solution, an antibody against laminin beta-4, and an agent for the detection of an autoantibody against laminin beta-4, preferably a secondary antibody.

13. The use of the polypeptide as described in embodiment 1, of the carrier as described in either of embodiments 3 and 4 or of an antibody, preferably autoantibody, against laminin beta-4 for the production of a kit or diagnostically or therapeutically useful carrier.

14. The method, use or kit as described in any of embodiments 7 to 10 and 12 to 13, wherein an autoantibody against laminin beta-4 is detected using a method selected from the group comprising immunodiffusion, immunoelectrophoresis, light scattering, agglutination, immunoassay with labeling such as that from the group comprising immunoassay with radioactive labeling, with enzymatic labeling, more preferably ELISA, with chemiluminescence labeling, more preferably electrochemiluminescence labeling, and with immunofluorescence labeling, preferably indirect immunofluorescence.

15. The use of the polypeptide as described in embodiment 1 or of the antibody as described in embodiment 6 for the determination of the capability, preferably capacity, of a diagnostic or therapeutic device or of a diagnostic or therapeutic reagent to bind an antibody against laminin beta-4.

16. The method as described in embodiment 10, wherein the autoantibody is detected in a tissue sample from a patient or with a carrier comprising laminin beta-4 or a variant thereof, preferably as described in embodiments 3 or 4.

DETAILED DESCRIPTION OF THE INVENTION

Figure 1:
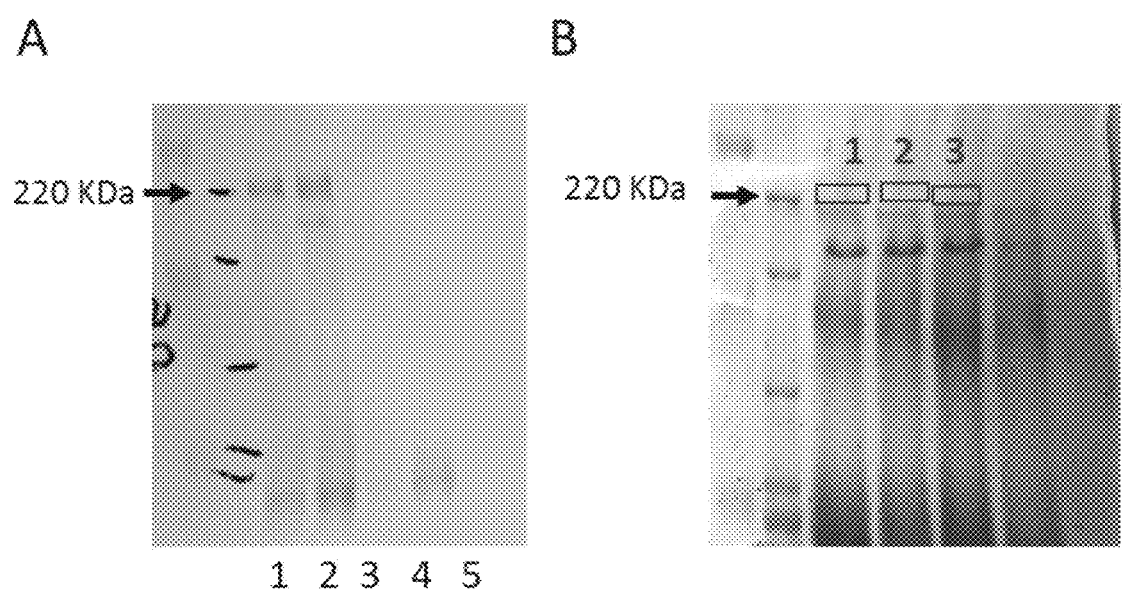
FIG. 1 shows an immunoprecipitation with anti-p200 pemphigoid patient IgG or serum without LAMC1 reactivity and extract of human dermis. A: Western blot analysis: detection of the immunoprecipitated proteins by incubation with an anti-p200 pemphigoid serum as primary antibody (dilution 1:50). Lane 1: anti-p200 IgG (purified) without LAMC1-cterm reactivity; lane 2: anti-p200 pemphigoid serum without LAMC1-cterm reactivity; lane 3: normal human IgG (purified); lane 4: normal human serum; lane 5: Gammabind G Sepharose on its own. B: Silver blue (Coomassie) staining of a gel containing the same samples as in A. Bands 1, 2 and 3 were cut out and subjected to an LC-MS/MS analysis. Laminin beta-4 was identified as possible autoantigen (bands 1 and 2).

In a first aspect, the object underlying the invention is achieved by a polypeptide comprising laminin beta-4 or a variant thereof, preferably in recombinant and/or isolated form.

In a preferred embodiment, the polypeptide is immobilized.

In a second aspect, the object is achieved by a carrier comprising the polypeptide according to the invention, and further comprising at least one antigen, preferably all the antigens, from the group comprising laminin gamma-1, BP180, BP230, desmoglein 1, desmoglein 3, envoplakin, deamidated gliadin, laminin 332 and collagen type VII or variants thereof.

In a preferred embodiment, the carrier is selected from the group comprising a glass slide, preferably slide for microscopy, a biochip, a microtiter plate, a lateral flow device, a test strip, a membrane, preferably a blot, more preferably a line blot, a chromatography column material and a bead, preferably a magnetic or fluorescent bead.

In a third aspect, the object is achieved by a therapeutically useful carrier comprising the polypeptide according to the invention, wherein the carrier allows the contacting of human blood with the polypeptide followed by the recirculation of the blood into the body of a patient, the carrier preferably being an apheresis apparatus.

In a fourth aspect, the object is achieved by an antibody, preferably autoantibody, against laminin beta-4, preferably in isolated form.

In a fifth aspect, the object is achieved by the use of the polypeptide, carrier or autoantibody according to the invention for the diagnosis of a disease.

In a sixth aspect, the object is achieved by a method for producing a diagnostically or therapeutically useful carrier, comprising the step of coating the carrier with the polypeptide according to the invention.

In a seventh aspect, the object is achieved by a method for purifying an autoantibody, comprising the steps of a) contacting a liquid comprising the autoantibody with the polypeptide according to the invention under conditions which allow the formation of a complex comprising the autoantibody and the polypeptide, b) isolating the complex from step a), and c) optionally detecting the complex from step a) or dissociating the complex isolated in step b) followed by removal of the autoantibody from the polypeptide.

In an eighth aspect, the object is achieved by a method comprising the step of detecting an autoantibody against laminin beta-4 in a sample.

In a ninth aspect, the object is achieved by a pharmaceutical composition comprising the polypeptide according to the invention or a variant thereof, preferably together with a pharmaceutically acceptable carrier.

In a tenth aspect, the object is achieved by a kit comprising the polypeptide according to the invention or the carrier according to the invention, wherein the kit contains one reagent or more than one reagent, preferably all the reagents, from the group comprising a wash solution, a calibrator solution, an antibody against laminin beta-4, and an agent for the detection of an autoantibody against laminin beta-4, preferably a secondary antibody.

In an eleventh aspect, the object is achieved by the use of the polypeptide according to the invention, of the carrier according to the invention or of an antibody, preferably autoantibody, against laminin beta-4 for the production of a kit or diagnostically or therapeutically useful carrier.

In a preferred embodiment, an autoantibody against laminin beta-4 is detected using a method selected from the group comprising immunodiffusion, immunoelectrophoresis, light scattering, agglutination, immunoassay with labeling such as that from the group comprising immunoassay with radioactive labeling, with enzymatic labeling, more preferably ELISA, with chemiluminescence labeling, more preferably electrochemiluminescence labeling, and with immunofluorescence labeling, preferably indirect immunofluorescence.

In a twelfth aspect, the object is achieved by the use of the polypeptide according to the invention or of the antibody according to the invention for the determination of the capability, preferably capacity, of a diagnostic or therapeutic device or of a diagnostic or therapeutic reagent to bind an antibody against laminin beta-4.

The present invention is based on the surprising finding by the inventors that an autoantibody against laminin beta-4 exists and can be specifically detected in patients who suffer from anti-p200 pemphigoid.

The inventors further found that the detection of said autoantibody increases the sensitivity of the serological diagnostic assay for anti-p200 pemphigoid. It can be detected in some patients in whom it is not possible to detect the autoantibody against laminin gamma-1, which autoantibody was hitherto considered to be of sole importance.

Laminins are trimeric basal membrane proteins which consist of alpha, beta and gamma chains. Laminin beta-4 is a beta chain. Laminins are involved in many physiological functions such as, for example, cell adhesion, migration, differentiation, neuronal development and in the regulation of gene expression.

Choi et al. (2015) observed a reduced expression of laminin beta-4 in cancer tissue of the stomach and intestine. They identified somatic laminin beta-4 mutations in cancer tissue that possibly contributed to a reduced expression of laminin beta-4 (Choi, M. R., An, C. H., Yoo, N. J., Lee. S. H. Laminin gene LAMB4 is somatically mutated and expressionally altered in gastric and colorectal cancers. APMIS 123: 65-71, 2015). Moreover, reduced levels of laminin beta-4 might also play a role in diverticulitis (Coble J L, Sheldon K E, Yue F, Salameh T J. Harris L R III, Deiling S, Ruggiero F M, Eshelman M A, Yochum G S, Koltun W A, Gerhard G S. Broach J R. Identification of a rare LAMB4 variant associated with familial diverticulitis through exome sequencing. Hum Mol Genet. 2017, 26(16): 3212-3220).

The present invention provides a polypeptide comprising a mammalian laminin beta-4, preferably from humans, simians, cattle, sheep or pigs and particularly preferably from humans.

In a preferred embodiment, laminin beta-4 is the polypeptide which is encoded by the database codes (BC140804), preferably SEQ ID NO 27, or a variant thereof. In this application, all the cited database codes represent the Uniprot database or other databases, more precisely the version thereof on the filing date of said application or its earliest priority application. In a further preferred embodiment, the further antigens have the sequences respectively indicated between parentheses: laminin gamma-1 (LAMC1 P11047), laminin 332 selected from the group comprising LAMA3 (Q16787), LAMB3 (Q13751) and LAMC2 (Q13753), BP180 (Q9UMD9). BP230 (SEQ ID NO8 from EP3260864, listed here as SEQ ID NO 28), desmoglein 1 (Q02413), desmoglein 3 (P32926), envoplakin (Q92817), gliadin, preferably selected from the group comprising LGQQQPFPPQQPYPQPQPFPSQQPY (SEQ ID NO 29), QLQPFPQPELPYPQPQS (SEQ ID NO 30) and QQLPQPEQPQQSFPEQERPF (SEQ ID NO 31), and collagen type VII (Q02388) or variants thereof.

However, it is possible to carry out the teaching according to the invention not only by using polypeptides or nucleic acids, more precisely a polypeptide comprising the wild-type sequence of laminin beta-4 or a nucleic acid coding therefor, which have the exact sequences stated expressly or implicitly in this application, but also by using variants of such polypeptides or nucleic acids.

In a preferred embodiment, the term "variant", as used herein, can mean at least one fragment or one full-length sequence, more precisely one or more than one amino acid sequence or nucleic acid sequence, which is truncated at one end or both ends by at least one or more than one amino acid relative to the full-length sequence. Such a fragment comprises or encodes a peptide containing at least 6, 7, 8, 10, 12, 15, 20, 25, 50, 75, 100, 300, 400, 600, 800, 1000 or 1200 successive amino acids of the original sequence or a variant thereof. The total length of the variant can be at least 6, 7, 8, 9, 10, 11, 12, 20, 25, 30, 40, 50, 60, 70, 80, 90, 100, 200, 300, 400, 500, 600, 800, 1000, 1200, 1500, 1800 or more amino acids. A particularly preferred fragment is selected from the group comprising SEQ ID NO 8, SEQ ID NO 9, SEQ ID NO 10, SEQ ID NO 11, SEQ ID NO 12, SEQ ID NO 13 and SEQ ID NO 14 and variants thereof.

In a further preferred embodiment, the term "variant" means not only at least one fragment, but also a polypeptide or fragment thereof which comprises amino acid sequences which are at least 40%, 50%, 60%, 70%, 75%, 80%, 85%, 90%, 92%, 94%, 95%, 96%, 97%, 98% or 99% identical to the amino acid sequence or the fragment thereof to which express reference has been made, with deletion or substitution of amino acids other than those essential for biological activity, for example the capabilities of an antigen of binding to the (auto)antibody or the folding or structure of the polypeptide, and/or conservative substitution of one or more than one such essential amino acid and/or addition of amino acids such that the biological activity of the polypeptide is maintained. The related art comprises various methods which can be used for aligning two given nucleic acid or amino acid sequences and for calculating the degree to which they are identical; see, for example, Arthur Lesk (2008), Introduction to bioinformatics, Oxford University Press, 2008, 3rd edition. In a preferred embodiment, the Clustal W software is used with use of the basic settings (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948).

In a preferred embodiment, the variant is a linear, non-folded polypeptide which is optionally denatured.

In a preferred embodiment, the polypeptide and variants thereof can additionally contain chemical modifications, for example isotopic labels, or covalent modifications such as a glycosylation, phosphorylation, acetylation, decarboxylation, citrullination, methylation.

Is hydroxylation and the like. A person skilled in the art is familiar with methods for modifying polypeptides. Any modification is designed such that it does not cancel the biological activity of the variant.

Furthermore, variants can also be generated by N-terminal and/or C-terminal fusion with other polypeptides, peptides or amino acids or variants thereof and can comprise active parts or domains, for example having a sequence identity of at least 70%, 75%, 80%, 85%, 90%, 92%, 94%, 95%, 96%, 97%, 98% or 99% when they are aligned with the active part of the wild-type sequence, the term "active part", as used herein, meaning the amino acid sequence which is shorter than the full-length amino acid sequence, or in the case of a nucleic acid sequence encodes less than the full-length amino acid sequence, and/or is a variant of the natural sequence, but contains at least some of the biological activity. Fused-on sequences are configured such that they do not interfere with the binding of the autoantibody to the laminin beta-4 or the variant thereof, especially not to the epitopes which are comprised by the sequences SEQ ID NO 8, SEQ ID NO 9, SEQ ID NO 10, SEQ ID NO 11, SEQ ID NO 12, SEQ ID NO 13 and SEQ ID NO 14 and variants thereof. A tag, for example from the group comprising GST, His, MBP and FLAG, which is fused on directly or via a flexible linker at the N-terminus and/or C-terminus is suitable for example.

In a preferred embodiment, the term "variant" encompasses nucleic acids of the complementary strand which hybridizes to the reference nucleic acid or wild-type nucleic acid under stringent conditions. The stringency of hybridization reactions can be easily determined by a person skilled in the art and is generally an empirical calculation which depends on the probe length, the wash temperatures and the salt concentration. It is generally the case that longer probes requires higher temperatures for specific annealing, whereas shorter probes require a less high temperature. Hybridization generally depends on the capability of a denatured DNA to hybridize once again to the complementary strand in an environment below its melting temperature. The higher the degree of the required homology between the probe and the sequence capable of hybridization, the higher the relative temperature that can be used. As a result, higher relative temperatures would tend to shape the reaction conditions more stringently, whereas a lower temperature brings this about to a lesser degree. For additional details and explanations in relation to stringency and hybridization reaction, see Ausubel, F. M. (1995). Current Protocols in Molecular Biology. John Wiley & Sons, Inc. Furthermore, a person skilled in the art can follow the instructions found in the manual from Boehringer Mannheim GmbH (1993) (The DIG System Users Guide for Filter Hybridization. Boehringer Mannheim GmbH, Mannheim, Germany) and in Liebl, W., Ehrmann, M., Ludwig, W., and Schleifer, K. H. (1991) International Journal of Systematic Bacteriology 41: 255-260, in relation to the question of how DNA sequences can be identified by means of hybridization. In a preferred embodiment, stringent conditions are applied to every hybridization, i.e. hybridization occurs when the probe is 70% identical or higher to the target sequence. Probes having a lower degree of identity with respect to the target sequence can hybridize, but such hybrids are unstable and are removed in a wash step under stringent conditions, for example by lowering the salt concentration to 2×SSC or optionally and then subsequently 0.5×SSC, while the temperature is, with increasing preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. In a particularly preferred embodiment, the temperature is about 64° C.-68° C. or preferably 66° C.-68° C. It is possible to adjust the salt concentration to 0.2×SSC or even 0.1×SSC. Nucleic acid sequences having a degree of identity with respect to the reference sequence or wild-type sequence of at least 70%, 80%, 90%, 91%, 92%, 93%, 94%, 95%, 96%, 97%, 98%, 99% can be isolated. In a preferred embodiment, the term "variant of a nucleic acid sequence", as used herein, means any nucleic acid sequence encoding the same nucleic acid sequence and variants thereof as the reference nucleic acid sequence in line with the degeneracy of the genetic code.

The variant of the polypeptide exhibits biological activity. In a preferred embodiment, this is the capability of binding to an autoantibody against laminin beta-4, as is found in a patient suffering from an autoimmune disease associated with such an autoantibody, preferably anti-p200 pemphigoid. It is possible to clarify whether, for example, a variant of laminin beta-4 has such biological activity by detecting whether said variant binds to an autoantibody from a patient sample, preferably by western blotting and/or indirect immunofluorescence, preferably indirect immunofluorescence, using recombinant proteins as described in the examples. Moreover, the inventors have identified the sequences SEQ ID NO 8, SEQ ID NO 9, SEQ ID NO 10, SEQ ID NO 11, SEQ ID NO 12, SEQ ID NO 13 and SEQ ID NO 14, which are reactive toward an autoantibody against laminin beta-4. Variants of laminin beta-4 to which such an autoantibody binds can thus be easily generated by the generation of an epitope from the laminin beta-4 sequence that comprises at least one of these sequences, it being optionally possible to generate additional variants by conservative substitutions of amino acid residues.

The polypeptide according to the invention can be provided in any form and any purification stage, from liquid samples, tissues or cells comprising the polypeptide in an endogenous form, more preferably cells overexpressing the polypeptide, crude or enriched lysates of such cells, up to purified and/or isolated polypeptide which is optionally substantially pure. In a preferred embodiment, the polypeptide is a native polypeptide, the term "native polypeptide", as used herein, describing a folded polypeptide, more preferably a folded polypeptide purified from tissues or cells, more preferably from mammalian cells or tissues, optionally from nonrecombinant tissues or cells. In a further preferred embodiment, the polypeptide is a recombinant protein, the term "recombinant", as used herein, meaning a polypeptide which was produced in any phase of the production process using gene-technology methods, for example by fusion of a nucleic acid encoding the polypeptide to a strong promoter for overexpression in cells or tissues or by modification of the polypeptide sequence itself. A person skilled in the art is familiar with methods for modifying nucleic acids and polypeptides encoded thereby by means of gene technology (e.g., described in Sambrook, J., Fritsch, E. F. and Maniatis. T. (1989), Molecular Cloning, CSH or in Brown T. A. (1986), Gene Cloning—an introduction, Chapman & Hall), and also with methods for producing and purifying native or recombinant proteins (e.g., the handbooks "Strategies for Protein Purification". "Antibody Purification", "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure when at least 60%, 70%, 80%, 90%, 95% or 99% of the total polypeptide in the relevant sample consists of the polypeptide, as assessed by means of SDS-polyacrylamide gel electrophoresis followed by Coomassie Blue staining and estimation with the naked eye. If the polypeptide according to the invention is provided in the form of a tissue, it is preferred that the tissue is a mammalian tissue, for example tissue from humans, from primates, from donkeys, from goats, from horses, from sheep, from pigs or from cows, preferably skin tissue. If the polypeptide is provided in the form of a recombinant cell, it is preferred that the recombinant cell is a eukaryotic cell such as a yeast cell, more preferably a cell from a multicellular eukaryote such as a plant, a mammal, frog or insect, most preferably from a mammal, for example rat, human, primate, donkey, mouse, goat, horse, sheep, pig or cow.

The polypeptide for carrying out the teaching according to the invention is preferably of such a nature that it comprises at least one epitope which is recognized by the autoantibody which binds to laminin beta-4, or that it binds specifically to said autoantibody. The epitope is preferably an epitope which is only recognized by such an autoantibody and not by other antibodies, such as autoantibodies against laminin gamma-1, BP180, BP230, desmoglein 1, desmoglein 3, envoplakin, gliadin, laminin 332 or collagen type VII. In such an embodiment, such an epitope comprises a segment of 6, 7, 8, 9, 10, 11, 12, 20, 25, 30, 40, 50, 60, 70, 80, 90, 100 or more, preferably at least 9, but not more than 16, successive amino acids from laminin beta-4. A person skilled in the art is familiar with guidelines for designing peptides having sufficient immunogenicity, for example as have been described in Jackson et al. (Jackson, D. C., Fitzmaurice, C. J., Brown, L. E., Zeng, W. (1999), Preparation and properties of totally synthetic immunogenes, Vaccine, volume 18, issues 3-4, September 1999, pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173).

The polypeptide according to the invention, which encompasses laminin beta-4 or a variant thereof, can be provided in any conformation to carry out the present invention. For example, the polypeptide can be a substantially unfolded or partially or completely folded polypeptide. In a preferred embodiment, the polypeptide is folded in the sense that the epitope(s) required for the binding to the autoantibody according to the invention assume(s), in its or their entirety, the folding which is assumed by the native protein in its natural environment. A person skilled in the art in the field is familiar with methods which can be used to determine whether the polypeptide is folded, and if it is folded, what structure it assumes, for example limited proteolysis, NMR spectroscopy, CD spectroscopy or X-ray crystallography (see, for example, Banaszak L. J. (2008), Foundations of Structural Biology, Academics Press, or Teng Q. (2013), Structural Biology: Practical Applications, Springer), preference being given to using CD spectroscopy.

The polypeptide according to the invention can be a fusion protein which comprises, at the C-terminus and/or N-terminus, amino acids and/or amino acid sequences other than those from laminin beta-4, especially a C-terminal or N-terminal tag, preferably a C-terminal tag, which, in a preferred embodiment as used herein, comprises an additional sequence motif or a polypeptide that has some biological or physical function and can, for example, be realized for the purification, immobilization, precipitation or identification of the polypeptide according to the invention.

In a more preferred embodiment, the tag is a sequence or domain which is capable of binding specifically to a ligand, for example a tag selected from the group comprising His-tags, thioredoxin, maltose-binding protein, glutathione S-transferase, a fluorescence tag, for example from the group comprising green fluorescent protein (GFP).

The polypeptide according to the invention can be an immobilized polypeptide. In a preferred embodiment, the term "immobilized", as used herein, means a molecule which is bound to a solid carrier which is insoluble in an aqueous solution, more preferably via a covalent bond, electrostatic interaction, encapsulation or inclusion, for example by denaturation of a globular polypeptide in a gel, or via hydrophobic interaction, most preferably via one or more than one covalent bond. Various suitable carriers, for example paper, polystyrene, metal, silicone or glass surfaces, microfluidic channels, membranes, beads such as magnetic beads, chromatography column media, biochips, polyacrylamide gels and the like, are described in the literature, for example in Kim, D., and Herr, A. E. (2013), Protein immobilization techniques for microfluidic assays, Biomicrofluidics 7(4), 041501. In this way, the immobilized molecule together with the insoluble carrier can be easily separated from an aqueous solution in a simple manner, for example by filtration, centrifugation or decanting. An immobilized molecule can be reversibly or irreversibly immobilized. For example, the immobilization is reversible when the molecule interacts with the carrier via an ionic interaction which can be masked by addition of a high concentration of a salt or when the molecule is bound via a cleavable covalent bond such as a disulfide bridge which can be cleaved by addition of thiol-containing reagents. In contrast, the immobilization is irreversible when the molecule is attached to the carrier via a covalent bond which cannot be cleaved in aqueous solution, for example a bond which is formed by reaction of an epoxide group and an amino group, as is commonly used for binding lysine side chains to affinity columns. The protein can be indirectly immobilized, for example by immobilization of an antibody or some other unit having affinity for the molecule, followed by formation of a complex, with the effect that the molecule-antibody complex is immobilized. Various options for immobilizing to molecules are described in the literature, for example in Kim, D., and Herr, A. E. (2013), Protein immobilization techniques for microfluidic assays, Biomicrofluidics 7(4), 041501. In addition, various reagents and kits for immobilization reactions are commercially available, for example from Pierce Biotechnology.

It is necessary that the sample used for diagnosis by means of the detection of autoantibodies according to the present invention comprises antibodies, which are also referred to as immunoglobulins. Typically, the sample of a body fluid comprises a representative selection of the entirety of immunoglobulins of the patient. However, after provision, the sample can be subjected to further processing steps, which can encompass fractionation, centrifugation, enrichment or isolation of the entirety of immunoglobulins or of a certain immunoglobulin class of the patient and can influence the relative distribution of the immunoglobulins of the various classes.

The reagents, devices, methods and uses that are described in this application can be used for the diagnosis of a disease. In a preferred embodiment, the disease is an autoimmune disease, even more preferably an autoimmune disease of the skin and/or of the eye. Such diseases are distinguished by an overlapping spectrum of symptoms, including blisters, redness and bleedings and also secondary diseases such as an infection of the affected sites. Accordingly, what is also possible is a diagnosis, diagnostic differentiation or indirect diagnosis of an infection of the skin, of the eye or of an allergy. The autoimmune disease is particularly preferably one from the group comprising anti-p200 pemphigoid, anti-laminin 332 mucous membrane pemphigoid, epidermolysis bullosa acquisita, BP and PV.

In a preferred embodiment, the term "diagnosis", as used herein, means any procedure which is aimed at obtaining information which is used to estimate whether a patient suffers from a certain disease or disorder in the past, at the time of diagnosis or in the future and/or has a higher probability of suffering than the average comparative person, preferably with similar symptoms, in order to find out how the disease is progressing or is likely to progress in the future or in order to evaluate the response of a patient to a certain treatment, for example the administration of immunosuppressants. In other words, the term "diagnosis" encompasses not only the making of a diagnosis, but also the prognostication and/or the monitoring of the course of a disease or disorder.

In many cases, mere detection, in other words determining whether detectable concentrations of the antibody are present in the sample or not, is sufficient for diagnosis. If the autoantibody can be detected, this is a piece of information which is important for the diagnosis by the physician and indicates that there is an increased probability of the patient suffering from the disease. Preferably, said piece of information, or a signal containing said piece of information, can be communicated to a patient or the physician treating said patient in written form, by telephone or by electronic means, for example via the Internet, for example as an e-mail. The piece of information enables the physician in a particularly preferred embodiment to draw a diagnostically useful conclusion and optionally to take it into consideration in the treatment of the patient. In a preferred embodiment, the autoantibody is considered detectable if it can be detected using one or more than one method selected from the group comprising immunoprecipitation, indirect immunofluorescence, ELISA or blot, preferably blot. The experimental details are as described in the experimental section of this application or as described in textbooks or practical protocols as were available on the earliest priority date of this application. In a preferred embodiment, the relative concentration of the antibody in serum is determined in comparison with the concentration found in an average normal person. While it is sufficient in many cases to establish whether the autoantibodies are present or detectable in the sample, the method for obtaining useful information for diagnosis can comprise determination of whether the concentration is at least 0.1, preferably 0.2, 0.5, 1, 2, 5, 10, 20, 25, 50, 100, 200, 500, 1000, 10 000 or 100 000, times higher than the concentration found in the normal healthy person. In a preferred embodiment, the relative concentration of the autoantibody is determined using one or more than one method selected from the group comprising semiquantitative immunoprecipitation, semiquantitative indirect immunofluorescence, ELISA or line blot, preferably ELISA.

The present invention provides a complex comprising an antibody, preferably autoantibody, which binds against the polypeptide according to the invention. It is possible for such a complex to be used or to be detected as part of a method for diagnosing a disease. A liquid sample comprising antibodies from a patient can be used for carrying out the method in which an autoantibody against laminin beta-4 is to be detected. Such a liquid sample can encompass any body fluid comprising a representative selection of antibodies from the person, preferably a sample comprising antibodies of immunoglobulin class IgG from the person. For example, a sample can be cerebrospinal fluid, blood or blood serum, lymph, interstitial fluid and is to preferably serum or cerebrospinal fluid, more preferably serum.

The step of contacting a liquid sample comprising antibodies with the polypeptide according to the invention can be carried out by incubation of an immobilized form of the polypeptide in the presence of the sample, of the antibody-comprising sample, under conditions which are compatible with the formation of a complex comprising the polypeptide and an antibody, preferably autoantibody, which binds to the polypeptide according to the invention. The liquid sample in which antibodies which bind against the polypeptide(s) according to the invention are depleted can subsequently be removed, followed by one or more than one wash step. Lastly, the complex comprising the antibody or the antibodies and the polypeptide or the polypeptides can be detected. In a preferred embodiment, the term "conditions which are compatible with the formation of the complex" means conditions which allow the formation of the specific antigen-antibody interactions for the assembly of the complex comprising the polypeptide and the antibody. In a preferred embodiment, such conditions can comprise the incubation of the polypeptide in a sample diluted 1:100 in PBS buffer at 25° C. for 30 minutes. In a preferred embodiment, the term "autoantibody", as used herein, means an antibody which binds specifically to an endogenous molecule of the animal, preferably mammal, which produces the autoantibody itself, with the concentration of the autoantibody being elevated preferably compared to the average of any antibodies which bind against such an endogenous molecule, preferably compared to a healthy person. In a most preferred embodiment, the autoantibody is an autoantibody against laminin beta-4.

The method according to the invention is preferably an in vitro method.

In a preferred embodiment, the detection of the complex for the prognosis, diagnosis, methods or assay kit according to the present invention comprises the use of a method selected from the group comprising immunodiffusion assays, immunoelectrophoresis assays, light-scattering immunoassays, agglutination assays, immunoassays with labels such as those from the group comprising radiolabeled immunoassays, enzyme immunoassays, preferably ELISA, chemiluminescence immunoassays and immunofluorescence assays, preferably indirect immunofluorescence assays. A person skilled in the art is familiar with such methods, and the) are described in the related art, for example in Zane, H. D. (2001), Immunology—Theoretical & Practical Concepts in Laboratory Medicine, W. B. Saunders Company, particularly in chapter 14.

Alternatively, a tissue sample, i.e., preferably a sample comprising tissue comprising the polypeptide according to the invention, can be used instead of a liquid sample, especially split skin, which can be prepared as described in the related art (Zillikens, D., Kawahara, Y., Ishiko, A., Shimizu, H., Mayer, J., Rank, C. V., Liu, Z., Giudice, G. J., Tran, H. H., Marinkovich. M. P., Brocker, E. B., and Hashimoto, T. A novel subepidermal blistering disease with autoantibodies to a 200-kDa antigen of the basement membrane zone. J Invest Dermatol, 1996, 106(6): pp. 1333-8). The tissue sample preferably originates from a tissue comprising endogenous laminin beta-4, preferably expressing the polypeptide to an increased extent compared to the average tissue in the relevant organism, preferably the human body. Such a sample, which can then be present in the form of a tissue section fixed on a carrier, for example a slide for microscopic analyses, can then be contacted with the antibody according to the invention, preferably autoantibody which binds against the polypeptide according to the invention. The antibody is preferably labeled in order to allow distinguishing of endogenous autoantibody which binds against the polypeptide according to the invention, and so it is possible to detect and optionally quantify newly formed complexes with autoantibodies from a subsequently contacted sample that compete with the first antibody. If the number of the newly formed complexes is higher than the number found with a sample from a healthy person, it is likely that the person from whom the investigated sample was obtained is suffering from the disease.

Any data showing the presence or absence of the complex comprising the antibody and the polypeptide according to the invention can be compared with reference data. For example, the detection of the complex indicates that the patient from whom the analyzed sample was obtained suffered from a disease, is suffering from it or is likely to suffer from the disease in the future. If a patient has been previously diagnosed and the method is carried out again to obtain diagnostically relevant information, the amount of the complex obtained in both passes can be correlated in order to find out the progression of the disease and/or the success of a treatment. If, for example, it is found that the amount of the complex has increased, this suggests that the disease is progressing, is likely to manifest itself in the future and/or that an attempted treatment is unsuccessful and vice versa. The first detection of the complex indicates that the patient from whom the sample originates is suffering from a high or increased risk of developing the disease in the future.

In a preferred embodiment, a microtiter plate, a membrane, a blot such as dot blot or line blot is used in order to carry out the diagnostic method according to the invention. A person skilled in the art is familiar with the experimental setup, and said setup is described in the related art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540).

In a further preferred embodiment, what is envisaged for the prognosis, diagnosis, methods or kit as per the teaching according to the invention is the use of indirect immunofluorescence. A person skilled in the art is familiar with such techniques and the preparation of suitable samples, and these are described in the related art (U.S. Pat. No. 4,647, 543; Voigt, J., Krause, C., Rohwäder, E., Saschenbrecker, S., Hahn, M., Danckwardt, M., Feirer, C., Ens, K., Fechner, K., Barth, E., Martinetz, T., and Stocker, W. (2012), Automated Indirect Immunofluorescence Evaluation of Antinuclear Autoantibodies on HEp-2 Cells, Clinical and Developmental Immunology, vol. 2012, doi:10.1155/2012/65105: Bonilla. E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Libeck, Germany.

As per the teaching according to the invention, what is provided is an antibody, preferably an autoantibody, which binds against the inventive polypeptide used for the diagnosis of a disease. A person skilled in the art in the field is familiar with methods for purifying antibodies, for example those described in Hermanson, G. T., Mallia, A. K., and Smith, P. K. (1992). Immobilized Affinity Ligand Techniques, San Diego: Academic Press. In brief, an antigen which binds specifically against the autoantibody of interest, the antigen being the polypeptide according to the invention, is immobilized and used in order to purify the autoantibody of interest from a suitable source via affinity chromatography. A liquid sample comprising antibodies from a patient suffering from a neurological disorder or disease which is associated with the occurrence of the autoantibody can be used as the source.

According to the invention, what is provided is an antibody, for example an autoantibody, which is capable of binding specifically to the polypeptide according to the invention. In a preferred embodiment, the term "antibody", as used herein, means any immunoglobulin-based binding units, preferably a unit comprising at least one heavy chain and one light chain of an immunoglobulin, encompassing, if not limited to, monoclonal and polyclonal antibodies and also variants of an antibody, especially fragments, with the binding units being capable of binding against the corresponding antigen, more preferably of binding specifically thereto. In a preferred embodiment, the term "bind specifically", as used herein, means that the bond is stronger than a binding reaction characterized by a dissociation constant which is $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7. The antibody is preferably recombinant and/or isolated. The antibody detected or provided according to the invention preferably binds specifically to an epitope from the sequence SEQ ID NO 27 comprising one or more than one sequence from the group comprising the sequences SEQ ID NO 8, SEQ ID NO 9, SEQ ID NO 10, SEQ ID NO 11, SEQ ID NO 12, SEQ ID NO 13 and SEQ ID NO 14. The autoantibody is preferably an IgG antibody.

The antibody can be part of an autoantibody preparation which is heterogeneous or can be a homogeneous autoantibody, a heterogeneous preparation comprising a multiplicity of different autoantibody species, as can be obtained by preparation from the sera from human donors, for example by affinity chromatography using the immobilized antigen, for the purification of any autoantibody which is capable of binding to the antigen. The antibody can be glycosylated or non-glycosylated. A person skilled in the art in the field is familiar with methods which can be used for the identification, production and purification of antibodies and variants thereof, for example those described in EP 2 423 226 A2 and references therein. The antibody can be used by itself or in combination as diagnostic agent, for example in a complex with the polypeptide according to the invention.

The present invention provides a method for isolating an antibody, preferably an autoantibody, which binds against the polypeptide according to the invention, comprising the steps of a) contacting a sample comprising the antibody with the polypeptide according to the invention such that a complex is formed, b) isolating the complex which is formed in a), c) dissociating the complex which was isolated in step b), and d) removing the antibody from the polypeptide according to the invention. A sample from a patient suffering from anti-p200 pemphigoid can be used as the source of the autoantibody. Suitable methods are described in the related art, for example in the handbooks "Affinitätschromatografie" [Affinity Chromatography], "Strategies for Protein Purification" and "Antibody Purification" (2009/2010), published by GE Healthcare Life Sciences, and in Philips, Terry, M., Analytical techniques in immunochemistry, 1992, Marcel Dekker, Inc.

The invention provides a pharmaceutical composition comprising the polypeptide according to the invention, the composition preferably being suitable for administration to a subject, preferably a mammalian subject, more preferably a human. Such a pharmaceutical composition can comprise a pharmaceutically acceptable carrier. The pharmaceutical composition can, for example, be administered orally, parenterally, via an inhalation spray, topically, via eye drops, rectally, nasally, buccally, vaginally or via an implanted reservoir, the term "parenterally", as used herein, encompassing subcutaneous, intracutaneous, intravenous, intramuscular, intraarticular, intrasynovial, intrasternal, intrathecal, intralesional and intracranial injection or infusion techniques. The pharmaceutical composition can be provided in suitable dosage forms, for example capsules, tablets and aqueous suspensions and solutions, preferably in sterile form. It can be used in a treatment method, the method comprising the administration of an effective amount of the polypeptide according to the invention to a subject.

Within the scope of protection of the present invention, what is provided is a medical or diagnostic device comprising, preferably coated with, a reagent for the detection of the (auto)antibody according to the invention and/or the polypeptide according to the invention. Preferably, such a medical or diagnostic device comprises the polypeptide according to the invention in a form which allows the contacting of the polypeptide with an aqueous solution, more preferably the liquid human sample, in a simple manner. In particular, the polypeptide according to the invention can be immobilized on the surface of a carrier, preferably selected from the group comprising glass plates or glass slides, microscope slides, biochips, microtiter plates, beads, for example magnetic beads, apheresis devices, chromatography columns, membranes or the like. Exemplary medical devices encompass line blots, microtiter plates, glass slides for microscopy, beads, preferably magnetic beads, and biochips. In addition to the polypeptide according to the invention, the diagnostic device can comprise further polypeptides, for example positive or negative controls such as samples which contain or do not contain an antibody against the polypeptide of interest, or other known antigens which bind against autoantibodies of diagnostic value, especially with regard to other diseases which are associated with one or more than one identical or similar symptom.

Within the scope of protection of the present invention, what is also provided is a therapeutic device comprising, preferably coated with, laminin beta-4 or a variant thereof, the nature of which is such that the autoantibody against laminin beta-4 can be removed from the blood of a patient with minimal change to the blood composition and especially with removal of as few essential components as possible. This can be an apheresis device, preferably for plasmapheresis. Suitable reagents and methods are described in EP17001759.4 and in WO2007/085240, which are incorporated herein in their entirety by reference. In the related art, it is already described that specific immunoadsorption for the treatment of bullous pemphigoid is promising (Mersmann et al., Arch Dermatol Res 2015: "Immunoadsorber for specific apheresis of autoantibodies in the treatment of bullous pemphigoid"). Preferably, the device is sterilized in the sense that incoming and outgoing blood only comes into contact with sterilized components.

As per the teaching according to the invention, what is provided is a kit, preferably for the diagnosis of a disease. Such a kit can comprise instructions describing in detail how the kit is to be used and also the carrier according to the invention as means for the contacting of the polypeptide according to the invention with a body fluid sample from a subject, preferably a human subject. Furthermore, the kit can comprise a positive control, for example a batch of autoantibody or recombinant antibody that is known to bind against the peptide according to the present invention, or a diluted sample from a patient comprising the autoantibody. The kit can contain a negative control, for example a protein having no detectable affinity for the polypeptide according to the invention, such as bovine serum albumin, or a sample from a healthy individual. Such a kit can comprise one or more than one standard solution of the antibody for the generation of a calibration curve, also referred to as calibrator, it being possible for the antibody to be a recombinant and/or monoclonal antibody or the diluted antibody from a sample from a patient, preferably against an epitope from the group comprising SEQ ID NO 8, SEQ ID NO 9, SEQ ID NO 10, SEQ ID NO 11, SEQ ID NO 12, SEQ ID NO 13 and SEQ ID NO 14. The kit can furthermore comprise a secondary antibody, preferably having a detectable label, which recognizes an autoantibody against laminin beta-4, preferably a secondary antibody which recognizes IgG antibodies.

In a preferred embodiment, the kit comprises a means for the detection of an autoantibody which binds against the polypeptide according to the invention, preferably by detection of a complex comprising the polypeptide according to the invention and an antibody which binds against the polypeptide according to the invention. Such a means is preferably an agent which binds against the complex and modifies the complex or bears a label which makes the complex detectable. For example, such a means can be a labeled antibody which binds against the polypeptide at a binding site differing from the binding site to which the primary autoantibody binds or which binds against a constant region of the primary antibody. Alternatively, the agent can be a secondary antibody against laminin beta-4 that binds against the constant region of the autoantibody, preferably a secondary antibody which is specific for mammalian antibodies of the IgG class. A multiplicity of methods and means for the detection of such a complex is described in the related art, for example in Philips, Terry. M., Analytical techniques in immunochemistry, 1992. Marcel Dekker, Inc.

The polypeptide comprising laminin beta-4 or a variant thereof can be produced or provided in the form of a cell which comprises and/or expresses a nucleic acid encoding the polypeptide. If a nucleic acid comprising a sequence encoding the polypeptide according to the invention or a variant thereof is used, such a nucleic acid can be an unmodified nucleic acid. In a preferred embodiment, the nucleic acid is a nucleic acid which does not occur as such in nature and comprises, compared with a natural nucleic acid, at least one modification, for example contains an isotope or a chemical modification, for example a methylation, a sequence modification, a label or the like, which indicates the synthetic origin. In a preferred embodiment, the nucleic acid is a recombinant nucleic acid or, in a more preferred embodiment, part of a vector in which it is functionally connected to a promoter allowing the expression, preferably overexpression, of the nucleic acid. A person skilled in the art is familiar with a multiplicity of suitable vectors which are commercially available, for example from Origene. For example, a vector encoding fusion constructs having a C-terminal GFP can be used. The vector can comprise a bacterial origin of replication and a promoter for expression in eukaryotic, preferably mammalian, cells, for example an SV40 promoter or chicken beta-actin promoter. The cell can be a eukaryotic or prokaryotic cell, preferably a eukaryotic cell, such as, for example, a yeast cell, and is more preferably a mammalian cell, even more preferably a human cell such as a HEK293 cell. Examples of a mammalian cell encompass HEK293, CHO or COS-7 cells. The cell comprising the nucleic acid encoding the polypeptide according to the invention can be a recombinant cell or an isolated cell, the term "isolated" meaning that the cell is enriched such that the environment thereof contains, in comparison with the wild-type of the cell or the environment thereof, fewer cells of different differentiation or species or in fact no other such cells. The cell or the vector can be used for the expression of the polypeptide, followed by the use thereof for the production of a composition or of a kit for the diagnosis of an autoimmune disease. The cell can be a live cell or a fixed cell which is no longer metabolically active. Fixation of cells is possible by means of treatment with acetone or formalin, as described in Probst et al. (Probst, C. Saschenbrecker, S., Stoecker, W., and Komorowski, L. (2014) Anti-neuronal autoantibodies: Current diagnostic challenges. Multiple Sclerosis and Related Disorders 3, 303-320).

The teaching according to the invention can be used not only for a diagnosis, but also for the prevention or for the treatment of a disease, more precisely for a method for preventing or treating a disease, comprising the steps of a) reducing the concentration of autoantibodies which bind against the polypeptide according to the invention in the blood of a subject and/or b) administering one or more than one immunosuppressive pharmaceutical substance, preferably from the group comprising rituximab, prednisone, methylprednisolone, cyclophosphamide, mycophenolate mofetil, intravenous immunoglobulins, FK506, cyclosporin, methotrexate, clobetasol propionate, dapsone, tetracycline, nicotinamide, colchicine and azathioprine.

In a preferred embodiment, the present invention provides for use of a means or reagent for the detection of an antibody against laminin beta-4 or of a nucleic acid comprising a sequence encoding laminin beta-4 or a variant thereof or of a vector comprising said sequence or of a cell comprising the vector or said nucleic acid for the production of a kit for the diagnosis of an autoimmune disease.

In a preferred embodiment, any method or any use according to the present invention can be intended for a nondiagnostic purpose, especially determination of the presence of an autoantibody against laminin beta-4 for some use other than diagnosing a patient. For example, the method or the use can be intended for the determination by in vitro testing of the efficiency of a medical device which is configured to remove an autoantibody from the blood of a patient, the testing being carried out with a liquid which is not patient blood. In a preferred embodiment, it is possible to use any method and any use according to the present invention with the intention of generating an autoantibody profile, preferably for the detection of a disease in a mammal, preferably a human. In a preferred embodiment, it is possible to use a method or use for the detection of disease-associated markers in a sample from patients suffering from a skin disease.

In a preferred embodiment, the method according to the present invention is a method for calibrating a diagnostic assay system or for confirming the reliability and/or sufficient capacity of such an assay system or of a therapeutic system for the removal of autoantibodies from the blood of a patient. In the case of a diagnostic assay system, autoantibodies are not detected in the sample from a patient who is to be diagnosed, but in an artificial solution having a known composition, especially having a defined, known concentration of the antibody or of a recombinant antibody of known concentration that binds against the autoantibody. The diagnostic system can be any system which allows the detection of autoantibodies in a sample, for example a medical diagnostic device according to the present invention.

In the case of a therapeutic system, for example an apparatus for apheresis, the method can be used for developing such a system and for testing its reliability and/or efficiency and/or capacity. For example, it is possible after an apheresis run or therebefore for a solution comprising a known concentration of an antibody which binds against the polypeptide according to the invention to be contacted with the system, and the method according to the present invention can be used for confirming that the system is capable of removing the antibody from the solution.

In a preferred embodiment, the invention provides an apparatus for the analysis of a sample from a patient in order to detect one or more than one autoantibody against laminin beta-4, the autoantibody or autoantibodies indicating an increased probability of the patient suffering from an autoimmune disease, the apparatus comprising the following:
  a. a carrier which comprises a means for the capture of at least one autoantibody in the sample when the sample is contacted with the carrier,
  b. a detectable means which is capable of binding to the captured antibody when the detectable means is contacted with the carrier, the detectable means preferably being a labeled secondary antibody which is capable of binding to the antibody captured on the carrier,
  c. optionally a means for the removal of a sample from the carrier and for the removal of the detectable means, preferably by washing;
  d. a detector for the detection of the presence of the detectable means and for the conversion of the results into an electrical signal, and
  e. optionally a means for the receiving of the electrical signal from the detector and determination of whether the intensity of the signal indicates an increased probability of an autoimmune disease, by comparison of the intensity of the signal with the intensity of a background signal or with an inputted reference value obtained using samples from healthy persons.

The present application comprises a series of sequences of novel nucleic acids or polypeptides:

```
SEQ ID NO 1: Primer sense LAMB4:
ATAGGTCTCACATGCAATTTCAACTGACCCTTTTTTGCACCTTG SEQ ID NO 2: Primer anti-sense LAMB4:
ATAGGTCTCGTCGAGGCTATAGCACCTAGCATATTTTTTTCTTG SEQ ID NO 3: Primer anti-sense LAMB4-Stop:
ATAGGTCTCCTCGAGCTAGCTATAGCACCTAGCATATTTTTTTCTTG SEQ ID NO 4_pTriEx-1 (standard vector)
GGGGAATTGTGAGCGGATAACAATTCCCCGGAGTTAATCCGGGACCTTTAATTCA
```

-continued

```
ACCCAACACAATATATTATAGTTAAATAAGAATTATTATCAAATCATTTGTATATT
AATTAAAATACTATACTGTAAATTACATTTTATTTACAATCAAAGGAGATATACC
ATGGCGATATCCCGGGAGCTCGTGGATCCGAATTCTCAGATCTCGGCGCGCCTGC
AGGTCGACGGTACCGGTTCGAAGCTTGCGGCCGCACAGCTGTATACACGTGCAAG
CCAGCCAGAACTCGCCCCGGAAGACCCCGAGGATCTCGAGCACCACCATCACCAT
CACCATCACTAAGTGATTAACCTCAGGTGCAGGCTGCCTATCAGAAGGTGGTGGC
TGGTGTGGCCAATGCCCTGGCTCACAAATACCACTGAGATCGATCTTTTTCCCTCT
GCCAAAAATTATGGGGACATCATGAAGCCCCTTGAGCATCTGACTTCTGGCTAAT
AAAGGAAATTTATTTTCATTGCAATAGTGTGTTGGAATTTTTTGTGTCTCTCACTC
GGAAGGACATATGGGAGGGCAAATCATTTAAAACATCAGAATGAGTATTTGGTTT
AGAGTTTGGCAACATATGCCCATATGTAACTAGCATAACCCCTTGGGGCCTCTAA
ACGGGTCTTGAGGGGTTTTTTGCTGAAAGCATGCGGAGGAAATTCTCCTTGAAGT
TTCCCTGGTGTTCAAAGTAAAGGAGTTTGCACCAGACGCACCTCTGTTCACTGGTC
CGGCGTATTAAAACACGATACATTGTTATTAGTACATTTATTAAGCGCTAGATTCT
GTGCGTTGTTGATTTACAGACAATTGTTGTACGTATTTTAATAATTCATTAAATTT
ATAATCTTTAGGGTGGTATGTTAGAGCGAAAATCAAATGATTTTCAGCGTCTTTAT
ATCTGAATTTAAATATTAAATCCTAATAGATTTGTAAAATAGGTTTCGATTAGTT
TCAAACAAGGGTTGTTTTTCCGAACCGATGGCTGGACTATCTAATGGATTTTCGCT
CAACGCCACAAAACTTGCCAAATCTTGTAGCAGCAATCTAGCTTTGTCGATATTC
GTTTGTGTTTTGTTTTGTAATAAAGGTTCGACGTCGITCAAAATATTATGCGCTTT
TGTATTTCTTTCATCACTGTCGTTAGTGTACAATTGACTCGACGTAAACACGTTAA
ATAGAGCTTGGACATATTTAACATCGGGCGTGTTAGCTTTATTAGGCCGATTATC
GTCGTCGTCCCAACCCTCGTCGTTAGAAGTTGCTTCCGAAGACGATTTTGCCATA
GCCACACGACGCCTATTAATTGTGTCGGCTAACACGTCCGCGATCAAATTTGTAG
TTGAGCTTTTTGGAATTATTTCTGATTGCGGGCGTTTTTGGGCGGGTTTCAATCTA
ACTGTGCCCGATTTTAATTCAGACAACACGTTAGAAAGCGATGGTGCAGGCGGTG
GTAACATTTCAGACGGCAAATCTACTAATGGCGGCGGTGGTGGAGCTGATGATA
AATCTACCATCGGTGGAGGCGCAGGCGGGGCTGGCGGCGGAGGCGGAGGCGGA
GGTGGTGGCGGTGATGCAGACGGCGGTTTAGGCTCAAATGTCTCTTTAGGCAACA
CAGTCGGCACCTCAACTATTGTACTGGTTTCGGGCGCCGTTTTTGGTTTGACCGGT
CTGAGACGAGTGCGATTTTTTCGTTTCTAATAGCTTCCAACAATTGTTGTCTGTC
GTCTAAAGGTGCAGCGGGTTGAGGTTCCGTCGGCATTGGTGGAGCGGGCGGCAA
TTCAGACATCGATGGTGGTGGTGGTGGAGGCGCTGGAATGTTAGGCACGGG
AGAAGGTGGTGGCGGCGGTGCCGCCGGTATAATTTGTTCTGGTTTAGTTTGTTCG
CGCACGATTGTGGGCACCGGCGCAGGCGCCGCTGGCTGCACAACGGAAGGTCGT
CTGCTTCGAGGCAGCGCTTGGGGTGGTGGCAATTCAATATTATAATTGGAATACA
AATCGTAAAAATCTGCTATAAGCATTGTAATTTCGCTATCGTTTACCGTGCCGATA
TTTAACAACCGCTCAATGTAAGCAATTGTATTGTAAAGAGATTGTCTCAAGCTCG
GAACGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGC
```

-continued

```
AAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTC

CCTCGTGCGCTCTCCTGTTCCGACCCTGCCGCTTACCGGATACCTGTCCGCCTTTC

TCCCTTCGGGAAGCGTGGCGCTTTCTCAATGCTCACGCTGTAGGTATCTCAGTTCG

GTGTAGGTCGTTCGCTCCAAGCTGGGCTGTGTGCACGAACCCCCCGTTCAGCCCG

ACCGCTGCGCCTTATCCGGTAACTATCGTCTTGAGTCCAACCCGGTAAGACACGA

CTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAG

GACAGTATTTGGTATCTGCGCTCTGCTGAAGCCAGTTACCTTCGGAAAAAGAGTT

GGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGTTAC

CAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCT

GGCCCCAGTGCTGCAATGATACCGCGAGACCCACGCTCACCGGCTCCAGATTTAT

CAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCA

CGCTCGTCGTTTGGTATGGCTTCATTCAGCTCCGGTTCCCAACGATCAAGGCGAG

TTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGC

ATAATTCTCTTACTGTCATGCCATCCGTAAGATGCTTTTCTGTGACTGGTGAGTAC

TCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCAT

TGGAAAACGTTCTTCGGGGCGAAAACTCTCAAGGATCTTACCGCTGTTGAGATCC

AGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAA

TAAGGGCGACACGGAAATGTTGAATACTCATACTCTTCCTTTTTCAATATTATTGA

AGCATTTATCAGGGTTATTGTCTCATGTCCGCGCGTTTCCTGCATCTTTTAATCAA

ATCCCAAGATGTGTATAAACCACCAAACTGCCAAAAAATGAAAACTGTCGACAA

GCTCTGTCCGTTTGCTGGCAACTGCAAGGGTCTCAATCCTATTTGTAATTATTGAA

TAATAAAACAATTATAAATGTCAAATTTGTTTTTTATTAACGATACAAACCAAAC

GCAACAAGAACATTTGTAGTATTATCTATAATTGAAAACGCGTAGTTATAATCGC

TGAGGTAATATTTAAAATCATTTTCAAATGATTCACAGTTAATTTGCGACAATAT

AATTTTATTTTCACATAAACTAGACGCCTTGTCGTCTTCTTCTTCGTATTCCTTCTC

TTTTTCATTTTTCTCTTCATAAAAATTAACATAGTTATTATCGTATCCATATATGTA

TCTATCGTATAGAGTAAATTTTTTGTTGTCATAAATATATATGTCTTTTTTAATGG

GGTGTATAGTACCGCTGCGCATAGTTTTTCTGTAATTTACAACAGTGCTATTTTCT

GGTAGTTCTTCGGAGTGTGTTGCTTTAATTATTAAATTTATATAATCAATGAATTT

GGGATCGTCGGTTTTGTACAATATGTTGCCGGCATAGTACGCAGCTTCTTCTAGTT

CAATTACACCATTTTTTAGCAGCACCGGATTAACATAACTTTCCAAAATGTTGTAC
```

```
GAACCGTTAAACAAAAACAGTTCACCTCCCTTTTCTATACTATTGTCTGCGAGCA

GTTGTTTGTTGTTAAAAATAACAGCCATTGTAATGAGACGCACAAACTAATATCA

CAAACTGGAAATGTCTATCAATATATAGTTGCTCTAGTTATTAATAGTAATCAATT

ACGGGGTCATTAGTTCATAGCCCATATATGGAGTTCCGCGTTACATAACTTACGG

TAAATGGCCCGCCTGGCTGACCGCCCAACGACCCCCGCCCATTGACGTCAATAAT

GACGTATGTTCCCATAGTAACGCCAATAGGGACTTTCCATTGACGTCAATGGGTG

GACTATTTACGGTAAACTGCCCACTTGGCAGTACATCAAGTGTATCATATGCCAA

GTACGCCCCCTATTGACGTCAATGACGGTAAATGGCCCGCCTGGCATTATGCCCA

GTACATGACCTTATGGGACTTTCCTACTTGGCAGTACATCTACGTATTAGTCATCG

CTATTACCATGCATGGTCGAGGTGAGCCCCACGTTCTGCTTCACTCTCCCCATCTC

CCCCCCCTCCCCACCCCCAATTTTGTATTTATTTATTTTTAATTATTTTGTGCAGC

GATGGGGGCGGGGGGGGGGGGGGGCGCGCGCCAGGCGGGGCGGGGCGGGGCG

AGGGGCGGGGCGGGGCGAGGCGGAGAGGTGCGGCGGCAGCCAATCAGAGCGGC

GCGCTCCGAAAGTTTCCTTTTATGGCGAGGCGGCGGCGGCGGCGGCCCTATAAAA

AGCGAAGCGCGCGGCGGGCGGGAGTCGCTGCGACGCTGCCTTCGCCCCGTGCCC

CGCTCCGCCGCCGCCTCGCGCCGCCCGCCCCGGCTCTGACTGACCGCGTTACTCC

CACAGGTGAGCGGGCGGGACGGCCCTTCTCCTTCGGGCTGTAATTAGCGCTTGGT

TTAATGACGGCTTGTTTCTTTTCTGTGGCTGCGTGAAAGCCTTGAGGGGCTCCGGG

AGGGCCCTTTGTGCGGGGGGAGCGGCTCGGGGCTGTCCGCGGGGGGACGGCTGC

CTTCGGGGGGACGGGGCAGGGCGGGGTTCGGCTTCTGGCGTGTGACCGGCGGC

TCTAGAGCCTCTGCTAACCATGTTCATGCCTTCTTCTTTTTCCTACAGCTCCTGGGC

AACGTGCTGGTTATTGTGCTGTCTCATCATTTTGGCAAAGAATTGGATCGGACCG

AAATTAATACGACTCACTATA

SEQ ID NO 5_pTriEx-1-LAMB4(IF1)[human] - encodes - human laminin beta-4
without His-tag
GGAGTCGCTGCGACGCTGCCTTCGCCCCGTGCCCCGCTCCGCCGCCGCCTCGCGC

CGCCCGCCCCGGCTCTGACTGACCGCGTTACTCCCACAGGTGAGCGGGCGGGACG

GCCCTTCTCCTTCGGGCTGTAATTAGCGCTTGGTTTAATGACGGCTTGTTTCTTTTC

TGTGGCTGCGTGAAAGCCTTGAGGGGCTCCGGGAGGGCCCTTTGTGCGGGGGGAG

CGGCTCGGGGCTGTCCGCGGGGGGACGGCTGCCTTCGGGGGGACGGGGCAGGG

CGGGGTTCGGCTTCTGGCGTGTGACCGGCGGCTCTAGAGCCTCTGCTAACCATGTT

CATGCCTTCTTCTTTTTCCTACAGCTCCTGGGCAACGTGCTGGTTATTGTGCTGTCT

CATCATTTTGGCAAAGAATTGGATCGGACCGAAATTAATACGACTCACTATAGGG

GAATTGTGAGCGGATAACAATTCCCCGGAGTTAATCCGGACCTTTAATTCAACC

CAACACAATATATTATAGTTAAATAAGAATTATTATCAAATCATTTGTATATTAAT

TAAAATACTATACTGTAAATTACATTTTATTTACAATCAAAGGAGATATACCATGC

AATTTCAACTGACCCTTTTTTGCACCTTGGGTGGCTCAGTTACTCAAAAGCTCAA

GATGACTGCAACAGGGGTGCCTGTCATCCCACCACTGGTGATCTCCTGGTGGGCA

GGAACACGCAGCTTATGGCTTCTTCTACCTGTGGGCTGAGCAGAGCCCAGAAATA

CTGCATCCTCAGTTACCTGGAGGGGGAACAAAAATGCTTCATCTGTGACTCTAGA

TTTCCATATGATCCGTATGACCAACCCAACAGCCACACCATTGAGAATGTCATTGT
```

-continued

```
AAGTTTTGAACCAGACAGAGAAAAGAAATGGTGGCAATCTGAAAATGGTCTTGA
TCATGTCAGCATCAGACTGGACTTAGAGGCATTATTTCGGTTCAGCCACCTTATCC
TGACCTTTAAGACTTTTCGGCCTGCTGCAATGTTAGTTGAACGTTCCACAGACTAT
GGACACAACTGGAAAGTGTTCAAATATTTTGCAAAAGACTGTGCCACTTCCTTTC
CTAACATCACATCTGGCCAGGCCCAGGGAGTGGGAGACATTGTTTGTGACTCCAA
ATACTCGGATATTGAACCCTCAACAGGTGGAGAGGTTGTTTTAAAAGTTTTGGAT
CCCAGTTTTGAAATTGAAAACCCTTATAGCCCCTACATCCAAGACCTTGTGACATT
GACAAACCTGAGGATAAACTTTACCAAGCTCCACACCCTTGGGGATGCTTTGCTT
GGAAGGAGGCAAAATGATTCCCTTGATAAATACTACTATGCTCTGTACGAGATGA
TTGTTCGGGGAAGCTGCTTTTGCAATGGCCATGCTAGCGAATGTCGCCCTATGCA
GAAGATGCGGGGAGATGTTTTCAGCCCTCCTGGAATGGTTCACGGTCAGTGTGTG
TGTCAGCACAATACAGATGGTCCGAACTGTGAGAGATGCAAGGACTTCTTCCAGG
ATGCTCCTTGGAGGCCAGCTGCAGACCTCCAGGACAACGCTTGCAGATCGTGCAG
CTGTAACAGCCACTCCAGCCGCTGTCACTTTGACATGACTACGTACCTGGCAAGC
GGTGGCCTCAGCGGGGCGTGTGTGAAGACTGCCAGCACAACACTGAGGGGCAG
CACTGCGACCGCTGCAGACCCCTCTTCTACAGGGACCCGCTCAAGACCATCTCAG
ATCCCTACGCGTGCATTCCTTGTGAATGTGACCCCGATGGGACCATATCTGGTGGC
ATTTGTGTGAGCCACTCTGATCCTGCCTTAGGGTCTGTGGCTGGCCAGTGCCTTTG
TAAAGAGAACGTGGAAGGAGCCAAATGCGACCAGTGCAAACCCAACCACTATGG
ACTAAGCGCCACCGACCCCCTGGGCTGCCAGCCCTGCGACTGTAACCCCCTTGGG
AGTTTGCCATTCTTGACCTGTGATGTGGATACAGGCCAATGCTTGTGCCTGTCATA
TGTCACCGGAGCACACTGCGAAGAATGCACTGTTGGATACTGGGGCCTGGGAAAT
CATCTCCATGGGTGTTCTCCCTGTGACTGTGATATTGGAGGTGCTTATTCTAACGT
GTGCTCACCCAAGAATGGGCAGTGTGAATGCCGCCCACATGTCACTGGCCGTAGC
TGCTCTGAACCAGCCCCTGGCTACTTCTTTGCTCCTTTGAATTTCTATCTCTACGAG
GCAGAGGAAGCCACAACACTCCAAGGACTGGCGCCTTTGGGCTCGGAGACGTTTG
GCCAGAGTCCTGCTGTTCACGTTGTTTTAGGAGAGCCAGTTCCTGGGAACCCTGTT
ACATGGACTGGACCTGGATTTGCCAGGGTTCTCCCTGGGGCTGGCTTGAGATTTG
CTGTCAACAACATTCCCTTTCCTGTGGACTTCACCATTGCCATTCACTATGAAACC
CAGTCTGCAGCTGACTGGACTGTCCAGATTGTGGTGAACCCCCCTGGAGGGAGTG
AGCACTGCATACCCAAGACTCTACAGTCAAAGCCTCAGTCTTTTGCCTTACCAGC
GGCTACGAGAATCATGCTGCTTCCCACACCCATCTGTTTAGAACCAGATGTACAA
TATTCCATAGATGTCTATTTTTCTCAGCCTTTGCAAGGAGAGTCCCACGCTCATTC
ACATGTCCTGGTGGACTCTCTTGGCCTTATTCCCCAAATCAATTCATTGGAGAATT
TCTGCAGCAAGCAGGACTTAGATGAGTATCAGCTTCACAACTGTGTTGAAATTGC
CTCAGCAATGGGACCTCAAGTGCTCCCGGGTGCCTGTGAAAGGCTGATCATCAGC
ATGTCTGCCAAGCTGCATGATGGGGCTGTGGCCTGCAAGTGTCACCCCCAGGGCT
CAGTCGGATCCAGCTGCAGCCGACTTGGAGGCCAGTGCCAGTGTAAACCTCTTGT
GGTCGGGCGCTGCTGTGACAGGTGCTCAACTGGAAGCTATGATTTGGGGCATCAC
GGCTGTCACCCATGTCACTGCCATCCTCAAGGATCAAAGGACACTGTATGTGACC
AAGTAACAGGACAGTGCCCCTGCCATGGAGAGGTGTCTGGCCGCCGCTGTGATCG
```

-continued

```
CTGCCTGGCAGGCTACTTTGGATTTCCCAGCTGCCACCCTTGCCCTTGTAATAGGT
TTGCTGAACTTTGTGATCCTGAGACAGGGTCATGCTTCAATTGTGGAGGCTTTAC
AACTGGCAGAAACTGTGAAAGGTGTATTGATGGTTACTATGGAAATCCTTCTTCA
GGACAGCCCTGTCGTCCTTGCCTGTGTCCAGATGATCCCTCAAGCAATCAGTATTT
TGCCCATTCCTGTTATCAGAATCTGTGGAGCTCAGATGTAATCTGCAATTGTCTTC
AAGGTTATACGGGTACTCAGTGTGGAGAATGCTCTACTGGTTTCTATGGAAATCC
AAGAATTTCAGGAGCACCTTGCCAACCATGTGCCTGCAACAACAACATAGATGTA
ACCGATCCAGAGTCCTGCAGCCGGGTAACAGGGGAGTGCCTTCGATGTTTGCACA
ACACTCAGGGCGCAAACTGCCAGCTCTGCAAACCAGGTCACTATGGATCAGCCCT
CAATCAGACCTGCAGAAGATGCTCCTGCCATGCTTCCGGCGTGAGTCCCATGGAG
TGTCCCCCTGGTGGGGAGCTTGCCTCTGTGACCCTGTCACTGGTGCATGTCCTTG
TCTGCCGAATGTCACAGGCCTGGCCTGTGACCGTTGTGCTGATGGATACTGGAAT
CTGGTCCCTGGCAGAGGATGTCAGTCATGTGACTGTGACCCTAGGACCTCTCAAA
GTAGCCACTGTGACCAGCTTACAGGCCAGTGTCCGTGTAAATTAGGTTACGGCGG
GAAACGTTGCAGTGAGTGCCAGGAAAATTATTATGGTGATCCACCTGGGCGATGC
ATTCCATGTGATTGTAACAGGGCAGGTACCCAGAAGCCCATCTGTGATCCAGACA
CAGGCATGTGCCGCTGCCGGGAGGGTGTCAGCGGCCAGAGATGTGATCGCTGTG
CCCGGGGACACAGCCAGGAATTCCCTACTTGTCTTCAATGTCACTTGTGCTTTGAT
CAGTGGGACCACACCATTTCTTCCCTCTCCAAAGCGGTGCAAGGGTTAATGAGAC
TGGCTGCTAACATGGAAGATAAAAGAGAGACCCTGCCTGTCTGTGAGGCAGACT
TCAAAGACCTCAGAGGGAACGTGTCTGAAATAGAAAGGATTTTGAAACATCCTG
TTTTCCCATCTGGGAAATTCTTAAAAGTCAAGGATTATCATGACTCTGTTAGAAG
ACAAATCATGCAGCTAAATGAACAACTGAAAGCAGTGTATGAATTTCAAGATCT
GAAAGATACAATAGAAAGAGCAAAGAATGAAGCAGACCTCTTACTTGAAGACCT
TCAGGAAGAAATTGATTTGCAATCCAGTGTCCTTAATGCAAGCATTGCGGACTCC
TCAGAAAACATCAAGAAATATTATCACATATCATCATCTGCTGAAAAGAAAATTA
ATGAAACTAGTTCCACCATTAATACCTCTGCAAATACAAGGAATGACTTACTTAC
CATCTTAGATACACTAACCTCAAAAGGAAACTTGTCATTGGAAAGATTAAAGCAG
ATTAAGATACCAGATATCCAAATATTGAATGAAAAGGTGTGCGGAGATCCAGGA
AATGTGCCATGTGTGCCCTTGCCCTGTGGCGGTGCTCTCTGCACGGGCCGGAAGG
GGCACAGGAAGTGTAGGGGTCCCGGCTGTCACGGCTCCCTGACCCTCTCAACGAA
TGCCCTCCAAAAAGCCCAGGAAGCAAAATCCATTATTCGTAATTTGGACAAACAG
GTTCGTGGGTTGAAAAATCAGATCGAAAGTATAAGTGAACAGGCAGAAGTCTCC
AAAAACAATGCCTTACAGCTGAGGGAAAAACTGGGAAATATAAGAAACCAAAGT
GACTCTGAAGAAGAAAACATCAATCTTTTCATCAAAAAAGTGAAAAACTTTTTGT
TAGAGGAAAACGTGCCTCCAGAAGACATCGAGAAGGTTGCGAATGGTGTGCTTG
ACATTCACCTACCAATTCCATCCCAAAATCTAACCGATGAACTTGTCAAAATACA
GAAACATATGCAACTCTGTGAGGATTACAGGACAGATGAAAACAGGTTAAATGA
AGAAGCAGATGGAGCCCAAAAGCTTTTGGTGAAGGCCAAAGCAGCTGAGAAAGC
AGCAAATATTCTATTAAATCTTGACAAAACATTGAACCAGTTACAACAAGCTCAA
```

-continued

```
ATCACTCAAGGACGGGCAAACTCTACCATTACACAGCTGACTGCCAATATAACAA

AAATAAAAAAGAATGTGCTGCAGGCTGAAAATCAAACCAGGGAAATGAAGAGT

GAGCTGGAGTTAGCAAAGCAGCGATCAGGGCTGGAGGATGGACTTTCCCTGCTG

CAGACCAAGTTGCAAAGGCATCAAGACCACGCTGTCAATGCGAAAGTTCAGGCT

GAATCTGCCCAACACCAGGCTGGGAGTCTTGAGAAGGAATTTGTTGAGCTGAAA

AAACAATATGCTATTCTCCAACGTAAGACAAGCACTACAGGACTAACAAAGGAG

ACATTAGGAAAAGTTAAACAGCTAAAAGATGCGGCAGAAAAATTGGCTGGAGAT

ACAGAGGCCAAGATAAGAAGAATAACAGATTTAGAAAGGAAAATCCAAGATTTG

AATCTAAGTAGACAAGCAAAAGCTGATCAACTGAGAATATTGGAAGATCAAGTT

GTTGCCATTAAAAATGAAATTGTTGAACAAGAAAAAAATATGCTAGGTGCTAT

AGCCTCGAGCACCACCATCACCATCACCATCACTAAGTGATTAACCTCAGGTGCA

GGCTGCCTATCAGAAGGTGGTGGCTGGTGTGGCCAATGCCCTGGCTCACAAATAC

CACTGAGATCGATCTTTTTCCCTCTGCCAAAAATTATGGGGACATCATGAAGCCC

CTTGAGCATCTGACTTCTGGCTAATAAAGGAAATTTATTTTCATTGCAATAGTGTG

TTGGAATTTTTTGTGTCTCTCACTCGGAAGGACATATGGGAGGGCAAATCATTTA

AAACATCAGAATGAGTATTTGGTTTAGAGTTTGGCAACATATGCCCATATGTAAC

TAGCATAACCCCTTGGGGCCTCTAAACGGGTCTTGAGGGGTTTTTTGCTGAAAGC

ATGCGGAGGAAATTCTCCTTGAAGTTTCCCTGGTGTTCAAAGTAAAGGAGTTTGC

ACCAGACGCACCTCTGTTCACTGGTCCGGCGTATTAAAACACGATACATTGTTAT

TAGTACATTTATTAAGCGCTAGATTCTGTGCGTTGTTGATTTACAGACAATTGTTG

TACGTATTTTAATAATTCATTAAATTTATAATCTTTAGGGTGGTATGTTAGAGCGA

AAATCAAATGATTTTCAGCGTCTTTATATCTGAATTTAAATATTAAATCCTCAATA

GATTTGTAAAATAGGTTTCGATTAGTTTCAAACAAGGGTTGTTTTTCCGAACCGAT

GGCTGGACTATCTAATGGATTTTCGCTCAACGCCACAAAACTTGCCAAATCTTGT

AGCAGCAATCTAGCTTTGTCGATATTCGTTTGTGTTTTGTTTTGTAATAAAGGTTC

GACGTCGTTCAAAATATTATGCGCTTTTGTATTTCTTTCATCACTGTCGTTAGTGT

ACAATTGACTCGACGTAAACACGTTAAATAGAGCTTGGACATATTTAACATCGGG

CGTGTTAGCTTTATTAGGCCGATTATCGTCGTCGTCCCAACCCTCGTCGTTAGAAG

TTGCTTCCGAAGACGATTTTGCCATAGCCACACGACGCCTATTAATTGTGTCGGCT

AACACGTCCGCGATCAAATTTGTAGTTGAGCTTTTTGGAATTATTTCTGATTGCGG

GCGTTTTTGGGCGGGTTTCAATCTAACTGTGCCCGATTTTAATTCAGACAACACGT

TAGAAAGCGATGGTGCAGGCGGTGGTAACATTTCAGACGGCAAATCTACTAATG

GCGGCGGTGGTGGAGCTGATGATAAATCTACCATCGGTGGAGGCGCAGGCGGGG

CTGGCGGCGGAGGCGGAGGCGGAGGTGGTGGCGGTGATGCAGACGGCGGTTTAG

GCTCAAATGTCTCTTTAGGCAACACAGTCGGCACCTCAACTATTGTACTGGTTTCG

GGCGCCGTTTTTGGTTTGACCGGTCTGAGACGAGTGCGATTTTTTTCGTTTCTAAT

AGCTTCCAACAATTGTTGTCTGTCGTCTAAAGGTGCAGCGGGTTGAGGTTCCGTC

GGCATTGGTGGAGCGGGCGGCAATTCAGACATCGATGGTGGTGGTGGTGGTGGA

GGCGCTGGAATGTTAGGCACGGGAGAAGGTGGTGGCGGCGGTGCCGCCGGTATA

ATTTGTTCTGGTTTAGTTTGTTCGCGCACGATTGTGGGCACCGGCGCAGGCGCCG

CTGGCTGCACAACGGAAGGTCGTCTGCTTCGAGGCAGCGCTTGGGGTGGTGGCA
```

```
ATTCAATATTATAATTGGAATACAAATCGTAAAAATCTGCTATAAGCATTGTAAT

TTCGCTATCGTTTACCGTGCCGATATTTAACAACCGCTCAATGTAAGCAATTGTAT

TGTAAAGAGATTGTCTCAAGCTCGGAACGCTGCGCTCGGTCGTTCGGCTGCGGCG

AGCGGTATCAGCTCACTCAAAGGCGGTAATACGGTTATCCACAGAATCAGGGGA

TAACGCAGGAAAGAACATGTGAGCAAAAGGCCAGCAAAAGGCCAGGAACCGTA.

AAAAGGCCGCGTTGCTGGCGTTTTTCCATAGGCTCCGCCCCCCTGACGAGCATCA

CAAAAATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCAATGC

TCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTT

GAGTCCAACCCGGTAAGACACGACTTATCGCCACTGGCAGCAGCCACTGGTAAC

AGGATTAGCAGAGCGAGGTATGTAGGCGGTGCTACAGAGTTCTTGAAGTGGTGG

CCTAACTACGGCTACACTAGAAGGACAGTATTTGGTATCTGCGCTCTGCTGAAGC

CAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGA

TCTCAAGAAGATCCTTTGTTACCAATGCTTAATCAGTGAGGCACCTATCTCAGCG

ATCTGTCTATTTCGTTCATCCATAGTTGCCTGACTCCCCGTCGTGTAGATAACTAC

GATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGA

GCGCAGAAGTGGTCCTGCAACTTTATCCGCCTCCATCCAGTCTATTAATTGTTGCC

GGGAAGCTAGAGTAAGTAGTTCGCCAGTTAATAGTTTGCGCAACGTTGTTGCCAT

TGCTACAGGCATCGTGGTGTCACGCTCGTCGTTTGGTATGGCTTCATTCAGCTCCG

GTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCAC

TCATGGTTATGGCAGCACTGCATAATTCTCTTACTGTCATGCCATCCGTAAGATGC

TTTTCTGTGACTGGTGAGTACTCAACCAAGTCATTCTGAGAATAGTGTATGCGGC

GACCGAGTTGCTCTTGCCCGGCGTCAATACGGGATAATACCGCGCCACATAGCAG

AACTTTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAACTGATC

TTCAGCATCTTTTACTTTCACCAGCGTTTCTGGGTGAGCAAAAACAGGAAGGCAA

AATGCCGCAAAAAAGGGAATAAGGGCGACACGGAAATGTTGAATACTCATACTC

TTCCTTTTTCAATATTATTGAAGCATTTATCAGGGTTATTGTCTCATGTCCGCGCGT

TTCCTGCATCTTTTAATCAAATCCCAAGATGTGTATAAACCACCAAACTGCCAAA

AAATGAAAACTGTCGACAAGCTCTGTCCGTTTGCTGGCAACTGCAAGGGTCTCAA

TCCTATTTGTAATTATTGAATAATAAAACAATTATAAATGTCAAATTTGTTTTTTA

TTAACGATACAAACCAAACGCAACAAGAACATTTGTAGTATTATCTATAATTGAA

AACGCGTAGTTATAATCGCTGAGGTAATATTTAAAATCATTTTCAAATGATTCAC

AGTTAATTTGCGACAATATAATTTTATTTTCACATAAACTAGACGCCTTGTCGTCT

TCTTCTTCGTATTCCTTCTCTTTTTCATTTTTCTCTTCATAAAAATTAACATAGTTAT
```

-continued

```
TATCGTATCCATATATGTATCTATCGTATAGAGTAAATTTTTGTTGTCATAAATA

TATATGTCTTTTTTAATGGGGTGTATAGTACCGCTGCGCATAGTTTTTCTGTAATT

TACAACAGTGCTATTTTCTGGTAGTTCTTCGGAGTGTGTTGCTTTAATTATTAAAT

TTATATAATCAATGAATTTGGGATCGTCGGTTTTGTACAATATGTTGCCGGCATAG

TACGCAGCTTCTTCTAGTTCAATTACACCATTTTTTAGCAGCACCGGATTAACATA

ACTTTCCAAAATGTTGTACGAACCGTTAAACAAAAACAGTTCACCTCCCTTTTCTA

TACTATTGTCTGCGAGCAGTTGTTTGTTGTTAAAAATAACAGCCATTGTAATGAG

ACGCACAAACTAATATCACAAACTGGAAATGTCTATCAATATATAGTTGCTCTAG

TTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCG

CCCATTGACGTCAATAATGACGTATGTTCCCATAGTAACGCCAATAGGGACTTTC

CATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTAC

ATCTACGTATTAGTCATCGCTATTACCATGCATGGTCGAGGTGAGCCCCACGTTCT

GCTTCACTCTCCCCATCTCCCCCCCCTCCCCACCCCCAATTTTGTATTTATTTATTT

TTTAATTATTTTGTGCAGCGATGGGGCGGGGGGGGGGGGGGCGCGCGCCAG

GCGGGGCGGGGCGGGGCGAGGGCGGGGCGGGGCGAGGCGGAGAGGTGCGGCG

GCAGCCTTCAGAGCGGCGCGCTCCGAAAGTTTCCTTTTATGGCGAGGCGGCGGC

GGCGGCGGCCCTATAAAAAGCGAAGCGCGCGGCGGGCG

SEQ ID NO 6_pTriEx-1-LAMB4(IF1)[human](dHis) - encodes - human laminin beta-4
with His-tag
GGAGTCGCTGCGACGCTGCCTTCGCCCCGTGCCCCGCTCCGCCGCCGCCTCGCGC

CGCCCGCCCCGGCTCTGACTGACCGCGTTACTCCCACAGGTGAGCGGGCGGGACG

GCCCTTCTCCTTCGGGCTGTAATTAGCGCTTGGTTTAATGACGGCTTGTTTCTTTTC

TGTGGCTGCGTGAAAGCCTTGAGGGGCTCCGGGAGGGCCCTTTGTGCGGGGGGAG

CGGCTCGGGGCTGTCCGCGGGGGGACGGCTGCCTTCGGGGGGGACGGGGCAGGG

CGGGGTTCGGCTTCTGGCGTGTGACCGGCGGCTCTAGAGCCTCTGCTAACCATGTT

CATGCCTTCTTCTTTTTCCTACAGCTCCTGGGCAACGTGCTGGTTATTGTGCTGTCT

CATCATTTTGGCAAAGAATTGGATCGGACCGAAATTAATACGACTCACTATAGGG

GAATTGTGAGCGGATAACAATTCCCCGGAGTTAATCCGGGACCTTTAATTCAACC

CAACACAATATATTATAGTTAAATAAGAATTATTATCAAATCATTTGTATATTAAT

TAAAATACTATACTGTAAATTACATTTTATTTACAATCAAAGGAGATATACCATGC

AATTTCAACTGACCCTTTTTTTGCACCTTGGGTGGCTCAGTTACTCAAAAGCTCAA

GATGACTGCAACAGGGGTGCCTGTCATCCCACCACTGGTGATCTCCTGGTGGGCA

GGAACACGCAGCTTATGGCTTCTTCTACCTGTGGGCTGAGCAGAGCCCAGAAATA

CTGCATCCTCAGTTACCTGGAGGGGAACAAAAATGCTTCATCTGTGACTCTAGA

TTTCCATATGATCCGTATGACCAACCCAACAGCCACACCATTGAGAATGTCATTGT

AAGTTTTGAACCAGACAGAGAAAAGAAATGGTGGCAATCTGAAAATGGTCTTGA

TCATGTCAGCATCAGACTGGACTTAGAGGCATTATTTCGGTTCAGCCACCTTATCC

TGACCTTTAAGACTTTTGGCCTGCTGCAATGTTAGTTGAACGTTCCACAGACTAT

GGACACAACTGGAAAGTGTTCAAATATTTTGCAAAAGACTGTGCCACTTCCTTTC
```

```
CTAACATCACATCTGGCCAGGCCCAGGGAGTGGGAGACATTGTTTGTGACTCCAA
ATACTCGGATATTGAACCCTCAACAGGTGGAGAGGTTGTTTTAAAAGTTTTGGAT
CCCAGTTTTGAAATTGAAAACCCTTATAGCCCCTACATCCAAGACCTTGTGACATT
GACAAACCTGAGGATAAACTTTACCAAGCTCCACACCCTTGGGGATGCTTTGCTT
GGAAGGAGGCAAAATGATTCCCTTGATAAATACTACTATGCTCTGTACGAGATGA
TTGTTCGGGAAGCTGCTTTTGCAATGGCCATGCTAGCGAATGTCGCCCTATGCA
GAAGATGCGGGAGATGTTTTCAGCCCTCCTGGAATGGTTCACGTCAGTGTGTG
TGTCAGCACAATACAGATGGTCCGAACTGTGAGAGATGCAAGGACTTCTTCCAGG
ATGCTCCTTGGAGGCCAGCTGCAGACCTCCAGGACAACGCTTGCAGATCGTGCAG
CTGTAACAGCCACTCCAGCCGCTGTCACTTTGACATGACTACGTACCTGGCAAGC
GGTGGCCTCAGCGGGGCGTGTGTGAAGACTGCCAGCACAACACTGAGGGGCAG
CACTGCGACCGCTGCAGACCCCTCTTCTACAGGGACCCGCTCAAGACCATCTCAG
ATCCCTACGCGTGCATTCCTTGTGAATGTGACCCCGATGGGACCATATCTGGTGGC
ATTTGTGTGAGCCACTCTGATCCTGCCTTAGGGTCTGTGGCTGGCCAGTGCCTTTG
TAAAGAGAACGTGGAAGGAGCCAAATGCGACCAGTGCAAACCCAACCACTATGG
ACTAAGCGCCACCGACCCCCTGGGCTGCCAGCCCTGCGACTGTAACCCCCTTGGG
AGTCTGCCATTCTTGACCTGTGATGTGGATACAGGCCAATGCTTGTGCCTGTCATA
TGTCACCGGAGCACACTGCGAAGAATGCACTGTTGGATACTGGGGCCTGGGAAAT
CATCTCCATGGGTGTTCTCCCTGTGACTGTGATATTGGAGGTGCTTATTCTAACGT
GTGCTCACCCAAGAATGGGCAGTGTGAATGCCGCCCACATGTCACTGGCCGTAGC
TGCTCTGAACCAGCCCCTGGCTACTTCTTTGCTCCTTTGAATTTCTATCTCTACGAG
GCAGAGGAAGCCACAACACTCCAAGGACTGGCGCCTTTGGGCTCGGAGACGTTTG
GCCAGAGTCCTGCTGTTCACGTTGTTTTAGGAGAGCCAGTTCCTGGGAACCCTGTT
ACATGGACTGGACCTGGATTTGCCAGGGTTCTCCCTGGGGCTGGCTTGAGATTTG
CTGTCAACAACATTCCCTTTCCTGTGGACTTCACCATTGCCATTCACTATGAAACC
CAGTCTGCAGCTGACTGGACTGTCCAGATTGTGGTGAACCCCCCTGGAGGGAGTG
AGCACTGCATACCCAAGACTCTACAGTTAAAGCCTCAGTCTTTTGCCTTACCAGC
GGCTACGAGAATCATGCTGCTTCCCACACCCATCTGTTTAGAACCAGATGTACAA
TATTCCATAGATGTCTATTTTTCTCAGCCTTTGCAAGGAGAGTCCCACGCTCATTC
ACATGTCCTGGTGGACTCTCTTGGCCTTATTCCCCAAATCAATTCATTGGAGAATT
TCTGCAGCAAGCAGGACTTAGATGAGTATCAGCTTCACAACTGTGTTGAAATTGC
CTCAGCAATGGGACCTCAAGTGCTCCCGGGTGCCTGTGAAAGGCTGATCATCAGC
ATGTCTGCCAAGCTGCATGATGGGGCTGTGGCCTGCAAGTGTCACCCCCAGGGCT
CAGTCGGATCCAGCTGCAGCCGACTTGGAGGCCAGTGCCAGTGTAAACCTCTTGT
GGTCGGGCGCTGCTGTGACAGGTGCTCAACTGGAAGCTATGATTTGGGGCATCAC
GGCTGTCACCCATGTCACTGCCATCCTCAAGGATCAAAGGACACTGTATGTGACC
AAGTAACAGGACAGTGCCCCTGCCATGGAGAGGTGTCTGGCCGCCGCTGTGATCG
CTGCCTGGCAGGCTACTTTGGATTTCCCAGCTGCCACCCTTGCCCTTGTAATAGGT
TTGCTGAACTTTGTGATCCTGAGACAGGGTCATGCTTCAATTGTGGAGGCTTTACA
ACTGGCAGAAACTGTGAAAGGTGTATTGATGGTTACTATGGAAATCCTTCTTCAG
```

-continued
GACAGCCCTGTCGTCCTTGCCTGTGTCCAGATGATCCCTCAAGCAATCAGTATTTT

GCCCATTCCTGTTATCAGAATCTGTGGAGCTCAGATGTAATCTGCAATTGTCTTCA

AGGTTATACGGGTACTCAGTGTGGAGAATGCTCTACTGGTTTCTATGGAAATCCA

AGAATTTCAGGAGCACCTTGCCAACCATGTGCCTGCAACAACAACATAGATGTAA

CCGATCCAGAGTCCTGCAGCCGGGTAACAGGGGAGTGCCTTCGATGTTTGCACAA

CACTCAGGGCGCAAACTGCCAGCTCTGCAAACCAGGTCACTATGGATCAGCCCTC

AATCAGACCTGCAGAAGATGCTCCTGCCATGCTTCCGGCGTGAGTCCCATGGAGT

GTCCCCCTGGTGGGGAGCTTGCCTCTGTGACCCTGTCACTGGTGCATGTCCTTGT

CTGCCGAATGTCACAGGCCTGGCCTGTGACCGTTGTGCTGATGGATACTGGAATC

TGGTCCCTGGCAGAGGATGTCAGTCATGTGACTGTGACCCTAGGACCTCTCAAAG

TAGCCACTGTGACCAGCTTACAGGCCAGTGTCCGTGTAAATTAGGTTACGGCGGG

AAACGTTGCAGTGAGTGCCAGGAAAATTATTATGGTGATCCACCTGGGCGATGCA

TTCCATGTGATTGTAACAGGGCAGGTACCCAGAAGCCCATCTGTGATCCAGACAC

AGGCATGTGCCGCTGCCGGGAGGGTGTCAGCGGCCAGAGATGTGATCGCTGTGCC

CGGGGACACAGCCAGGAATTCCCTACTTGTCTTCAATGTCACTTGTGCTTTGATCA

GTGGGACCACACCATTTCTTCCCTCTCCAAAGCGGTGCAAGGGTTAATGAGACTG

GCTGCTAACATGGAAGATAAAAGAGAGACCCTGCCTGTCTGTGAGGCAGACTTCA

AAGACCTCAGAGGGAACGTGTCTGAAATAGAAAGGATTTTGAAACATCCTGTTTT

CCCATCTGGGAAATTCTTAAAAGTCAAGGATTATCATGACTCTGTTAGAAGACAA

ATCATGCAGCTAAATGAACAACTGAAAGCAGTGTATGAATTTCAAGATCTGAAAG

ATACAATAGAAAGAGCAAAGAATGAAGCAGACCTCTTACTTGAAGACCTTCAGG

AAGAAATTGATTTGCAATCCAGTGTCCTTAATGCAAGCATTGCGGACTCCTCAGA

AAACATCAAGAAATATTATCACATATCATCATCTGCTGAAAAGAAAATTAATGAA

ACTAGTTCCACCATTAATACCTCTGCAAATACAAGGAATGACTTACTTACCATCTT

AGATACACTAACCTCAAAAGGAAACTTGTCATTGGAAAGATTAAAGCAGATTAA

GATACCAGATATCCAAATATTGAATGAAAAGGTGTGCGGAGATCCAGGAAATGT

GCCATGTGTGCCCTTGCCCTGTGGCGGTGCTCTCTGCACGGGCCGGAAGGGGCAC

AGGAAGTGTAGGGGTCCCGGCTGTCACGGCTCCCTGACCCTCTCAACGAATGCCC

TCCAAAAAGCCCAGGAAGCAAAATCCATTATTCGTAATTTGGACAAACAGGTTCG

TGGGTTGAAAAATCAGATCGAAAGTATAAGTGAACAGGCAGAAGTCTCCAAAAA

CAATGCCTTACAGCTGAGGGAAAAACTGGGAAATATAAGAAACCAAAGTGACTC

TGAAGAAGAAAACATCAATCTTTTCATCAAAAAAGTGAAAAACTTTTTGTTAGAG

GAAAACGTGCCTCCAGAAGACATCGAGAAGGTTGCGAATGGTGTGCTTGACATTC

ACCTACCAATTCCATCCCAAAATCTAACCGATGAACTTGTCAAAATACAGAAACA

TATGCAACTCTGTGAGGATTACAGGACAGATGAAAACAGGTTAAATGAAGAAGC

AGATGGAGCCCAAAAGCTTTTGGTGAAGGCCAAAGCAGCTGAGAAAGCAGCAAA

TATTCTATTAAATCTTGACAAAACATTGAACCAGTTACAACAAGCTCAAATCACT

CAAGGACGGGCAAACTCTACCATTACACAGCTGACTGCCAATATAACAAAAATA

AAAAAGAATGTGCTGCAGGCTGAAAATCAAACCAGGGAAATGAAGAGTGAGCTG

GAGTTAGCAAAGCAGCGATCAGGGCTGGAGGATGGACTTTCCCTGCTGCAGACCA

AGTTGCAAAGGCATCAAGACCACGCTGTCAATGCGAAAGTTCAGGCTGAATCTGC

-continued

```
CCAACACCAGGCTGGGAGTCTTGAGAAGGAATTTGTTGAGCTGAAAAAACAATAT
GCTATTCTCCAACGTAAGACAAGCACTACAGGACTAACAAAGGAGACATTAGGA
AAAGTTAAACAGCTAAAAGATGCGGCAGAAAAATTGGCTGGAGATACAGAGGCC
AAGATAAGAAGAATAACAGATTTAGAAAGGAAAATCCAAGATTTGAATCTAAGT
AGACAAGCAAAAGCTGATCAACTGAGAATATTGGAAGATCAAGTTGTTGCCATTA
AAAATGAAATTGTTGAACAAGAAAAAAAATATGCTAGGTGCTATAGCTAGCTCG
AGCACCACCATCACCATCACCATCACTAAGTGATTAACCTCAGGTGCAGGCTGCC
TATCAGAAGGTGGTGGCTGGTGTGGCCAATGCCCTGGCTCACAAATACCACTGAG
ATCGATCTTTTTCCCTCTGCCAAAAATTATGGGGACATCATGAAGCCCCTTGAGCA
TCTGACTTCTGGCTAATAAAGGAAATTTATTTTCATTGCAATAGTGTGTTGGAATT
TTTTGTGTCTCTCACTCGGAAGGACATATGGGAGGGCAAATCATTTAAAACATCA
GAATGAGTATTTGGTTTAGAGTTTGGCAACATATGCCCATATGTAACTAGCATAA
CCCCTTGGGGCCTCTAAACGGGTCTTGAGGGGTTTTTTGCTGAAAGCATGCGGAG
GAAATTCTCCTTGAAGTTTCCCTGGTGTTCAAAGTAAAGGAGTTTGCACCAGACG
CACCTCTGTTCACTGGTCCGGCGTATTAAAACACGATACATTGTTATTAGTACATT
TATTAAGCGCTAGATTCTGTGCGTTGTTGATTTACAGACAATTGTTGTACGTATTT
TAATAATTCATTAAATTTATAATCTTTAGGGTGGTATGTTAGAGCGAAAATCAAAT
GATTTTCAGCGTCTTTATATCTGAATTTAAATATTAAATCCTCAATAGATTTGTAA
AATAGGTTTCGATTAGTTTCAAACAAGGGTTGTTTTTCCGAACCGATGGCTGGACT
ATCTAATGGATTTTCGCTCAACGCCACAAAACTTGCCAAATCTTGTAGCAGCAAT
CTAGCTTTGTCGATATTCGTTTGTGTTTTGTTTTGTAATAAAGGTTCGACGTCGTTC
AAAATATTATGCGCTTTTGTATTTCTTTCATCACTGTCGTTAGTGTACAATTGACTC
GACGTAAACACGTTAAATAGAGCTTGGACATATTTAACATCGGGCGTGTTAGCTT
TATTAGGCCGATTATCGTCGTCGTCCCAACCCTCGTCGTTAGAAGTTGCTTCCGAA
GACGATTTTGCCATAGCCACACGACGCCTATTAATTGTGTCGGCTAACACGTCCG
CGATCAAATTTGTAGTTGAGCTTTTTGGAATTATTTCTGATTGCGGGCGTTTTTGG
GCGGGTTTCAATCTAACTGTGCCCGATTTTAATTCAGACAACACGTTAGAAAGCG
ATGGTGCAGGCGGTGGTAACATTTCAGACGGCAAATCTACTAATGGCGGCGGTGG
TGGAGCTGATGATAAATCTACCATCGGTGGAGGCGCAGGCGGGGCTGGCGGCGG
AGGCGGAGGCGGAGGTGGTGGCGGTGATGCAGACGGCGGTTTAGGCTCAAATGT
CTCTTTAGGCAACACAGTCGGCACCTCAACTATTGTACTGGTTTCGGGCGCCGTTT
TTGGTTTGACCGGTCTGAGACGAGTGCGATTTTTTTCGTTTCTAATAGCTTCCAAC
AATTGTTGTCTGTCGTCTAAAGGTGCAGCGGGTTGAGGTTCCGTCGGCATTGGTG
GAGCGGGCGGCAATTCAGACATCGATGGTGGTGGTGGTGGAGGCGCTGGAA
TGTTAGGCACGGGAGAAGGTGGTGGCGGCGGTGCCGCCGGTATAATTTGTTCTGG
TTTAGTTTGTTCGCGCACGATTGTGGGCACCGGCGCAGGCGCCGCTGGCTGCACA
ACGGAAGGTCGTCTGCTTCGAGGCAGCGCTTGGGGTGGTGGCAATTCAATATTAT
AATTGGAATACAAATCGTAAAAATCTGCTATAAGCATTGTAATTTCGCTATCGTTT
ACCGTGCCGATATTTAACAACCGCTCAATGTAAGCAATTGTATTGTAAAGAGATT
GTCTCAAGCTCGGAACGCTGCGCTCGGTCGTTCGGCTGCGGCGAGCGGTATCAGC
```

```
TCACTCAAAGGCGGTAATACGGTTATCCACAGAATCAGGGGATAACGCAGGAAA

GAACATGTGAGCAAAAGGCCAGCAAAAGGCCAGGAACCGTAAAAAGGCCGCGTT

GCTGGCGTTTTTCCATAGGCTCCGCCCCCCTGACGAGCATCACAAAAATCGACGC

TCAAGTCAGAGGTGGCGAAACCCGACAGGACTATAAAGATACCAGGCGTTTCCCC

CTGGAAGCTCCCTCGGTCGCTCTCCTGTTCCGACCCTGCCGCTTACCGGATACCTG

TCCGCCTTTCTCCCTTCGGGAAGCGTGGCGCTTTCTCAATGCTCACGCTGTAGGTA

TCTCAGTTCGGTGTAGGTCGTTCGCTCCAAGCTGGGCTGTGTGCACGAACCCCCCG

TTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCG

AGGTATGTAGGCGGTGCTACAGAGTTCTTGAAGTGGTGGCCTAACTACGGCTACA

CTAGAAGGACAGTATTTGGTATCTGCGCTCTGCTGAAGCCAGTTACCTTCGGAAA

AAGAGTTGGTAGCTCTTGATCCGGCAAACAAACCACCGCTGGTAGCGGTGGTTTT

TTTGTTTGCAAGCAGCAGATTACGCGCAGAAAAAAAGGATCTCAAGAAGATCCTT

TGTTACCAATGCTTAATCAGTGAGGCACCTATCTCAGCGATCTGTCTATTTCGTTC

ATCCATAGTTGCCTGACTCCCCGTCGTGTAGATAACTACGATACGGGAGGGCTTA

CCATCTGGCCCCAGTGCTGCAATGATACCGCGAGACCCACGCTCACCGGCTCCAG

ATTTATCAGCAATAAACCAGCCAGCCGGAAGGGCCGAGCGCAGAAGTGGTCCTG

CAACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTGGT

GTCACGCTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCAGCAC

TGCATAATTCTCTTACTGTCATGCCATCCGTAAGATGCTTTTCTGTGACTGGTGAG

TACTCAACCAAGTCATTCTGAGAATAGTGTATGCGGCGACCGAGTTGCTCTTGCC

CGGCGTCAATACGGGATAATACCGCGCCACATAGCAGAACTTTAAAAGTGCTCAT

CATTGGAAAACGTTCTTCGGGGCGAAAACTCTCAAGGATCTTACCGCTGTTGAGA

TCCAGTTCGATGTAACCCACTCGTGCACCCAACTGATCTTCAGCATCTTTTACTTT

CACCAGCGTTTCTGGGTGAGCAAAAACAGGAAGGCAAAATGCCGCAAAAAAGGG

AATAAGGGCGACACGGAAATGTTGAATACTCATACTCTTCCTTTTTCAATATTATT

GAAGCATTTATCAGGGTTATTGTCTCATGTCCGCGCGTTTCCTGCATCTTTTAATC

AAATCCCAAGATGTGTATAAACCACCAAACTGCCAAAAAATGAAAACTGTCGAC

AAGCTCTGTCCGTTTGCTGGCAACTGCAAGGGTCTCAATCCTATTTGTAATTATTG

AATAATAAAACAATTATAAATGTCAAATTTGTTTTTTATTAACGATACAAACCAA

ACGCAACAAGAACATTTGTAGTATTATCTATAATTGAAAACGCGTAGTTATAATC

GCTGAGGTAATATTTAAAATCATTTTCAAATGATTCACAGTTAATTTGCGACAATA

TAATTTTATTTTCACATAAACTAGACGCCTTGTCGTCTTCTTCTTCGTATTCCTTCT

CTTTTTCATTTTTCTCTTCATAAAAATTAACATAGTTATTATCGTATCCATATATGT

ATCTATCGTATAGAGTAAATTTTTTGTTGTCATAAATATATATGTCTTTTTTAATGG

GGTGTATAGTACCGCTGCGCATAGTTTTTCTGTAATTTACAACAGTGCTATTTTCT

GGTAGTTCTTCGGAGTGTGTTGCTTTAATTATTAAATTTATATAATCAATGAATTT

GGGATCGTCGGTTTTGTACAATATGTTGCCGGCATAGTACGCAGCTTCTTCTAGTT
```

-continued

```
CAATTACACCATTTTTTAGCAGCACCGGATTAACATAACTTTCCAAAATGTTGTAC

GAACCGTTAAACAAAAACAGTTCACCTCCCTTTTCTATACTATTGTCTGCGAGCAG

TTGTTTGTTGTTAAAAATAACAGCCATTGTAATGAGACGCACAAACTAATATCAC

AAACTGGAAATGTCTATCAATATATAGTTGCTCTAGTTATTAATAGTAATCAATTA

CGGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGA

CTATTTACGGTAAACTGCCCACTTGGCAGTACATCAAGTGTATCATATGCCAAGT

ACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCT

ATTACCATGCATGGTCGAGGTGAGCCCCACGTTCTGCTTCACTCTCCCCATCTCCC

CCCCCTCCCCACCCCCAATTTTGTATTTATTTATTTTTTAATTATTTTGTGCAGCGA

TGGGGGCGGGGGGGGGGGGGGCGCGCGCCAGGCGGGGCGGGGCGGGGCGAG

GGGCGGGGCGGGGCGAGGCGGAGAGGTGCGGCGGCAGCCAATCAGAGCGGCGC

GCTCCGAAAGTTTCCTTTTATGGCGAGGCGGCGGCGGCGGCGGCCCTATAAAAAG

CGAAGCGCGCGGCGGGCG
```

SEQ ID NO7: >LAMB4-His - human laminin beta-4 with His-tag
MQFQLTLFLHLGWLSYSKAQDDCNRGACHPTTGDLLVGRNTQLMASSTCGLSRAQK

YCILSYLEGEQKCFICDSRFPYDPYDQPNSHTIENVIVSFEPDREKKWWQSENGLDHV

SIRLDLEALFRFSHLILTFKTFRPAAMLVERSTDYGHNWKVFKYFAKDCATSFPNITSG

QAQGVGDIVCDSKYSDIEPSTGGEVVLKVLDPSFEIENPYSPYIQDLVTLTNLRINFTK

LHTLGDALLGRRQNDSLDKYYYALYEMIVRGSCFCNGHASECRPMQKMRGDVFSPP

GMVHGQCVCQHNTDGPNCERCKDFFQDAPWRPAADLQDNACRSCSCNSHSSRCHF

DMTTYLASGGLSGGVCEDCQHNTEGQHCDRCRPLFYRDPLKTISDPYACIPCECDPD

GTISGGICVSHSDPALGSVAGQCLCKENVEGAKCDQCKPNHYGLSATDPLGCQPCDC

NPLGSLPFLTCDVDTGQCLCLSYVTGAHCEECTVGYWGLGNHLHGCSPCDCDIGGA

YSNVCSPKNGQCECRPHVTGRSCSEPAPGYFFAPLNFYLYEAEEATTLQGLAPLGSET

FGQSPAVHVVLGEPVPGNPVTWTGPGFARVLPGAGLRFAVNNIPFPVDFTIAIHYETQ

SAADWTVQIVVNPPGGSEHCIPKTLQSKPQSFALPAATRIMLLPTPICLEPDVQYSIDV

YFSQPLQGESHAHSHVLVDSLGLIPQINSLENFCSKQDLDEYQLHNCVEIASAMGPQV

LPGACERLIISMSAKLHDGAVACKCHPQGSVGSSCSRLGGQCQCKPLVVGRCCDRCS

TGSYDLGHHGCHPCHCHPQGSKDTVCDQVTGQCPCHGEVSGRRCDRCLAGYFGFPS

CHPCPCNRFAELCDPETGSCFNCGGFTTGRNCERCIDGYYGNPSSGQPCRPCLCPDDP

SSNQYFAHSCYQNLWSSDVICNCLQGYTGTQCGECSTGFYGNPRISGAPCQPCACNN

NIDVTDPESCSRVTGECLRCLHNTQGANCQLCKPGHYGSALNQTCRRCSCHASGVSP

MECPPGGGACLCDPVTGACPCLPNVTGLACDRCADGYWNLVPGRGCQSCDCDPRTS

QSSHCDQLTGQCPCKLGYGGKRCSECQENYYGDPPGRCIPCDCNRAGTQKPICDPDT

GMCRCREGVSGQRCDRCARGHSQEFPTCLQCHLCFDQWDHTISSLSKAVQGLMRLA

ANMEDKRETLPVCEADFKDLRGNVSEIERILKHPVFPSGKFLKVKDYHDSVRRQIMQ

LNEQLKAVYEFQDLKDTIERAKNEADLLLEDLQEEIDLQSSVINASIADSSENIKKYY

HISSSAEKKINETSSTINTSANTRNDLLTILDTLTSKGNLSLERLKQIKIPDIQILNEKVC

-continued

```
GDPGNVPCVPLPCGGALCTGRKGHRKCRGPGCHGSLTLSTNALQKAQEAKSIIRNLD

KQVRGLKNQIESISEQAEVSKNNALQLREKLGNIRNQSDSEEENINLFIKKVKNFLEE

NVPPEDIEKVANGVLDIHLPIPSQNLTDELVKIQKHMQLCEDYRTDENRLNEEADGAQ

KLLVKAKAAEKAANILLNLDKTLNQLQQAQITQGRANSTITQLTANITKIKKNVLQAE

NQTREMKSELELAKQRSGLEDGLSLLQTKQRHQDHAVNAKVQAESAQHQAGSLEK

EFVELKKQYAILQRKTSTTGLTKETLGKVKQLKDAAEKLAGDTEAKIRRITDLERKIQ

DLNLSRQAKADQLRILEDQVVAIKNEIVEQEKKYARCYSLEHHHHHHHH

SEQ ID NO 8: Autoantibody epitope 1
EFQDL

SEQ ID NO 9: Autoantibody epitope 2
ADLLLEDLQE

SEQ ID NO 10: Autoantibody epitope 3
ADLLLEDLQEEIDLQS

SEQ ID NO 11: Autoantibody epitope 4
DLLTILDTLISK

SEQ ID NO 12: Autoantibody epitope 5
QIKIPDIQILNEK

SEQ ID NO 13: Autoantibody epitope 6
VRGLKNQIESISE

SEQ ID NO 14: Autoantibody epitope 7
LLEENVPPEDI

SEQ ID NO 15: Subfragment 1
MQDDCNRGACHPTTGDLLVGRNTQLMASSTCGLSRAQKYCILSYLEGEQKCFICDSR

FPYDPYDQPNSHTIENVIVSFEPDREKKWWQSENGLDHVSIRLDLEALFRFSHLILTFK

TFRPAAMLVERSTDYGHNWKVFKYFAKDCATSFPNITSGQAQGVGDIVCDSKYSDIE

PSTGGEVVLKVLDPSFEIENPYSPYIQDLVTLTNLRINFTKLHTLGDALLGRRQNDSLD

KYYYALYEMIVRGSCFCNGHASECRPMQKMRGDVFSPPGMVHGQCVCQHNTDGPN

CERCKDFFQDAPW

SEQ ID NO 16: Subfragment 2
MPNCERCKDFFQDAPWRPAADLQDNACRSCSCNSHSSRCHFDMTTYLASGGLSGGV

CEDCQHNTEGQHCDRCRPLFYRDPLKTISDPYACIPCECDPDGTISGGICVSHSDPALG

SVAGQCLCKENVEGAKCDQCKPNHYGLSATDPLGCQPCDCNPLGSLPFLTCDVDTG

QCLCLSYVTGAHCEECTVGYWGLGNHLHGCSPCDCDIGGAYSNVCSPKNGQCECRP

HVTGRSCSEPAPGYFFAPLNFYLYEAEEATTLQGLAPLGSETFGQSPAVHVVLGEPVP

GNPVTWTGPGFARVLW

SEQ ID NO 17: Subfragment 3
MGNPVTWTGPGFARVLPGAGLRFAVNNIPFPVDFTIAIHYETQSAADWTVQIVVNPP

GGSEHCIPKTLQSKPQSFALPAATRIMLLPTPICLEPDVQYSIDVYFSQPLQGESHAHSH

VLVDSLGLIPQINSLENFCSKQDLDEYQLHNCVEIASAMGPQVLPGACERLIISMSAKL

HDGAVACKCHPQGSVGSSCSRLGGQCQCKPLVVGRCCDRCSTGSYDLGHHGCHPCH

CHPQGSKDTVCDQVTGQCPCHGEVSGRRCDRCLAGYFGFPSCHPCPCNRFAELCDPE

TGSCFNCGGFTTGRNCERCIDGYYGNWGW

SEQ ID NO 18: Subfragment 4
MTGRNCERCIDGYYGNPSSGQPCRPCLCPDDPSSNQYFAHSCYQNLWSSDVICNCLQ

GYTGTQCGECSTGFYGNPRISGAPCQPCACNNNIDVTDPESCSRVTGECLRCLHNTQG

ANCQLCKPGHYGSALNQTCRRCSCHASGVSPMECPPGGGACLCDPVTGACPCLPNV
```

TGLACDRCADGYWNLVPGRGCQSCDCDPRTSQSSHCDQLTGQCPCKLGYGGKRCSE

CQENYYGDPPGRCIPCDCNRAGTQKPICDPDTGMCRCREGVSGQRCDRCARGHSQE

WGW

SEQ ID NO 19: Subfragment 5
MSGQRCDRCARGHSQEFPTCLQCHLCFDQWDHTISSLSKAVQGLMRLAANMEDKRE

TLPVCEADFKDLRGNVSEIERILKHPVFPSGKFLKVKDYHDSVRRQIMQLNEQLKAV

YEFQDLKDTIERAKNEADLLLEDLQEEIDLQSSVNASIADSSENIKKYYHISSSAEKKI

NETSSTINTSANTRNDLLTILDTLTSKGNLSLERLKQIKIPDIQILNEKVCGDPGNVPCV

PLPCGGALCTGRKGHRKCRGPGCHGSLTLSTNALQKAQEAKSIIRNLDKQVRGLKNQ

IESISEQAEVSKNNALQLREKLGNIWGWGW

SEQ ID NO 20: Subfragment 6
MSKNNALQLREKLGNIRNQSDSEEENINLFIKKVKNFLLEENVPPEDIEKVANGVLDI

HLPIPS1NLTDELVKIQKHMQLCEDYRTDENRLNEEADGAQKLLVKAKAAEKAANIL

LNLDKTLNQLQQAQITQGRANSTITQLTANITKIKKNVLQAENQTREMKSELELAKQ

RSGLEDGLSLLQTKLQRHQDHAVNAKVQAESAQHQAGSLEKEFVELKKQYAILQRK

TSTTGLTKETLGKVQLKDAAEKLAGDTEAKIRRITDLERKIQDLNLSRQAKADQLRI

LEDQVVAIKNEIVEQEKKYARCYSWGWGWGW

SEQ ID NO 21: Subfragment 1, with four tryptophans and C-terminal His-tag (AMB4-
TF1-4W-His)
MQDDCNRGACHPTTGDLLVGRNTQLMASSTCGLSRAQKYCILSYLEGEQKCFICDSR

FPYDPYDQPNSHTIENVIVSFEPDREKKWWQSENGLDHVSIRLDLEALFRFSHLILTFK

TFRPAAMLVERSTDYGHNWKVFKYFAKDCATSFPNITSGQAQGVGDIVCDSKYSDIE

PSTGGEVVLKVLDPSFIEIENPYSPYIQDLVTLTNLRINFTKLHTLGDALLGRRQNDSLD

KYYYALYEMIVRGSCFCNGHASECRPMQKMRGDVFSPPGMVHGQCVCQHNTDGPN

CERCKDFFQDAPWLEHHHHHH

SEQ ID NO 22: Subfragment 2, with four tryptophans and C-terminal His-tag
(LAMB4-TF2-4W-His)
MPNCERCKDFFQDAPWRPAADLQDNACRSCSCNSHSSRCHFDMTTYLASGGLSGGV

CEDCQHNTEGQHCDRCRPLFYRDPLKTISDPYACIPCECDPDGTISGGICVSHSDPALG

SVAGQCLCKENVEGAKCDQCKPNHYGLSATDPLGCQPCDCNPLGSLPFLTCDVDTG

QCLCLSYVTGAHCEECTVGYWGLGNHLHGCSPCDCDIGGAYSNVCSPKNGQCECRP

HVTGRSCSEPAPGYFFAPLNFYLYEAEEATTLQGLAPLGSETFGQSPAVHVVLGEPVP

GNPVTWTGPGFARVLWLEHHHHHH

SEQ ID NO 23: Subfragment 3, with four tryptophans and C-terminal His-tag
(LAMB4-TF3-4W-His)
MGNPVTWTGPGFARVLPGAGLRFAVNNIPFPVDFTIAIHYETQSAADWTVQIVVNPP

GGSEHCIPKTLQSKPQSFALPAATRIMLLPTPICLEPDVQYSIDVYFSQPLQGESHAHSH

VLVDSLGLIPQINSLENFCSKQDLDEYQLHNCVEIASAMGPQVLPGACERLIISMSAKL

HDGAVACKCHPQGSVGSSCSRLGGQCQCKPLVVGRCCDRCSTGSYDLGHHGCHPCH

CHPQGSKDTVCDQVTGQCPCHGEVSGRRCDRCLAGYFGFPSCHPCPCNRFAELCDPE

TGSCFNCGGFTTGRNCERCIDGYYGNWGWLEHHHHHH

SEQ ID NO 24: Subfragment 4, with four tryptophans and C-terminal His-tag
(LAMB4-TF4-4W-His)
MTGRNCERCIDGYYGNPSSGQPCRPCLCPDDPSSNQYFAHSCYQNLWSSDVICNCLQ

GYTGTQCGECSTGFYGNPRISGAPCQPCACNNNIDVTDPESCSRVTGECLRCLHNTQG

-continued

ANCQLCKPGHYGSALNQTCRRCSCHASGVSPMECPPGGGACLCDPVTGACPCLPNV

TGLACDRCADGYWNLVPGRGCQSCDCDPRTSQSSHCDQLTGQCPCKLGYGGKRCSE

CQENYYGDPPGRCIPCDCNRAGTQKPICDPDTGMCRCREGVSGQRCDRCARGHSQE

WGWLEHHHHHH

SEQ ID NO 25: Subfragment 5, with four tryptophans and C-terminal His-tag
(LAMB4-TF5-4W-His)
MSGQRCDRCARGHSQEFPTCLQCHLCFDQWDHTISSLSKAVQGLMRLAANMEDKRE

TLPVCEADFKDLRGNVSEIERILKHPVFPSGKFLKVKDYHDSVRRQIMQLNEQLKAV

YEFQDLKDTIERAKNEADLLLEDLQEEIDLQSSVLNASIADSSENIKKYYHISSSAEKKI

NETSSTINTSANTRNDLLTILDTLTSKGNLSLERLKQIKIPDIQILNEKVCGDPGNVPCV

PLPCGGALCTGRKGHRKCRGPGCHGSLTLSTNALQKAQEAKSIIRNLDKQVRGLKNQ

IESISEQAEVSKNNALQLREKLGNIWGWGWLEHHHHHH

SEQ ID NO 26: Subfragment 6, with four tryptophans and C-terminal His-tag
(LAMB4-TF6-4W-His)
MSKNNALQLREKLGNIRNQSDSEEENINLFIKKVKNFLLEENVPPEDIEKVANGVLDI

HLPIPSQNLTDELVKIQKHMQLCEDYRTDENRLNEEADGAQKLLVKAKAAEKAANIL

LNLDKTLNQLQQAQITQGRANSTITQLTANITKIKKNVLQAENQTREMKSELELAKQ

RSGLEDGLSLLQTKLQRHQDHAVNAKVQAESAQHQAGSLEKEFVELKKQYAILQRK

TSTTGLTKETLGKVKQLKDAAEKLAGDTEAKIRRITDLERKIQDLNLSRQAKADQLRI

LEDQVVAIKNEIVEQEKKVARCYSWGWGWGWLEHHHHHH

SEQ ID NO 27: Laminin beta-4
MQFQLTFLHLGWLSYSKAQDDCNRGACHPTTGDLLVGRNTQLMASSTCGLSRAQK

YCILSYLEGEQKCFICDSRFPYDPYDQPNSHTIENVIVSFEPDREKKWWQSENGLDHV

SIRLDLEALFRFSHLILTFKTFRPAAMLVERSTDYGHNWKVFKYFAKDCATSFPNITSG

QAQGVGDIVCDSKYSDIEPSTGGEVVLKVLDPSFEIENPYSTYIQDLVTLTNLRINFTK

LHTLGDALLGRRQNDSLDKYYYALYEMIVRGSCFCNGHASECRPMQKMRGDVFSPP

GMVHGQCVCQHNTDGPNCERCKDFFQDAPWRPAADLQDNACRSCSCNSHSSRCHF

DMTTYLASGGLSGGVCEDCQHNTEGQHCDRCRPLFYRDPLKTISDPYACIPCECDPD

GTISGGICVSHSDPALGSVAGQCLCKENVEGAKCDQCKPNHYGLSATDPLGCQPCDC

NPLGSLPFLTCDVDTGQCLCLSYVTGAHCEECTVGYWGLGNHLHGCSPCDCDIGGA

YSNVCSPKNGQECRPHVTGRSCSEPAPGYFFAPLNFYLYEAEEEATTLQGLAPLGSET

FGQSPAVHVVLGEPVPGNPVTWTGPGFARVLPGAGLRFAVNNIPFPVDFTIAIHYETQ

SAADWTVQIVVNPPGGSEHCIPKTLQSKPQSFALPAATRIMLLPTPICLEPDVQYSIDV

YFSQPLQGESHAHSHVLVDSLGLIPQINSLENFCSKQDLDEYQLHNCVEIASAMGPQV

LPGACERLIISMSAKLHDGAVACKCHPQGSVGSSCSRLGGQCQCKPLVVGRCCDRCS

TGSYDLGHHGCHPCHCHPQGSKDTVCDQVTGQCPCHGEVSGRRCDRCLAGYFGFPS

CHPCPCNRFAELCDPETGSCFNCGGFTTGRNCERCIDGYYGNPSSGQPCRPCLPDDP

SSNQYFAHSCYQNLWSSDVICNCLQGYTGTQCGECSTGFYGNPRISGAPCQPCACNN

NIDVTDPESCSRVTGECLRCLHNTQGANCQLCKPGHYGSALNQTCRRCSCHASGVSP

MECPPGGGACLCDPVTGACPCLPNVTGLACDRCADGYWNLVPGRGCQSCDCDPRTS

QSSHCDQLTGQCPCKLGYGGKRCSECQENYYGDPPGRCIPCDCNRAGTQKPICDPDT

GMCRCREGVSGQRCDRCARGHSQEFPTCLQCHLCFDQWDHTISSLSKAVQGLMRLA

ANMEDKRETLPVCEADFKDLRGNVSEIERILKHPVFPSGKFLKVKDYHDSVRRQIMQ

-continued

LNEQLKAVYEFQDLKDTIERAKNEADLLLEDLQEEIDLQSSVLNASIADSSENIKKYY

HISSSAEKKINETSSTINTSANTRNDLLTILDTLTSKGNLSLERLKQIKIPDIQILNEKVC

GDPGNVPCVPLPCGGALCTGRKGHRKCRGPGCHGSLTLSTNALQKAQEAKSIIRNLD

KQVRGLKNQIESISEQAEVSKNNALQLREKLGNIRNQSDSEEENINLFIKKVKNFLLEE

NVPPEDIEKVANGVLDIHLPIPSQNLTDELVKIQKHMQLCEDYRTDENRLNEEADGAQ

KLLVKAKAAEKAANILLNLDKTLNQLQQAQITQGRANSTITQLTANITKIKKNVLQAE

NQTREMKSELELAKQRSGLEDGLSLLQTKLQRHQDHAVNAKVQAESAQHQAGSLEK

EFVELKKQYAILQRKTSTTGLTKETLGKVKQLKDAAEKLAGDTEAKIRRITDLERKIQ

DLNLSRQAKADQLRILEDQVVAIKNEIVEQEKKYARCYS

SEQ ID NO 28: SEQ ID NO 8 from EP3260864
MDCTFKPDFEMTVKECQHSGELSSRNTGHLHPTPRSPLLRWTQEPQPLEEKWQHRVV

EQIPKEVQFQPPGAPLEKEKSQQCYSEYFSQTSTELQITFDETNPITRLSEIEKIRDQALN

NSRPPVRYQDNACEMELVKVLTPLEIAKNKQYDMHTEVTTLKQEKNPVPSAEEWML

EGCRASGGLKKGDFLKKGLEPETFQNFDGDHACSVRDDEFKFQGLRHTVTARQLVE

AKLLDMRTIEQLRLGLKTVEEVQKTLNKFLTKATSIAGLYLESTKEKISFASAAERIIID

KMVALAFLEAQAATGFIIDPISGQTYSVEDAVLKGVVDPEFRIRLLEAEKAAVGYSYS

SKTLSVFQAMENRMLDRQKGKHILEAQIASGGVIDPVRGIRVPPEIALQQGLLNNAIL

QFLHEPSSNTRVFPNPNNKQALYYSELLRMCVFDVESQCFLFPFGERNISNLNVKKTH

RISVVDTKTGSELTVYEAFQRNLIEKSIYLELSGQQYQWKEAMFFESYGHSSHMLTDT

KTGLHFNINEAIEQGTIDKALVKKYQEGLITLTELADSLLSRLVPKKDLHSPVAGYWL

TASGERISVLKASRRNLVDRITALRCLEAQVSTGGIIDPLTGKKYRVAEALHRGLVDE

GFAQQLRQCELVITGIGHPITNKMMSVVEAVNANIINKEMGIRCLEFQYLTGGLIEPQ

VHSRLSIEEALQVGIIDVLIATKLKDQKSYVRNIICPQTKRKLTYKEALEKADFDFHTG

LKLLEVSEPLMTGISSLYYSSLLE

SEQ ID NO 29: Gliadin peptide
LGQQQPFPPQQPYPQPQPFPSQQPY

SEQ ID NO 30: Gliadin peptide
QLQPFPQPELPYPQPQS

SEQ ID NO 31: Gliadin peptide
QQLPQPEQPQQSFPEQERPF

The invention is elucidated below on the basis of exemplary embodiments with reference to the figures. The embodiments described are merely exemplary in every respect and not to be understood as limiting, and various combinations of the features cited are encompassed by the scope of the invention.

FIG. 1 shows an immunoprecipitation with anti-p200 pemphigoid patient IgG or serum without LAMC1 reactivity and extract of human dermis. A: Western blot analysis: detection of the immunoprecipitated proteins by incubation with an anti-p200 pemphigoid serum as primary antibody (dilution 1:50). Lane 1: anti-p200 IgG (purified) without LAMC1-cterm reactivity; lane 2: anti-p200 pemphigoid serum without LAMC1-cterm reactivity; lane 3: normal human IgG (purified); lane 4: normal human serum; lane 5: Gammabind G Sepharose on its own. B: Silver blue (Coomassie) staining of a gel containing the same samples as in A. Bands 1, 2 and 3 were cut out and subjected to an LC-MS/MS analysis. Laminin beta-4 was identified as possible autoantigen (bands 1 and 2).

Figure 2:
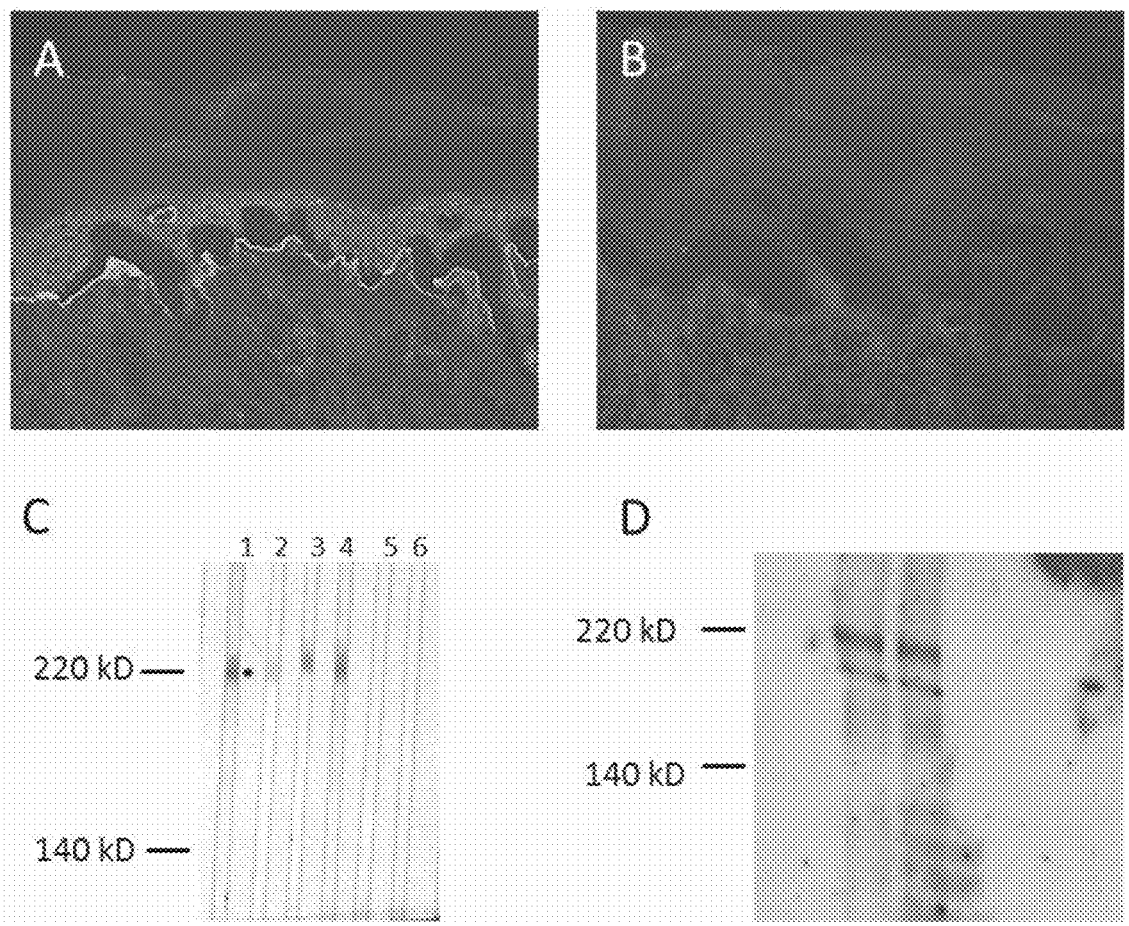
FIG. 2 shows the detection of laminin beta-4 in the skin. A, B: Indirect immunofluorescence microscopy: staining of laminin beta-4 on the dermal side of the artificial split in salt-split human skin with the aid of a commercial polyclonal antibody (Cloud-Clone: PAC079Hu01). B: Negative control. C: Testing of the laminin beta-4 antibody in urea extracts of human dermis by means of western blot analysis. Strips 1 and 2: anti-200 pemphigoid sera; strip 3: laminin gamma 1 antibody: strip 4: laminin beta-4 antibody: strips 5 and 6: normal human sera. D: Immunoprecipitation with laminin beta-4 antibody and extract of human dermis followed by western blot analysis (staining with a pool of anti-p200 pemphigoid patient IgG without laminin gamma 1 reactivity). Lanes 1 and 2: anti-laminin beta-4 antibody (5 µg and 10 µg, respectively); lane 3: anti-NC16A IgG (control IgG, 10 µg); lane 4: normal rabbit IgG (10 µg); lane 5: Gammabind G Sepharose on its own.

FIG. 2 shows the detection of laminin beta-4 in the skin. A, B: Indirect immunofluorescence microscopy: staining of laminin beta-4 on the dermal side of the artificial split in salt-split human skin with the aid of a commercial polyclonal antibody (Cloud-Clone: PAC079Hu01). B: Negative control. C: Testing of the laminin beta-4 antibody in urea extracts of human dermis by means of western blot analysis. Strips 1 and 2: anti-200 pemphigoid sera; strip 3: laminin gamma 1 antibody: strip 4: laminin beta-4 antibody: strips 5 and 6: normal human sera. D: Immunoprecipitation with laminin beta-4 antibody and extract of human dermis followed by western blot analysis (staining with a pool of anti-p200 pemphigoid patient IgG without laminin gamma 1 reactivity). Lanes 1 and 2: anti-laminin beta-4 antibody (5 µg and 10 µg, respectively); lane 3: anti-NC16A IgG (control IgG, 10 µg); lane 4: normal rabbit IgG (10 µg); lane 5: Gammabind G Sepharose on its own.

Figure 3:
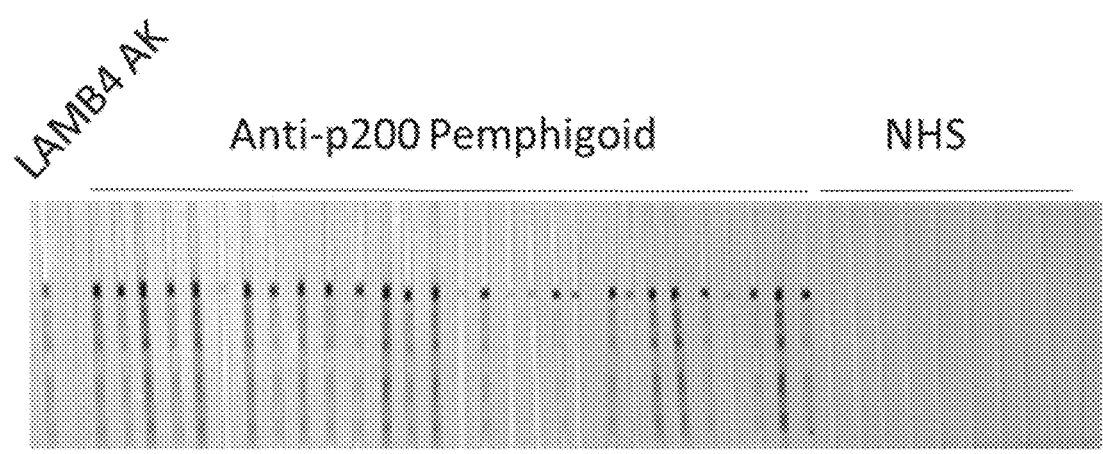
FIG. 3 shows a representative western blot analysis with laminin beta-4-expressing HEK293 cells and anti-p200 pemphigoid sera (n=29). HEK293 cells were transfected with LAMB4-pTriEx1 (jetPRIME: Polyplus) and lysed in RIPA buffer after 48 h. The protein extract was resolved by means of SDS-PAGE, the proteins were transferred to a nitrocellulose membrane, and the membrane was blocked and was incubated overnight with the laminin beta-4 antibody (commercial polyclonal antibody from Cloud-Clone; 1:2000), the anti-p200 pemphigoid sera (1:50) and the normal human sera (NHS, 1:50) from healthy blood donors. An anti-human IgG4 HRP conjugate (1:2000) was used as secondary antibody. The blot was developed with DAB for 1 min. All the anti-p200 pemphigoid sera shown here reacted with laminin beta-4, while the controls exhibited no reaction.

FIG. 3 shows a representative western blot analysis with laminin beta-4-expressing HEK293 cells and anti-p200 pemphigoid sera (n=29). HEK293 cells were transfected with LAMB4-pTriEx1 (jetPRIME: Polyplus) and lysed in RIPA buffer after 48 h. The protein extract was resolved by means of SDS-PAGE, the proteins were transferred to a nitrocellulose membrane, and the membrane was blocked and was incubated overnight with the laminin beta-4 antibody (commercial polyclonal antibody from Cloud-Clone; 1:2000), the anti-p200 pemphigoid sera (1:50) and the normal human sera (NHS, 1:50) from healthy blood donors. An anti-human IgG4 HRP conjugate (1:2000) was used as secondary antibody. The blot was developed with DAB for 1 min. All the anti-p200 pemphigoid sera shown here reacted with laminin beta-4, while the controls exhibited no reaction.

Figure 4:
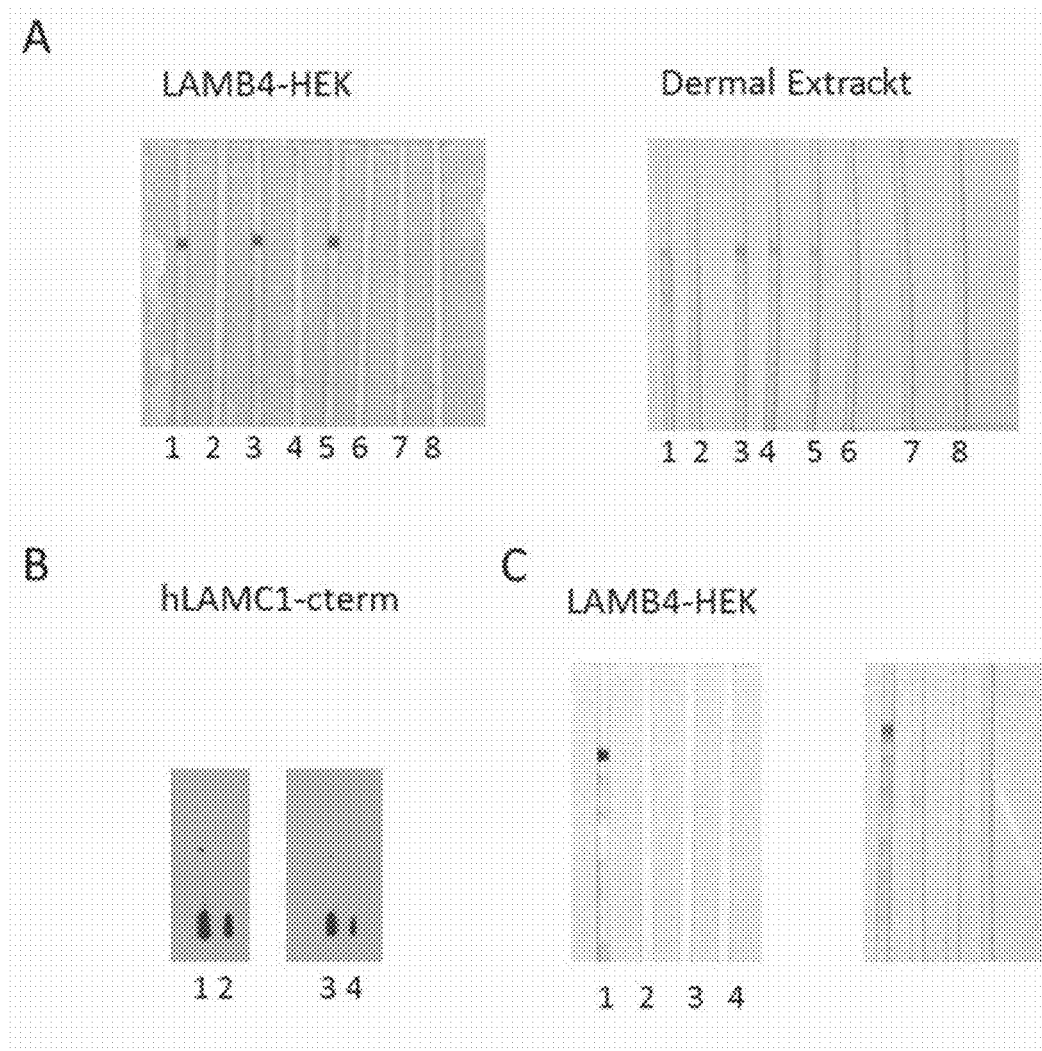
FIG. 4 shows the results of the preadsorption study. Anti-p200 pemphigoid sera were preadsorbed with the HEK293-laminin beta-4 extract (overnight) and then tested for their reactivity in a western blot. A: Left: Three anti-p200 pemphigoid sera were preadsorbed overnight with HEK293-laminin beta-4 extract and no longer exhibited a signal (strips 2, 4, 6) in comparison with the non-preadsorbed sera (1, 3, 5) in the subsequent western blot with laminin beta-4; strip 7: normal human serum: strip 8: preadsorbed normal human serum. Right: The same samples were also incubated with nitrocellulose strips of dermal extract and exhibited the same result. Only serum No. 2 reacted, despite preadsorption, in the western blot with dermal extract. B: In a western blot with recombinant hLAMC1-cterm, it was possible to show that serum No. 2 also reacted with laminin gamma-1. C: Renewed preadsorption of serum No. 2 with hLAMC1-cterm and the cell extract with expression of laminin beta-4. It was possible to cancel the autoantibody reactivity with both extracts. Strip 1: anti-p200 pemphigoid serum (No. 2): strip 2: preadsorbed anti-p200 pemphigoid serum (No. 2): strip 3: normal human serum; strip 4: preadsorbed normal human serum.

FIG. 4 shows the results of the preadsorption study. Anti-p200 pemphigoid sera were preadsorbed with the HEK293-laminin beta-4 extract (overnight) and then tested for their reactivity in a western blot. A: Left: Three anti-p200 pemphigoid sera were preadsorbed overnight with HEK293-laminin beta-4 extract and no longer exhibited a signal (strips 2, 4, 6) in comparison with the non-preadsorbed sera (1, 3, 5) in the subsequent western blot with laminin beta-4; strip 7: normal human serum; strip 8: preadsorbed normal human serum. Right: The same samples were also incubated with nitrocellulose strips of dermal extract and exhibited the same result. Only serum No. 2 reacted, despite preadsorption, in the western blot with dermal extract. B: In a western blot with recombinant hLAMC1-cterm, it was possible to show that serum No. 2 also reacted with laminin gamma-1. C: Renewed preadsorption of serum No. 2 with hLAMC1-cterm and the cell extract with expression of laminin beta-4. It was possible to cancel the autoantibody reactivity with both extracts. Strip 1: anti-p200 pemphigoid serum (No. 2); strip 2: preadsorbed anti-p200 pemphigoid serum (No. 2): strip 3: normal human serum; strip 4: preadsorbed normal human serum.

Figure 5:
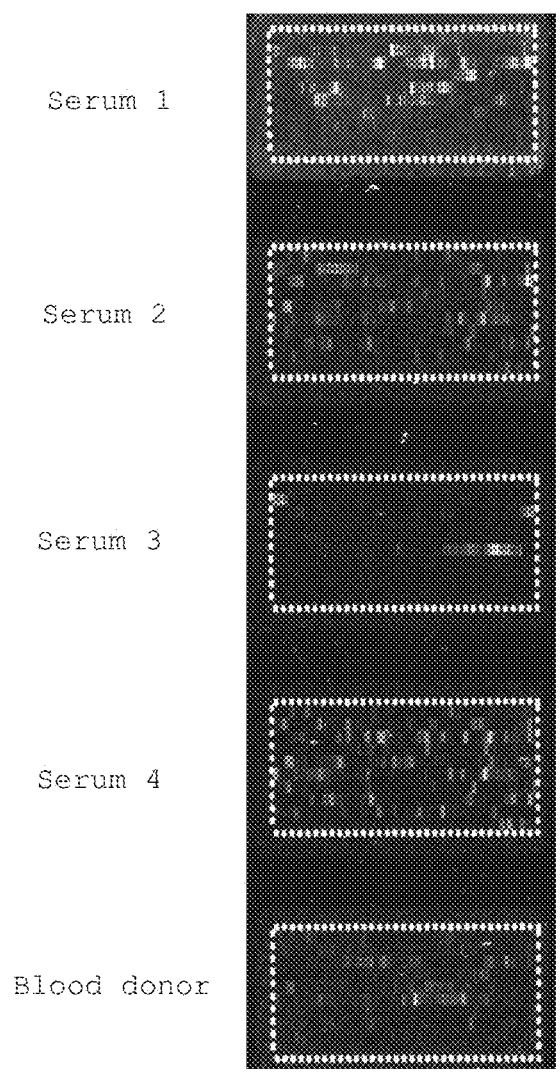
FIG. 5 shows exemplary primary data from precise epitope mapping. What can be seen is the signal obtained from a microarray after the incubation of four patient sera and a sample from a blood donor (each 1:10 diluted) and IgG secondary antibody.

FIG. 5 shows exemplary primary data from precise epitope mapping. What can be seen is the signal obtained from a microarray after the incubation of four patient sera and a sample from a blood donor (each 1:10 diluted) and IgG secondary antibody.

EXAMPLES

Example 1: Identification of Laminin Beta-4 as Diagnostically Relevant Autoantigen Preparation of Dermal Extract A further autoantigen of anti-p200 pemphigoid was identified by first carrying out an immunoprecipitation with extract of human dermis and purified patient antibody.

To this end, the dermal extract was first prepared (Zillikens D, Kawahara Y. Ishiko A, Shimizu H, Mayer J, Rank C V. Liu Z, Giudice G J, Tran H H, Marinkovich M P, Brocker E B, and Hashimoto T, A novel subepidermal blistering disease with autoantibodies to a 200-kDa antigen of the basement membrane zone. J Invest Dermatol, 1996, 106(6): pp. 1333-8). Human skin pieces were incubated at 4° C. for 48 h in PBS (phosphate-buffered saline) containing 1 M NaCl, 5 mM EDTA, 1 mM PMSF and protease inhibitor cocktail (Set III, Merck). After 48 h, it was then possible to separate the dermis and the epidermis from one another. The proteins were extracted from the dermis by first overlaying the dermis with a 4 M urea buffer (4 M urea, 12.5 mM Tris-HCl, pH 6.8, 5 mM EDTA, 1 mM PMSF) for 10 min, then removing the buffer and subsequently carrying out an incubation with a 9 M urea buffer (9 M urea, 12.5 mM Tris-HCl, pH 6.8, 2% SDS, 100 mM DTT, 5 mM EDTA and 1 mM PMSF) for 1 hour. The resulting extract was rebuffered in RIPA buffer (radioimmunoprecipitation assay buffer: 0.1% SDS, 1% NP-40, 0.5% Na deoxycholate, protease inhibitors (1 tablet of SIGMAFAST" Protease Inhibitor Cocktail Tablets. EDTA-Free, Sigma Aldrich)) using desalting columns (Zeba™ Spin Desalting Columns, Thermo Scientific) and stored at −20° C. until use.

Affinity Purification of IgG Antibodies

Anti-p200 pemphigoid IgG was purified using Protein G Sepharose (Genscript) according to the instructions from the manufacturer. Thereafter, the hLAMC1-cterm (C-terminus of human laminin gamma-1, amino acids 1363-1609) specific autoantibodies were isolated with the aid of an affinity purification procedure (Vafia K. Groth S, Beckmann T, Hirose M. Dworschak J, Recke A. Ludwig R J, Hashimoto T, Zillikens D, and Schmidt E, Pathogenicity of autoantibodies in anti-p200 pemphigoid. PLoS One, 2012. 7(7): p. e41769). For the specific purification of the patient antibodies, hLAMC1-cterm-pQE40 was first transformed into E. coli Rosetta 2 DE3 (Novagen/Merck, Darmstadt) and the protein was expressed and purified (by means of IMAC). Lastly, the recombinant hLAMC1-cterm protein was covalently coupled to Affigel 15 (BIO RAD) according to the instructions from the manufacturer (Groth S, Recke A, Vafia K, Ludwig R J, Hashimoto T, Zillikens D, and Schmidt E, Development of a simple enzyme-linked immunosorbent assay for the detection of autoantibodies in anti-p200 pemphigoid. Br J Dermatol, 2011. 164(1): pp. 76-82). With the aid of this specific affinity chromatography, it was possible to remove the hLAMC1-cterm-specific autoantibodies from the IgG preparations of the anti-p200 pemphigoid patient sera.

Immunoprecipitation

What were used in the immunoprecipitation were the rebuffered dermal extract as protein source and the purified patient IgG without hLAMC1-cterm reactivity, an anti-p200 pemphigoid serum without hLAMC1-cterm antibodies, and the corresponding controls from healthy blood donors.

First, the Protein G Sepharose (GammaBind G Sepharose, GE Healthcare) was washed with RIPA buffer and preadsorbed with serum from a healthy blood donor. After the one-hour preadsorption and centrifugation, the Sepharose was incubated with in each case:

1. 30 µg of patient IgG (pool) without hLAMC1-cterm reactivity
2. 20 µl of patient serum
3. 30 mg of NH IgG (normal human IgG from healthy blood donors)
4. 20 µl of NHS (normal human serum from a healthy blood donor)
5. only RIPA buffer in RIPA buffer at room temperature for 1 h with rotation and subsequently washed with RIPA buffer. 200 µl of the rebuffered dermal extract were then pipetted into each reaction tube and the reaction preparations were then incubated overnight at 4° C. on a rotator. A wash step with RIPA buffer was followed by a wash step with sucrose buffer (I M sucrose, 150 mM NaCl, 10 mM EDTA, 10 mM HNaPO4). Finally, a wash step with RIPA buffer was carried out once again. The samples were each heated at 95° C. for 5 min with 20 µl of Laemmli buffer and centrifuged and the samples were loaded on 7.5% PROTEAN TGX protein gels (BIO RAD).

One half of the gel was Coomassie (silver blue) stained and the other half was, after transfer of the proteins to a nitrocellulose membrane, analyzed in a western blot with an anti-p200 pemphigoid serum (dilution 1:50, incubation overnight at 4° C.). The buffers used were TBS-T containing 5% milk powder for saturating free binding sites and TBST containing 5% milk powder and 1% BSA as incubation buffer. The secondary antibody used was an anti-human IgG4 HRP antibody (1:2000, clone HP6025. Southern Biotech). The blot was developed with DAB (3,3'-diaminobenzidine). It was possible to observe a distinct signal at approx. 200 kDa (FIG. 1). The corresponding bands from the Coomassie-stained gel were subjected to an LC-MS/MS analysis (Wistar Institute. Philadelphia) and it was possible to identify them as laminin beta-4 (LAMB4).

Example 2: Checking of the Localization of Laminin Beta-4

The localization of laminin beta-4 in the skin was checked by first using a commercially available anti-laminin beta-4 antibody (polyclonal, Cloud-Clone: PAC079Hu01) in indirect immunofluorescence. In contrast to the negative control, the anti-laminin beta-4 antibody, just like the anti-p200 pemphigoid sera (not shown), bound in the base of the artificial blister in human salt-split skin. In addition, the anti-laminin beta-4 antibody was also tested in a western blot with dermal extract (see above for the procedure). The western blot with dermal extract is the current diagnostic standard for diagnosing anti-p200 pemphigoid. As shown by FIG. 2, the anti-laminin beta-4 antibody (strip 4) reacted with a protein band situated on the same level with the signal of the anti-p200 pemphigoid sera (strips 1 and 2). The signal of the commercial monoclonal laminin gamma-1 antibody (clone B-4, Santa Cruz) was shifted slightly upward.

In addition, the commercial anti-laminin beta-4 antibody was used for an immunoprecipitation. Here too, the laminin beta-4 source used was again the dermal extract. 5 μg and 10 μg of anti-laminin beta-4 antibody were used for the immunoprecipitation (see above for the procedure). The controls used were anti-NC 16A rabbit IgG (10 μg), normal rabbit IgG (10 μg) and GammaBind G Sepharose on its own. In the subsequent western blot analysis, laminin beta-4 was detected using a pool of anti-p200 pemphigoid IgG without laminin gamma-1 reactivity. On FIG. 2, it can be clearly seen that the anti-p200) pemphigoid patients have autoantibodies against laminin beta-4.

Example 3: Cloning

Laminin beta-4 (LAMB4) was recombinantly produced as a variant with C-terminally fused polyhistidine-tag and as an authentic variant. The cDNA clone IRCBp5005F2212Q, encoding isoform 1 of human laminin beta-4, was purchased from Source BioScience (United Kingdom) and used as template for PCR.

For the amplification of the coding sequence of laminin beta-4, the sense primer LAMB4 (SEQ ID NO 1) and the anti-sense primer LAMB4 (SEQ ID NO 2) were used for the fragment without translation stop codon at the end of the sequence encoding laminin beta-4. The amplification of the laminin beta-4 cDNA with translation stop codon at the end of the coding sequence was carried out with the sense primer LAMB4 (SEQ ID NO 1) and the anti-sense primer LAMB4-Stop (SEQ ID NO 3).

At the ends, both PCR products contained restriction sites for the restriction enzyme BsaI.

After BsaI digestion, the laminin beta-4 amplicons were ligated with the NcoI/XhoI-linearized plasmid vector pTriEx-1 (Merck, Darmstadt, Germany, SEQ ID NO 4), yielding the constructs as per SEQ ID NO 5 and SEQ ID NO 6. The ligation preparations were transformed into E. coli NEB 5-alpha (New England Biolabs GmbH) and transformants were selected by means of 100 μg/ml ampicillin. The isolated plasmids were checked for correctness by means of restriction analyses and DNA sequencing and used for the transfection of HEK293 cells.

Example 4: Transfection of HEK Cells and Western Blot Analysis

To check that laminin beta-4 is actually a target antigen of anti-p200 pemphigoid, HEK293 cells were transfected with LAMB4-pTriEx1 (with His-tag, SEQ ID NO 7) or the empty vector by means of jetPRIME (Polyplus transfection) and expression was checked after 48 h in a western blot by means of a commercial anti-laminin beta-4 antibody (see above). Altogether, 49 anti-p200 pemphigoid sera (dilution 1:50) and 20 sera from healthy blood donors (NHS, normal human sera, dilution 1:50) were tested for their reactivity with laminin beta-4 in a western blot with the laminin beta-4-HEK293 extract (RIPA buffer). To this end, the finished nitrocellulose membrane was cut into strips. The commercial anti-laminin beta-4 antibody (dilution 1:2000) was used as positive control. The strips were incubated with the primary antibodies overnight at 4° C. Here too, as described above, an anti-human IgG4 HRP antibody and a mouse anti-rabbit HRP antibody were used as secondary antibody. The blot was developed with DAB for 1 min. Altogether, 47 of the 49 anti-p200 pemphigoid sera reacted with laminin beta-4, whereas the negative controls exhibited no reactions.

Example 5: Preadsorption Study

The correct identification of laminin beta-4 was confirmed by a preadsorption study. To this end, three anti-p200 pemphigoid sera (without laminin gamma-1 reactivity) were preadsorbed with the laminin beta-4-HEK293 extract overnight at 4° C. and then tested for their remaining reactivity in a western blot with dermal extract and laminin beta-4-HEK293 extract (FIG. 4). The western blot analysis was carried out as described above. Compared to the non-preadsorbed sera (FIG. 4, strips 1, 3 and 5), the preadsorbed sera no longer exhibited reactivity with the laminin beta-4-HEK293 extract, and 2 of the 3 preadsorbed sera also no longer reacted with the 200 kDa sized protein in the dermal extract. The reaction could thus be neutralized. Only serum No. 2 still exhibited an attenuated reaction at about 200 kDa. This anti-p200 pemphigoid serum should actually exhibit no reactivity with laminin gamma-1, but testing was nevertheless carried out again using an hLAMC1-cterm western blot. It emerged that serum No. 2 actually has laminin gamma-1 autoantibodies, and this can thereby explain the reaction in the dermal extract.

By means of a preadsorption of serum No. 2 with hLAMC1-cterm and the laminin beta-4-HEK293 extract, it was possible to cancel the autoantibody reactivity with both extracts. The negative control used in this study was the serum from a healthy blood donor (NHS).

Example 6: Rough Epitope Mapping

To identify rough epitopes, six subfragments of laminin beta-4 (SEQ ID NO 15, SEQ ID NO 16, SEQ ID NO 17, SEQ ID NO 18, SEQ ID NO 19 and SEQ ID NO 20) were cloned and expressed in a pET24d vector with C-terminal His-tag using standard protocols (SEQ ID NO 21, SEQ ID NO 22, SEQ ID NO 23, SEQ ID NO 24, SEQ ID NO 25 and SEQ ID NO 26). Where the constructs did not already have four tryptophan residues, they were artificially fused on in a number for each construct to have four tryptophans for concentration measurement.

The constructs were subjected to a western blot analysis, as described in Example 1.

The results are combined in Table 1. Essentially, what became apparent was considerable activity against subfragment (SF) 5 and SF 6. By contrast, the sera from blood donors (BD) showed practically no reactivity.

| | Sera | SF 1 | SF 2 | SF 3 | SF 4 | SF 5 | SF 6 |
|---|---|---|---|---|---|---|---|
| p200 | 1 | + | weak + | + | weak + | + | +++ |
| | 2 | – | – | – | – | weak + | +++ |
| | 3 | + | + | + | – | – | +++ |
| | 4 | – | – | – | – | – | +++ |
| | 5 | – | + | – | + | ++ | +++ |
| | 6 | – | – | – | – | ++ | +++ |
| | 7 | + | + | – | – | ++ | +++ |
| | 8 | + | + | weak + | + | ++ | +++ |
| | 9 | – | – | – | – | ++ | +++ |
| | 10 | – | – | + | – | + | +++ |
| | 11 | + | – | weak + | – | ++ | +++ |
| | 12 | + | + | weak + | – | ++ | +++ |
| | 13 | – | – | – | – | + | +++ |
| | 14 | – | – | – | – | ++ | ++ |
| | 15 | – | – | – | – | + | ++ |
| | 16 | – | – | – | – | – | ++ |
| | 17 | – | – | – | – | + | +++ |
| | 18 | – | – | – | + | – | +++ |
| | 19 | – | – | – | – | – | +++ |
| | 20 | – | – | – | + | | +++ |
| | | 6/20 | 6/20 | 6/20 | 5/20 | 14/20 | 20/20 |
| NHS | BD1 | – | – | – | – | – | – |
| | BD2 | – | – | – | – | – | – |
| | BD3 | – | – | – | – | – | – |
| | BD4 | – | – | – | – | – | – |
| | BD5 | – | – | – | – | – | – |
| | BD6 | – | – | – | – | – | – |
| | BD7 | – | – | – | – | – | – |
| | BD8 | – | – | – | – | – | – |
| | BD9 | – | – | – | – | – | – |
| | BD10 | – | – | – | – | – | – |
| | BD11 | – | – | – | – | – | – |
| | BD12 | – | – | – | – | – | – |
| | BD13 | – | – | – | – | – | – |
| | BD14 | unspecific | unspecific | unspecific | unspecific | unspecific | unspecific |
| | BD15 | – | – | – | – | – | – |
| | BD16 | – | – | – | – | – | – |
| | BD17 | – | – | – | – | – | – |
| | BD18 | – | – | – | – | – | weak? |
| | BD19 | unspecific | unspecific | unspecific | unspecific | unspecific | unspecific |
| | BD20 | – | – | – | – | – | poss. 1/20 |

Example 7: Precise Epitope Mapping

Four patient sera comprising autoantibodies against laminin beta-4 were used for epitope mapping. The serum from a blood donor was additionally incubated in order to be able to identify unspecific reactions. Use was made of linear 15mer peptides with an overlap of 14 amino acids, which map the C-terminal portion, more precisely subfragments 5 (SEQ ID NO 19) and 6 (SEQ ID NO 20). The peptides were contacted with the samples at a dilution of 1:100 in incubation buffer (PBS, pH 7.4 containing 0.05% Tween 20 with 10% Rockland blocking buffer MB-070) and incubated in incubation buffer for 16 h at 4° C. and with shaking at 140 rpm and in dilutions of 1:500, 1:100 and 1:10, followed by 45 min of staining with secondary (mouse anti-human IgG (Fc) DyLight680 (0.5 µg/ml)) and control (mouse monoclonal anti-HA (12CA5) DyLight680 (0.2 µg/ml)) antibodies. Reading was carried out using a LI-COR Odyssey Imaging System. Quantification of the spot intensities and peptide annotation were carried out using a PepSlide Analyzer. Exemplary primary data can be seen in FIG. 5.

Result: What were determined were low to moderate specific antibody reactions with peptides, meaning that it was possible to identify the epitopes having the sequences SEQ ID NO 8, SEQ ID NO 9, SEQ ID NO 10, SEQ ID NO 11. SEQ ID NO 12, SEQ ID NO 13 and SEQ ID NO 14.

The invention claimed is:

1. A method, comprising:

contacting a liquid sample comprising antibodies from a patient having anti-p200 pemphigoid to a carrier having laminin beta-4 immobilized thereon wherein the laminin beta-4 comprises one of SEQ ID NOs: 8-14 and 27 wherein a complex is formed between an antibody in the liquid sample and the laminin beta-4;

detecting an antibody against the laminin beta-4 by an assay that comprises contacting the complex with a secondary antibody that comprises a detectable label, wherein the assay does not detect the complex when control sera is contacted to the carrier, the control sera being obtained from an individual who does not have anti-p200 pemphigoid.

2. The method as claimed in claim 1, wherein the assay uses at least one method selected from the group consisting of immunodiffusion, immunoelectrophoresis, light scattering, agglutination, and ELISA.

3. A method for purifying an autoantibody to laminin beta-4, comprising:

a) contacting a liquid comprising the autoantibody with a laminin beta-4 polypeptide under conditions which allow the formation of a complex comprising the autoantibody and the laminin beta-4 polypeptide, wherein the laminin beta-4 polypeptide comprises one of SEQ ID NOs: 8-14, and 27, b) isolating the complex from a), c) dissociating the complex isolated in b), and d) purifying the autoantibody.

4. A method of detecting an autoantibody in an anti-p200 pemphigoid liquid sample, comprising:

(a) immobilizing a laminin beta-4 polypeptide comprising one of SEQ ID NOs: 8-14 and 27 on a carrier;

(b) contacting said liquid sample with the carrier of (a) under conditions which allow formation of a complex; and (c) detecting the complex of (b) using an agent which binds the complex and has a detectable label wherein the binding is elevated as compared to the binding detected by said agent when detecting a complex formed when control sera is contacted with the carrier of (a), the control sera being obtained from an individual who does not have anti-p200 pemphigoid.

5. The method of claim 4, wherein the detecting step of (c) uses at least one method selected from the group consisting of immunodiffusion, immunoelectrophoresis, light scattering, agglutination, and ELISA.

6. A method of isolating an autoantibody from an anti-p200 pemphigoid liquid sample, comprising:

(a) contacting said liquid sample with a laminin beta-4 polypeptide comprising one of SEQ ID NOs: 8-14 and 27 under conditions which allow formation of a complex;

(b) isolating the complex from (a);

(c) dissociating the complex isolated in (b); and (d) removing the laminin beta-4 polypeptide from the autoantibody.

* * * * *

UNITED STATES PATENT AND TRADEMARK OFFICE
CERTIFICATE OF CORRECTION

PATENT NO. : 11,208,465 B2
APPLICATION NO. : 16/591333
DATED : December 28, 2021
INVENTOR(S) : Christian Probst et al.

It is certified that error appears in the above-identified patent and that said Letters Patent is hereby corrected as shown below:

In the Specification

Column 27, Line 21 at SEQ ID No. 5 currently reads:
"AGTTTGCCATTCTTGACCTGTGATGTGGATACAGGCCAATGCTTGTGCCTGTCATA"
And should read:
-- AGTCTGCCATTCTTGACCTGTGATGTGGATACAGGCCAATGCTTGTGCCTGTCATA --;

Column 33, Line 29 at SEQ ID NO. 5 currently reads:
"AACTTTAAAAGTGCTCATCATTGGAAAACGTTCTTCGOGGCGAAAACTCTCAAGG"
And should read:
-- AACTTTAAAAGTGCTCATCATTGGAAAACGTTCTTCGGGGCGAAAACTCTCAAGG --;

Column 35, Line 19 at SEQ ID NO. 5 currently reads:
"GCAGCCT-TCAGAGCGGCGCGCTCCGAAAGTTTCCTTTTATGGCGAGGCGGCGGC"
And should read:
-- GCAGCCAATCAGAGCGGCGCGCTCCGAAAGTTTCCTTTTATGGCGAGGCGGCGGC --;

Column 35, Line 40 at SEQ ID NO. 6 currently reads:
"TGACCTTTAAGACTTTT-GGCCTGCTGCAATGTTAGTTGAACGTTCCACAGACTAT"
And should read:
-- TGACCTTTAAGACTTTTCGGCCTGCTGCAATGTTAGTTGAACGTTCCACAGACTAT --;

Column 37, Line 7 at SEQ ID NO. 6 currently reads:
"GAAGATGCGGGGAGATGTTTTCAGCCCTCCTGGAATGGTTCACG-TCAGTGTGTG"
And should read:
-- GAAGATGCGGGGAGATGTTTTCAGCCCTCCTGGAATGGTTCACGGTCAGTGTGTG --;

Column 37, Line 27 at SEQ ID NO. 6 currently reads:
"AGCACTGCATACCCAAGACTCTACAGTTAAAGCCTCAGTCTTTTGCCTTACCAGC"
And should read:

Signed and Sealed this
Eighteenth Day of October, 2022

*Katherine Kelly Vidal*

Katherine Kelly Vidal
*Director of the United States Patent and Trademark Office*

CERTIFICATE OF CORRECTION (continued)
U.S. Pat. No. 11,208,465 B2

-- AGCACTGCATACCCAAGACTCTACAGTCAAAGCCTCAGTCTTTTGCCTTACCAGC --;

Column 43, Line 5 at SEQ ID NO. 6 currently reads:
"CTGGAAGCTCCCTCGGTCGCTCTCCTGTTCCGACCCTGCCGCTTACCGGATACCTG"
And should read:
-- CTGGAAGCTCCCTCGTGCGCTCTCCTGTTCCGACCCTGCCGCTTACCGGATACCTG --;

Column 45, Line 40 at SEQ ID NO. 7 currently reads:
"LNEQLKAVYEFQDLKDTIERAKNEADLLLEDLQEEIDLQSSVINASIADSSENIKKYY"
And should read:
-- LNEQLKAVYEFQDLKDTIERAKNEADLLLEDLQEEIDLQSSVLNASIADSSENIKKYY --;

Column 47, Line 2 at SEQ ID NO. 7 currently reads:
"KQVRGLKNQIESISEQAEVSKNNALQLREKLGNIRNQSDSEEENINLFIKKVKNF-LEE"
And should read:
-- KQVRGLKNQIESISEQAEVSKNNALQLREKLGNIRNQSDSEEENINLFIKKVKNFLLEE --;

Column 47, Line 5 at SEQ ID NO. 7 currently reads:
"NQTREMKSELELAKQRSGLEDGLSLLQTK-QRHQDHAVNAKVQAESAQHQAGSLEK"
And should read:
-- NQTREMKSELELAKQRSGLEDGLSLLQTKLQRHQDHAVNAKVQAESAQHQAGSLEK --;

Column 49, Line 7 at SEQ ID NO. 19 currently reads:
"YEFQDLKDTIERAKNEADLLLEDLQEEIDLQSSV-NASIADSSENIKKYYHISSSAEKKI"
And should read:
-- YEFQDLKDTIERAKNEADLLLEDLQEEIDLQSSVLNASIADSSENIKKYYHISSSAEKKI --;

Column 49, Line 13 at SEQ ID NO. 20 currently reads:
"HLPIPSINLTDELVKIQKHMQLCEDYRTDENRLNEEADGAQKLLVKAKAAEKAANIL"
And should read:
-- IHLPIPSQNLTDELVKIQKHMQLCEDYRTDENRLNEEADGAQKLLVKAKAAEKAANIL --;

Column 49, Line 23 at SEQ ID NO. 21 currently reads:
"PSTGGEVVLKVLDPSFIEIENPYSPYIQDLVTLTNLRINFTKLHTLGDALLGRRQNDSLD"
And should read:
-- PSTGGEVVLKVLDPSFEIENPYSPYIQDLVTLTNLRINFTKLHTLGDALLGRRQNDSLD --.